United States Patent
Laing et al.

(10) Patent No.: US 10,976,307 B2
(45) Date of Patent: *Apr. 13, 2021

(54) WHOLE CELL ASSAYS AND METHODS

(71) Applicant: Celcuity Inc., Minneapolis, MN (US)

(72) Inventors: Lance Gavin Laing, Orono, MN (US); Brian Francis Sullivan, Medina, MN (US)

(73) Assignee: Celcuity Inc., Minneapolis, MN (US)

( * ) Notice: Subject to any disclaimer, the term of this patent is extended or adjusted under 35 U.S.C. 154(b) by 339 days.

This patent is subject to a terminal disclaimer.

(21) Appl. No.: 16/027,073

(22) Filed: Jul. 3, 2018

(65) Prior Publication Data

US 2018/0321222 A1    Nov. 8, 2018

Related U.S. Application Data

(63) Continuation of application No. 15/192,280, filed on Jun. 24, 2016, now Pat. No. 10,041,934, which is a continuation of application No. 14/590,731, filed on Jan. 6, 2015, now Pat. No. 9,404,915, which is a continuation of application No. 13/494,618, filed on Jun. 12, 2012, now abandoned.

(51) Int. Cl.
*G01N 33/50* (2006.01)
*G01N 33/574* (2006.01)
*G01N 27/02* (2006.01)

(52) U.S. Cl.
CPC ......... *G01N 33/5011* (2013.01); *G01N 27/02* (2013.01); *G01N 33/5044* (2013.01); *G01N 33/574* (2013.01)

(58) Field of Classification Search
CPC ................................................ G01N 33/5011
USPC .......................................................... 435/29
See application file for complete search history.

(56) References Cited

U.S. PATENT DOCUMENTS

| | | |
|---|---|---|
| 4,816,567 A | 3/1989 | Cabilly et al. |
| 6,041,642 A | 3/2000 | Duncan |
| 6,077,684 A | 6/2000 | Kravtsov |
| 6,258,553 B1 | 7/2001 | Kravtsov |
| 6,331,392 B1 | 12/2001 | Laing et al. |
| 6,372,772 B1 | 4/2002 | Kirkpatrick et al. |
| 6,399,078 B1 | 6/2002 | Devico et al. |
| 6,569,628 B2 | 5/2003 | Laing et al. |
| 6,673,596 B1 | 1/2004 | Sayler et al. |
| 6,974,706 B1 | 12/2005 | Melker et al. |
| 7,192,752 B2 | 3/2007 | Xu et al. |
| 7,429,492 B2 | 9/2008 | Lin et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,560,269 B2 | 7/2009 | Wang et al. |
| 7,592,188 B2 | 9/2009 | Hahn et al. |
| 7,628,085 B2 | 12/2009 | Laing et al. |
| 7,790,406 B2 | 9/2010 | Cunningham et al. |
| 7,832,291 B2 | 11/2010 | Laing et al. |
| 7,863,052 B2 | 1/2011 | Schulz et al. |
| 7,927,822 B2 | 4/2011 | Genick et al. |
| 7,960,170 B2 | 6/2011 | Schulz et al. |
| 8,061,220 B2 | 11/2011 | Laing et al. |
| 8,168,568 B1 | 5/2012 | Mehta et al. |
| 8,202,735 B2 | 6/2012 | Genick et al. |
| 8,257,936 B2 | 9/2012 | Laing et al. |
| 8,298,780 B2 | 10/2012 | Wagner et al. |
| 9,404,915 B2 | 8/2016 | Laing et al. |
| 10,041,934 B2 | 8/2018 | Laing et al. |
| 2002/0031778 A1 | 3/2002 | Laing et al. |
| 2003/0004140 A1 | 1/2003 | Dalton et al. |
| 2003/0096275 A1 | 5/2003 | Laing |
| 2003/0152992 A1 | 8/2003 | Laing et al. |
| 2004/0084307 A1 | 5/2004 | Kim et al. |
| 2004/0115713 A1 | 6/2004 | Laing |
| 2004/0115786 A1 | 6/2004 | Laing |
| 2005/0130321 A1 | 6/2005 | Nicholson et al. |
| 2006/0003372 A1 | 1/2006 | Li et al. |
| 2006/0120204 A1 | 6/2006 | Abassi et al. |
| 2006/0141508 A1 | 6/2006 | Palmer |

(Continued)

FOREIGN PATENT DOCUMENTS

| | | |
|---|---|---|
| JP | 2011514522 A | 5/2011 |
| JP | 2012526992 A | 11/2012 |

(Continued)

OTHER PUBLICATIONS

Cunningham et al. (Journal of Biomolecular Screening, 9(6), 2004, pp. 481-490). (Year: 2004).*
Niepel, M. et al., "Profiles of Basal and stimulated receptor signaling networks predict drug response in breast cancer lines," Science Signaling, vol. 6 (294): ra84, 12 pages (2013).
Wallasch, C. et al., "Heregulin-dependent regulation of HER2/neu oncogenic signaling by heterodimerization with HER3," EMBO Journal, vol. 14:4267-4275 (1995).
Choi, B-K., et al., "ERBB3 (HER3) is a key sensor in the regulation of ERBB-mediated signaling in both low and high ERBB2 (HER2) expressing cancer cells," Cancer Medicine, vol. 1:28-38(2013).
Cragg, M. et al, "Unleashing the power of inhibitors of oncogenic kinases through BH3 mimetics," Nature Reviews Cancer, vol. 9:321-326 (2009).
Davis et al, "Comprehensive analysis of kinase inhibitor selectivity," Nature Biotechnology, vol. 29:(11)1046-1051 (2011).

(Continued)

*Primary Examiner* — Karla A Dines
(74) *Attorney, Agent, or Firm* — Nelson Mullins Riley & Scarborough LLP; Jane E. Remillard, Esq.

(57) ABSTRACT

The disclosure provides methods for analysis of disease cell response to a therapeutic agent. In embodiments, a method comprises administering the therapeutic agent to a disease cell sample from the subject in a device that measures at least one physiological parameter of a cell; determining whether a change occurs in the physiologic parameter of the disease cell sample in response to the therapeutic agent as compared to a baseline measurement or the physiological parameter before administration of the therapeutic agent, and selecting the therapeutic agent that results in the change in the at least one physiologic parameter. In embodiments, the disease cells are whole, viable, and/or label free.

20 Claims, 12 Drawing Sheets

(56) References Cited

U.S. PATENT DOCUMENTS

| | | |
|---|---|---|
| 2006/0160109 A1 | 7/2006 | MacDonald et al. |
| 2006/0177476 A1 | 8/2006 | Saffran |
| 2006/0275825 A1 | 12/2006 | Baird et al. |
| 2006/0292581 A1 | 12/2006 | Laing |
| 2007/0065415 A1 | 3/2007 | Kleinsek et al. |
| 2007/0172894 A1 | 7/2007 | Genick et al. |
| 2008/0020480 A1 | 1/2008 | Lin et al. |
| 2008/0115567 A1 | 5/2008 | Laing et al. |
| 2008/0240543 A1 | 10/2008 | Budach et al. |
| 2008/0299673 A1 | 12/2008 | Wagner et al. |
| 2009/0017488 A1 | 1/2009 | Binder et al. |
| 2009/0060970 A1 | 3/2009 | Toner et al. |
| 2009/0102981 A1 | 4/2009 | Mody |
| 2009/0130703 A1 | 5/2009 | Wagner et al. |
| 2009/0137422 A1 | 5/2009 | Laing et al. |
| 2009/0142790 A1 | 6/2009 | Fang et al. |
| 2009/0192049 A1 | 7/2009 | Baird et al. |
| 2009/0226950 A1 | 9/2009 | Cunningham et al. |
| 2009/0282931 A1 | 11/2009 | Laing et al. |
| 2009/0298162 A1 | 12/2009 | Bouvier et al. |
| 2009/0305304 A1 | 12/2009 | Laing et al. |
| 2010/0003743 A1 | 1/2010 | Schulz et al. |
| 2010/0015721 A1 | 1/2010 | Laing |
| 2010/0043571 A1 | 2/2010 | Laing et al. |
| 2010/0140087 A1 | 6/2010 | Ueno et al. |
| 2010/0143959 A1 | 6/2010 | Cunningham et al. |
| 2010/0196925 A1 | 8/2010 | Genick et al. |
| 2010/0202923 A1 | 8/2010 | Cunningham et al. |
| 2010/0227769 A1 | 9/2010 | Schulz et al. |
| 2010/0291575 A1 | 11/2010 | Shamah et al. |
| 2010/0329933 A1 | 12/2010 | Schulz et al. |
| 2011/0117542 A1 | 5/2011 | Abassi et al. |
| 2011/0130302 A1 | 6/2011 | Shen et al. |
| 2011/0195047 A1 | 8/2011 | Aldabe Arregui et al. |
| 2011/0231103 A1 | 9/2011 | Fang |
| 2012/0040866 A1 | 2/2012 | Laing et al. |
| 2012/0101230 A1 | 4/2012 | Wang et al. |
| 2012/0107840 A1 | 5/2012 | Wagner et al. |
| 2012/0237502 A1 | 9/2012 | Darnowski |
| 2013/0045880 A1 | 2/2013 | Singh et al. |
| 2013/0210057 A1 | 8/2013 | Deng et al. |
| 2013/0330761 A1 | 12/2013 | Laing et al. |
| 2015/0125894 A1 | 5/2015 | Laing et al. |
| 2016/0305932 A1 | 10/2016 | Laing et al. |
| 2017/0067875 A1 | 3/2017 | Laing et al. |
| 2017/0343554 A1 | 11/2017 | Sullivan et al. |
| 2019/0025287 A1 | 1/2019 | Laing et al. |

FOREIGN PATENT DOCUMENTS

| | | |
|---|---|---|
| JP | 2013-543006 A | 11/2013 |
| WO | 03/008530 A2 | 1/2003 |
| WO | 2006/113747 A2 | 10/2006 |
| WO | 2006108183 A2 | 10/2006 |
| WO | 2007/081779 A2 | 7/2007 |
| WO | 2009108637 A1 | 9/2009 |
| WO | 2010/052225 A1 | 5/2010 |
| WO | 2010/085845 A1 | 8/2010 |
| WO | 2010/098166 A1 | 9/2010 |
| WO | 2010132723 A1 | 11/2010 |
| WO | 2012068435 A1 | 5/2012 |
| WO | 2012/157647 A1 | 11/2012 |
| WO | 2013033623 A1 | 3/2013 |
| WO | 2013086301 A1 | 6/2013 |
| WO | 2013/188500 A1 | 12/2013 |
| WO | 2014/083178 A1 | 6/2014 |
| WO | 2015/089380 A2 | 6/2015 |
| WO | 2016/094904 A1 | 6/2016 |

OTHER PUBLICATIONS

Gharwan, H. et al. "Kinase inhibitors and monoclonal antibodies in oncology: clinical implications," Nature Reviews Clinical Oncology, vol. 13:209-227 (2016).

Ona, T. et al., "Advanced dynamic monitoring of cellular status using label-free and non-invasive cell-based sensing technology for the prediction of anticancer drug efficacy," Anal. Bioannal. Chem., vol. 398:2505-2533 (2010).

Sun, C. et al. "Feedback and redundancy in receptor tyrosine kinase signaling: relevance to cancer therapies," Trends in Biochemical Sciences, vol. 39: 465-474 (2014).

Arteaga, C. et al., "ERBB Receptors: From Oncogene Discovery to Basic Science to Mechanism-Based Cancer Therapeutics," Cancer Cell, vol. 25(3):282-303 (2014).

Laing, L. et al., "Dynamic real-time signaling profiles of live primary cells to characterize the response of PI3K and MAPK pathways in HER2+ breast cancer cells to attenuation with lapatinib: Tests of reproducibility of method," Journal of Clinical Oncology, vol. 32:15_suppl, e11597-e11597, 2014 American Society of Clinical Oncology (ASCO) (2014).

Laing, L., "Profiling of signaling pathways in live tumor cells to assess drug mechanism of action: A method to predict drug efficacy in a patient [e11583]," American Society of Clinical Oncologists 2014, Journal of Clinical Oncology, vol. 32:15_suppl, e11583-e11588, (2014) American Society of Clinical Oncology (ASCO) Poster Presentation.

Park, J. et al., "Rationale for Biomarkers and Surrogate End Points in Mechanism-Driven Oncology Drug Development," Clinical Cancer Research, vol. 10:3885-3896 (2004).

Peters, M. et al., "Comparing Label-Free Biosensors for Pharmacological Screening with Cell-Based Functional Assays," Assay and Drug Development Technolgoies, vol. 8(2):219-227 (2010).

Ressler, J. et al, "New concepts for chip-supported multi-well-plates: realization of a 24-well-plate with integrated impedance-sensors for functional cellular screening applications and automated microscope aided cell-based assays.," Proceedings of the IEEE EMBS, vol. 3: 2074-2077 (2004).

Schuler, M. et al., "A phase II trial to assess efficacy and safety of afatinib in extensively pretreated patients with HER2-negative metastatic breast cancer," Breast Cancer Research and Treatment, Kluwer Academic Publishers, BO, vol. 134 (3), pp. 1149-1159 (2012).

Scott, C. et al., "Label-free whole-cell assays: expanding the scope of GPCR screening," Drug Discovery Today, vol. 15,(17/18): 704-716(2010).

Solly, K. et al., "Application of real-time cell electronic sensing (RT-CES) technology to cell-based assays," Assay and Drug Development Technologies, vol. 2(4):363-372 (2004).

Sprague, L. et al., "Multiparametric Sensor-Chip Based Technology for Monitoring Metabolic Activity: A Proof-of-Principle Study with Live Tissue," Clin. Lab., vol. 52:375-384 (2006).

Struber, M. et al., "Low-potassium Dextran Solution Ameliorates reperfusion injury of the lung and protects surfactant function," The Journal of Thoracic and Cardiovascular Surgery, vol. 120(3):566-572 (2000).

Tyson, J. et al., "Dynamic modelling of oestrogen signalling and cell fate in breast cancer cells," Nature Reviews, vol. 11(7):523-530 (2011).

Xi, B. et al., "The application of cell-based label-free technology in drug discovery," Biotechnology Journal, vol. 3(4):484-495 (2008).

Xia, W. et al., "Anti-tumor activity of GW572016: a dual tyrosine kinase inhibitor blocks EGF activation of EGFR/erbB2 and down-stream Erk1/2 and AKT pathways," Oncogene, vol. 21(41):6255-6263 (2002).

Yang, TY. et al., "A multiple reaction monitoring (MRM) method to detect Bcr-Abl kinase activity in CML using a peptide biosensor," PLoS One, vol. 8, e56627, 10 pages (2013).

Buck, E. et al., "Loss of homotypic cell adhesion by epithelial-mesenchymal transition or mutation limits sensitivity to epidermal growth factor receptor inhibition," Mol Cancer Ther vol. 6(2):532-541(2007).

Endo, H. et al., "Spheroid Culture of Primary Lung Cancer Cells with Neuregulin 1 /HER3 Pathway Activation," Journal of Thoracic Oncology, vol. 8(2):131-139 (2013).

(56) References Cited

OTHER PUBLICATIONS

Kanakry, C., et al., "Neuregulin-1 regulates cell adhesion via an ErbB2/phosphoinositide-3 kinase/Akt-dependent pathway: potential implications for schizophrenia and cancer,"PLoS One, vol. 12:e1369: pp. 1-12 (2007).
Summons to Oral Proceedings, European Application No. 18157442.7, dated Nov. 21, 2018, 11 pages.
U.S. Appl. No. 15/179,119, dated Jun. 11, 2020.
U.S. Appl. No. 15/533,897, dated Mar. 13, 2020.
Abassi, Y., "Label-Free and Dynamic Monitoring of cell-Based Assays", Cell Analysis, Biochemica, No. 2, 8-11 (2008).
Ablin, R. J. et al., "Prostate Transglutaminase (TGase-4) Antagonizes the Anti-tumour Action of MDA-7/IL-24 in Prostate Cancer," Journal of Translational Medicine, vol. 9 (49): 1-8 (2008).
Aroui, S. et al., "Naringin suppresses cell metastasis and the expression of matrix metalloproteinases (MMP-2 and MMP-9) via the inhibition of ERK-P38-JNK signaling pathway in human glioblastoma," Chemico-Biological Interactions, vol. 244:195-203 (2015).
Atienza, J. et al., "Label-free and real-time cell-based kinase assay for; screening selective and potent receptor tyrosine kinase inhibitors using microelectronic sensor array", Journal of Biomolecular Screening, vol. 11(6): 634-643 (2006).
Bohunicky, B. et al., "Biosensors: the new wave in cancer diagnosis," Nanotechnology, Science and Applications, vol. 4:1-10 (2010).
Bosanquet, D. et al.,"Expression of IL-24 and IL-24 Receptors in Human Wound Tissues and the Biological Implications of IL-24 on Keratinocytes," Wound Repair and Regeneration, vol. 20: 896-903 (2012).
Brower, S. et al., "The ChemoFx® Assay: An Ex Vivo Chemosensitivity and Resistance Assay for Predicting Patient Response to Cancer Chemotherapy," Methods in Molecular Biology, vol. 414: Apoptosis and Cancer, 57-78 (2007).
Capuzzo, F., "The Human Epidermal growth factor Receptor (HER) family:structure and function," Guide to Targeted Therapies: EGFR mutations in NSCLC, Chapter Two, Springer International Publishing Switzerland, 12 pages (2014) DOI 10.1007/978-3-319-03059-3_2.
Chan, C-M et al., "Inhibitory Effects of Resveratrol on PDGF-BB-Induced Retinal Pigment Epithelial Cell Migration via PDGFR beta, PI3K/Akt and MAPK Pathways," PLOS, vol. 9, Issue 2, 1-14 (2013).
Chan, L. et al., "A label-free photonic crystal biosensor imaging method for detection of cancer cell cytotoxicity and proliferation," Apoptosis, vol. 12:1061-1068 (2007).
Chigaev, A. et al., "Galphas-coupled receptor signaling actively down-regulates alpha4beta1—integrin affinity: A possible mechanism for cell de-adhesion," BMC Immunology, vol. 9(26):1-16 (2008).
De Alava, E. et al., "Neuregulin expression modulates clinical response to trastuzumab in patients with metastatic breast cancer," Journal of Clinical Oncology,vol. 25(19):2656-2663 (2007).
European Examination Report, EP Application No. 13731594.1, dated Jun. 28, 2016, 11 pages.
Extended European Search Report, European Application No. 18157442.7 dated Apr. 3, 2018, 10 pages.
Fang, Ye, "Label-Free and Non=onvasive Biosensor Cellular Assays for Cell Adhesion," Journal of Adhesion Science and Technology, vol. 24:1011-1021 (2010).
Fountzilas, G. et al., "Evaluation of the prognostic role of centromere 17 gain and HER2/topoisomerase II alpha gene status and protein expression in patients with breast cancer treated with anthracycline-containing adjuvant chemotherapy: pooled analysis of two Hellenic Cooperative Oncology Group (HeCOG) phase III trials," BMC Cancer, vol. 13:163, 16 pages (2013).
Gianni, L. et al., "Open-Label, Phase II, Multicenter, Randomized Study of the Efficacy and Safety of Two Dose Levels of Pertuzumab, a Human Epidermal Growth Factor Receptor 2 Dimerization Inhibitor, in Patients with Human Epidermal Growth Factor Receptor 2-Negative Metastatic Breast Cancer," Journal of Clinical Oncology, vol. 28(7)1131-1137 (2010).
Gil-Ad, I. et al., "Insulin-like-growth-factor-I (IGF-I) antagonizes apoptosis induced by serum deficiency and doxorubicin in neuronal cell culture," Growth Hormone & IGF Research, vol. 9: 458-464 (1999).
Guerra, Y., et al., "Lack of efficacy of adjuvant lapatinib in HER2-negative breast cancer (HER2-ve BC): Analysis of patients in the TEACH trial," 2013 ASCO Annual Meeting: Abstracts: Meeting Library, J. Clin. Oncol, vol. 31(Abstract 628), 2 pages,(2013). Retrieved from the Internet: URL:http://meetinglibrary.asco.org/content/115932-132[retrieved on Feb. 23, 2016].
Hassan, S. et al., "Model for Time Dependency of Cytotoxic Effect of CHS 828 in Vitro Suggests Two Different Mechanisms of Action," The Journal of Pharmacology and Experimental Therapeutics, vol. 299(3):1140-1147 (2001).
Hermanto U. et al., "ErbB2-overexpressing human mammary carcinoma cells display an increased requirement for the phosphatidylinositol 3-kinase signaling pathway in anchorage-independent growth", Oncogene, vol. 20(51):7551-7562 (2001).
Holt, R.U. et al., "Human myeloma cells adhere to fibronectin in response to hepatocyte growth factor," Haematologica/The Hematology Journal, vol. 90(4):479-488. (2005).
Huang, Y et al., "A functional signal profiling test for identifying a subset of HER2-negative breast cancers with abnormally amplified HER2 signaling activity," OncoTarget, vol. 7(48):78577-78590 (2016) XP055474584, DOI: 10.18632/oncotarget.12480.
Huang, Y., et al., "Development of a test that measures real-time HER2 signaling function in live breast cancer cell lines and primary cells," BMC Cancer, vol. 17 (199):18 pages (2017) , XP055474590, DOI: 10.1186/s12885-017-3181-0.
Hynes, R., "Integrins: Bidirectional, Allosteric Signaling Machines," Cell, vol. 110:673-687 (2002).
International Preliminary Report on Patentability, PCT/US2013/045338, dated Dec. 16, 2014, 8 pages.
International Preliminary Report on Patentability, PCT/US2015/065584, dated Jun. 13, 2017, 10 pages.
International Preliminary Report on Patentability, PCTUS2014/069980, dated Jun. 14, 2016, 10 pages.
International Search Report and Written Opinion for Application No. PCT/US2013/045338, 13 pages, dated Aug. 5, 2013.
International Search Report and Written Opinion, PCT/2015/065584, dated Mar. 7, 2016, 15 pages.
International Search Report and Written Opinion, PCT/US2018/022936, dated Jul. 19, 2018, 25 pages.
International Search Report and Written Opinion, PCTUS2014/069980, dated Jun. 26, 2015, 18 pages.
Invitation to Pay Additional Fees and, Where Applicable, Protest Fee, PCT/US2018/022936, dated May 24, 2018, 16 pages.
Jonker, DJ et al., "Cetuximab for the treatment of colorectal cancer," New England J of Med., vol. 357(20):2040-2048 (2007).
Kepp, O. et al., "Cell death assays for drug discovery," Nature Reviews, vol. 10: 221-237 (2011).
Kleinhans, R. et al., "Sensor-based cell and tissue screening for personalized cancer chemotherapy," Med Biol Eng Comput, vol. 50(2):117-126 (2012).
Konya, V. et al., "Endothelial E-type Prostanoid 4 Receptors Promote Barrier Function and Inhibit Neutrophil Trafficking," J. Allergy Clin. Immunol., vol. 131(2), No. 2:532-540 (2013).
Laing L., "The Pulse of Label Free Indicates the Technology is Alive and Beating," Drug Discovery, vol. 5: 24-30 (Oct./Nov. 2010).
Levasseur, L. et al., "Modeling of the Time-Dependency of in Vitro Drug Cytotoxicity and Resistance," Cancer Research, vol. 58(24):5749-5761 (1998).
Liu Q. et al., "Impedance studies of bio-behavior and chemosensitivity of cancer cells by micro-electrode arrays," Biosensors and Bioelctronics, Elsevier BV, NL, vol. 24 (5):1305-1310 (2009).
Loum, E. et al., "Oncogramme, a new individualized tumor response testing method: application to colon cancer," Cytotechnology, vol. 62:381-388 (2010).

(56) References Cited

OTHER PUBLICATIONS

Matsuo, T. et al., "Analysis of the anti-tumor effect of cetuximab using protein kinetics and mouse xenograft models," BMC Research Notes, vol. 4(140):1-8.(2011).

McGuinness, R. et al., "Impedance-based cellular assay technologies: recent advances, future promise," Current Opinion in Pharmacology, vol. 7(5):535-540 (2007).

Mestres, P. et al., "The Bionas technology for anticancer drug screening," Expert Opinion Drug Discovery, vol. 4(7):785-797 (2009).

Moasser, M. et al., "The oncogene HER2; Its signaling and transforming functions and its role in human cancer pathogenesis," Oncogene, vol. 26(45): 6469-6487(2007).

Morrison, S. et al., "Chimeric human antibody molecules: Mouse antigen-binding domains with human constant region domains," Proc. Natl. Acad. Sci. USA, vol. 81:6851-6855 (1984).

Muise-Helmericks, R. et al., "Cyclin D Expression Is Controlled Post-transcriptionally via a Phosphatidylinositol 3-Kinase/Akt-dependent Pathway," The Journal of Biological Chemistry, vol. 273 (45):Issue of Nov. 6, 29864-29872 (1998).

Ochs, R. et al., "The ChemoFx.® Assay an Ex Vivo Cell Culture Assay for Predicting Anticancer Drug Responses," Methods in Molecular Medicine, vol. 110: Chemosensitivity: vol. 1: In Vitro Assays:155-172 (2005).

Otto, A. et al., "Microphysiological testing for chemosensitivity of living tumor cells with multiparametric microsensor chips," Cancer Detection and Prevention, vol. 27:291-296 (2003).

Otto, A. et al., "Multiparametric Sensor Chips for Chemosensitivity Testing of Sensitive and Resistant Tumor Cells," Recent Results in Cancer Research, vol. 161:39-47 (2003).

Extended European Search Report, European Application No. 19180662.9, dated Dec. 9, 2019, 10 pages.

International Preliminary Report on Patentability, PCT/US2018/022936, dated Sep. 24, 2019, 14 pages.

Menendez, J.A., et al., Trastuzumab in Combination With Heregulin-Activated Her-2 (erbB-2) Triggers a Receptor-Enhanced Chemosensitivity Effect in the Absence of Her-2 Overexpression, Journal of Clinical Oncology, vol. 24:3735-3746 (2006).

Montero, J. et al., "P-Rex1 participates in Neuregulin-ErbB signal transduction and its expression correlates with patient outcome in breast cancer," Oncogene, vol. 30(9):1059-1071 (2011).

Singer F. C. et al., "Predicting the efficacy of trastuzumab-based therapy in breast cancer: Current standards and future strategies," Biochimica et Biophysica Acta Reviews on Cancer, vol. 1786:105-113 (2008).

Tan, M. et al., "Heregulin beta1-activated phosphatidylinositol 3-kinase enhances aggregation of MCF-7 breast cancer cells independent of extracellular signal-regulated kinase," Cancer Res., vol. 59(7):1620-1625 (1999).

Unger F. et al., "Prediction of Individual Response to Anticancer Therapy: Historical and Future Perspectives," Cell Mol. Life Science, vol. 72:729-757 (2015).

Yuste, L. et al., "Activation of ErbB2 by Overexpression or by Transmembrane Neuregulin Results in Differential Signaling and Sensitivity to Herceptin," Cancer Res., vol. 65 (15): 6801-6810 (2005).

Zhao W. et al, "Neuregulin 1 enhances cell adhesion molecule L1 expression in human glioma cells and promotes their migration as a function of malignancy," J Neuropathol Exp Neurol., vol. 72(3):244-255 (2013).

Extended European Search Report, European Application No. 20152262.0, dated Jul. 1, 2020, 15 pages.

Howe, L. et al., "Targeting the HER/EGFR/ErbB Family to Prevent Breast Cancer," Cancer Prev Res., vol. 4(8):1149-1157 (2011).

Kwak, E. et al., "The Role of Irreversible Her Family Inhibition in the Treatment of Patients with Non-Small Cell Lung Cancer," The Oncologist,vol. 16:1498-1507 (2011).

Lee, Cy et al., "Neuregulin autocrine signaling promotes self-renewal of breast tumor-initiating cells by triggering HER2/HER3 activation," Cancer Res., vol. 74(1):341-52 (2014).

Lu, C. et al., "Effect of Epidermal Growth Factor Receptor Inhibitor on Development of Estrogen Receptor-Negative Mammary Tumors," Journal of the National Cancer Institute, vol. 95(24):1825-1833 (2003).

Shamah, S. et all., "Label-free cell-based assays using photonic crystal optical biosensors," Analyst, vol. 136:1090-1102 (2011).

U.S. Appl. No. 15/533,897, dated Oct. 15, 2020.

\* cited by examiner

| Reference Standard | Celcuity Test | | Total |
|---|---|---|---|
| (clinical response) | Response | Non-Response | |
| Non-response | 0 | 1 | 1 |
| Response | 3 | 0 | 3 |
| Total | 3 | 1 | 4 |

Third Party Measured Clinical Response vs. Celcuity Test Prediction - B1 and B4 cells with Trastuzumab or Lapatinib

FIG. 1C

| Reference Standard | Celcuity Test | | Total |
|---|---|---|---|
| (clinical response) | Response | Non-Response | |
| Non-response | 0 | 0 | 0 |
| Response | 2 | 0 | 2 |
| Total | 2 | 0 | 2 |

Third Party Measured Clinical Response vs. Celcuity Test Prediction - B1 and B2 cells with Paclitaxel

FIG. 2C

| Reference Standard (clinical response) | Celcuity Test | | Total |
|---|---|---|---|
| | Response | Non-Response | |
| Non-response | 0 | 0 | 0 |
| Response | 2 | 0 | 2 |
| Total | 2 | 0 | 2 |

Third Party Measured Clinical Response vs. Celcuity Test Prediction – C1 and C2 cells tested in Combination with Cetuximab and Irinotecan

| Third Party Measured Clinical Response vs. Celcuity Test Prediction - All Patients Cells from Examples 1-4 | | | |
|---|---|---|---|
| Reference Standard (clinical response) | Celcuity Test Response | Non-Response | Total |
| Non-response | 0 | 4 | 4 |
| Response | 60 | 1 | 61 |
| Total | 60 | 5 | 65 |

FIG. 8A

| Third Party Measured Clinical response vs. Celcuity Test Prediction - Breast Cancer Cells Tested in Examples 1-4 | | | |
|---|---|---|---|
| *Breast Cancer Cells tested with capecitabine, cetuximab, docetaxel, fluorouracil, gefitinib, GSK1059615, GSK1120212, lapatinib, paclitaxel, pazopanib, trastuzumab, topotecan, and trastuzumab/lapatinib* | | | |
| Reference Standard (clinical response) | Celcuity Test Response | Non-Response | Total |
| Non-response | 0 | 3 | 3 |
| Response | 47 | 1 | 48 |
| Total | 47 | 4 | 51 |

FIG. 8B

| Third Party Measured Clinical response vs. Celcuity Test Prediction - Colon Cancer Cells Tested in Examples 1-4 | | | |
|---|---|---|---|
| *Colon Cancer Cells tested with cetuximab, irinotecan, oxiliplatin, and cetuximab/irinotecan* | | | |
| Reference Standard (clinical response) | Celcuity Test Response | Non-Response | Total |
| Non-response | 0 | 1 | 1 |
| Response | 7 | 0 | 7 |
| Total | 7 | 1 | 8 |

FIG. 8C

| Third Party Measured Clinical response vs. Celcuity Test Prediction - Lung Cancer Cells Tested in Examples 1-4 | | | |
|---|---|---|---|
| *Lung Cancer Cells tested with cisplatin, erlotinib, paclitaxel/cisplatin* | | | |
| Reference Standard (clinical response) | Celcuity Test Response | Non-Response | Total |
| Non-response | 0 | 0 | 0 |
| Response | 6 | 0 | 6 |
| Total | 6 | 0 | 6 |

FIG. 8D

Test Sensitivity and Specificity for all 65 CELx Test
Results described in Examples 1-4

|  | Sensitivity | Specificity | No. |
|---|---|---|---|
| Total | 98% | 100% | 65 |
| Disease | | | |
| Breast | 98% | 100% | 51 |
| Lung | 100% | 100% | 6 |
| Colon | 100% | 100% | 8 |
| Drug Type | | | |
| Pathway | 97% | 100% | 34 |
| Anti-proliferative | 100% | 100% | 23 |
| Combination | 100% | 100% | 8 |
| Drug | | | |
| Capecitabine | 100% | 100% | 1 |
| Cetuximab | 100% | 100% | 2 |
| Cisplatin | 100% | 100% | 2 |
| Docetaxel | 100% | 100% | 6 |
| Erlotinib | 100% | 100% | 2 |
| Fluorouracil | 100% | 100% | 5 |
| Gefitinib | 50% | 100% | 3 |
| GSK1059615 | 100% | 100% | 4 |
| GSK1120212 | 100% | 100% | 6 |
| Irinotecan | 100% | 100% | 2 |
| Lapatinib | 100% | 100% | 7 |
| Oxiliplatin | 100% | 100% | 2 |
| Paclitaxel | 100% | 100% | 4 |
| Pazopanib | 100% | 100% | 6 |
| Topotecan | 100% | 100% | 1 |
| Trastuzumab | 100% | 100% | 4 |
| Cetuximab/Irionotecan | 100% | 100% | 2 |
| Paclitaxel/Cisplatin | 100% | 100% | 2 |
| Trastuzumab/Lapatinib | 100% | 100% | 4 |
| Pathway | | | |
| AKT | 95% | 100% | 20 |
| Apoptotic pathways | 100% | 100% | 23 |
| Cell Adhesion | 97% | 100% | 65 |
| FAK1 | 95% | 100% | 20 |
| MAK | 100% | 100% | 6 |
| MAPK | 95% | 100% | 20 |
| MEK/MAPK | 100% | 100% | 6 |
| MKK | 100% | 100% | 6 |
| PI3K/PTEN | 96% | 100% | 26 |
| RAS/RAF | 96% | 100% | 26 |
| RHO | 95% | 100% | 20 |

FIG. 9

WHOLE CELL ASSAYS AND METHODS

CROSS REFERENCE TO RELATED APPLICATIONS

This application is a continuation of U.S. application Ser. No. 15/192,280, filed Jun. 24, 2016, which is a continuation of U.S. application Ser. No. 14/590,731, filed Jan. 6, 2015, which is a continuation of U.S. application Ser. No. 13/494,618, filed Jun. 12, 2012. The contents of the aforementioned applications are hereby incorporated herein by reference.

BACKGROUND

Treatment of diseased individuals has made significant progress since the discovery that chemicals and exogenous proteins can be effective human therapeutic agents against specific cellular targets. However, there is still significant room for improvement in the treatment of many common diseases such as cancer. One of the main drivers of the Human Genome Project was to discover the genetic causes of diseases, in order to advance the development and prescription of therapeutic intervention. If reports are to be believed, all human genes have been identified through the Human Genome Project. Many of these genes have been statistically linked to disease in human populations. Yet knowledge of the genetic links of a disease or detection of genetic biomarkers does not always effectively predict disease course or therapeutic outcome. So too have the genetic links and even the quantification of protein expression levels from those genes been very limited in determining appropriate therapeutic courses.

Petabyte amounts of genetic information have been collected. A great deal of statistical and analytical modeling computing power has been applied to the genetic data collected to analyze many different types of diseases. At least two important facts have emerged from this process. First, a "disease" like breast cancer is heterogeneous in part because breast cancer in one individual can be completely different from the same cancer in another individual in genetic makeup, protein expression levels, and response to therapeutic intervention. Second, detection of current genetic biomarkers has poor predictive value in the majority of cases.

Contemporary targeted drugs are discovered and developed along a process with specific limited number of human cell models in mind. Many of these cell lines are engineered to provide for optimized screening environments of large libraries of potential drugs to select those with desired activity against a particular cellular target. Employment of this process can be misleading as to the efficacy of potential drugs in light of clinical information indicating that each patient's disease is different from other patients with the same disease. The drug discovery and development process to date is not very effective at identifying responsive humans prior to clinical trials and continues to suffer a high failure rate throughout the clinical development process. Many of the drugs that are approved through the regulatory clinical development process that focuses on reducing harm to patients suffer from poor efficacy rates in actual disease patient populations.

Not all disease condition presentations to the clinical physician arise from the same cause. In a simple example, inflammation of bone joints can arise from several sources, some internal, some external, some "genetically linked," and some with yet unknown causes. The medical sciences are fairly effective in triaging patients for infectious diseases when the external pathogen can be identified properly. Physicians have fewer tools at hand for predicting which of the therapies that are currently available will lead to reduction of inflammation from internal causes. Physicians lack the knowledge of how a specific patient's cells are functioning, or more appropriately malfunctioning, and how they will respond to one of the many therapeutics that are available for treating the disease that presents clinically as "inflammation." They may know that an aberrant gene is present but do not know how that affects the disease course in a specific patient. They may know specifically how a drug is supposed to act but not why a particular patient may be unresponsive or resistant to that drug activity.

Patients need better identification of their particular disease cause and better informed decision-making for an effective therapeutic course. Human genome sequencing and other genetic quantification tools have informed doctors that each patient's disease is somewhat unique to that patient. This information has spawned a whole business around personalized medicine, where each patient could potentially receive a customized therapeutic regimen customized for their disease. Drugs are being developed for specific gene-related disease indications. This ideal approach has yet to be validated due primarily to significant shortcomings of the current prognostic toolset. The genes may be present but their function in the context of a particular individual is not correlated.

One response to the realization that each patient is different and that many times therapies fail to effect a positive response, has been the development of companion diagnostics. This type of diagnostic test is designed using contemporary biomarker detection tools to try to identify those patients that are more likely to respond to a particular drug. The test involves looking for increased gene number, gene mutation, or altered expression level of a particular gene. Success rates for most of these tests at predicting significant therapeutic response are often much less than 50%.

Thus there remains a need to provide better prognostic indicators for the effectiveness of therapeutics for an individual.

SUMMARY OF THE INVENTION

Some drugs are being targeted for specific gene-related disease indications. This approach has not yet been broadly utilized due primarily to significant shortcomings of the current prognostic toolset. The kits and methods as described herein provide for a method of selecting a therapeutic agent that shows efficacy against an individual's disease. In embodiments, the therapeutic agent is contacted to label free live whole cells from diseased tissue in a CReMS and a change or lack thereof in a physiologic parameter of the cells is detected in the presence of the therapeutic agent. A therapeutic agent is selected to treat the subject that results in a change in a physiological parameter of the disease cell as compared to a baseline measurement.

One aspect of the disclosure includes methods of selecting one or more therapeutic agents either at the initial diagnosis or throughout treatment. In embodiments, a method for selecting one or more therapeutic agents that are approved for use to treat a disease or disorder in an individual subject comprises administering one or more therapeutic agents to at least one isolated disease cell sample from the subject in a cellular response measurement system; determining whether a change occurs in cellular response parameter of the disease cell sample in response to the therapeutic agent or agents as compared to a baseline measurement of the cellular response parameter before administration of the therapeutic agent or agents, wherein the change in cellular response parameter indicates that the agent or agents has therapeutic efficacy for the disease in the individual subject. In embodiments, the isolated disease cell sample comprises label free whole cells. In embodiments, the change of the cellular response parameter in the isolated disease cell is monitored continuously for a defined period of time. In embodiments, the method further comprises selecting the therapeutic agent or combination of therapeutic agents that results in the change of at least one cellular response or physiologic parameter and communicating the selected agent to a health care provider. In embodiments, the method further comprises administering the therapeutic agent or combination of therapeutic agents that results in the change of at least one cellular response or physiologic parameter to the subject.

In embodiments, a method for selecting a treatment for an individual subject comprises determining therapeutic efficacy of an agent for a disease in the individual subject comprising: administering the agent to at least one isolated label free disease cell sample from the individual subject in a cellular response measurement system (CReMS), wherein the disease cell sample is selected from the group consisting of a cancer cell sample, a cell sample from a subject with an autoimmune disease, a cell sample from a tissue infected with a foreign agent and combinations thereof; continuously measuring a change in at least one physiological response parameter of the cell sample for a defined period of time in the presence of the therapeutic agent; and determining whether a change in a physiological response parameter of the cell sample to the agent occurs as compared to a baseline measurement, wherein the change in physiological response indicates that the agent has therapeutic efficacy for the disease in the individual subject.

In embodiments, a method for selecting a treatment for an individual subject having cancer comprises determining therapeutic efficacy of an agent for cancer in the individual subject comprising: administering the agent to at least one isolated label free cancer cell sample from the individual subject in a biosensor; continuously measuring a change in at least one physiological response parameter of the cell sample for a defined period of time in the presence of the therapeutic agent; and selecting the therapeutic agent for treatment of the subject that exhibits a change in a physiological response parameter of the cell sample as compared to a baseline measurement.

In another aspect of the disclosure, a kit comprises: a container for a disease cell sample from an individual subject containing a transport medium; a container for a control cell sample from the individual subject containing a transport medium; a biosensor; and a non-transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, 02, $CO_2$, glucose, and combinations thereof; classifying the output as no response, weakly responsive, and responsive; and generating a report with the classification.

BRIEF DESCRIPTION OF THE FIGURES

FIGS. 1A, 1B, and 1C show the results of a "CELx" test performed with cells from two HER2 overexpressing breast cancer patients (Patient B1 and B4), two targeted pathway drugs (Lapatinib and Trastuzumab) that are indicated for HER2 positive breast cancers, and human epidermal growth factor (EGF). The physiologic change of the B1 and B4 cells during the test was measured with a cellular response measurement system (CReMS) and the output from the CReMS is what is recorded in the figure. One sample each of B1 and B4 cells was pre-treated with Lapatinib and another sample each of B1 and B4 cells was pre-treated with Trastuzumab and the physiologic response of each set of cells to subsequent EGF stimulation is recorded on a continuous basis throughout the test. The CELx Pathway Shutdown test shown in FIG. 1A predicts that Patient B1 will not respond to trastuzumab but will respond to Lapatinib. The results shown in FIG. 1B also predict that Patient B4 would respond to both trastuzumab and lapatinib. The comparison of the CELx test prediction and the result recorded by third party clinical reference is shown in FIG. 1C; it shows that the CELx test accurately predicted the results recorded by the clinical reference standard, where Patient B1 was found unresponsive to trastuzumab and responsive to lapatinib and Patient B4 was found responsive to both.

FIGS. 2A, 2B, and 2C show the results of a CELx test performed with cells from two breast cancer patients (Patients B1 and B2) and the anti-proliferative drug Paclitaxel. The physiologic change of the B1and B2 cells during the test was measured with a CReMS and the output from the CReMS is what is recorded in the figure. One set each of the B1 and B2 cells were treated with Paclitaxel and another control set of B1 and B2 cells received no drug; the physiological response of each set of cells was recorded continuously over the course of 48 hours. The B2 test cells showed initial responsiveness to Paclitaxel, as reflected in the significant decrease in CReM output compared to the B2 control cells, but after roughly 24 hours, the CReM output reverses, indicating that the test cells begin proliferating and are no longer responsive to the drug. The B1 test cells show immediate and continuous responsiveness to Paclitaxel, as reflected in the decrease in CReM output compared to the B1 control cells throughout the test period. The CELx test results presented in FIGS. 2A and 2B predict that both patients B1 and B2 will respond to paclitaxel. The comparison of the CELx test prediction and the result recorded by third party clinical reference is shown in FIG. 2C; it shows that the CELx test accurately predicted the results recorded by the clinical reference standard, where Patients B1 and B2 were both found responsive to paclitaxel.

FIGS. 3A, 3B, and 3C show the results over the entire time course of the experiment of a CELx test performed with cells from two colon cancer patients (Patients C1 and C2), EGF, and a combination of two drugs indicated for colon cancer, cetuximab and irinotecan. The physiologic change of the C1 and C2 cells during the test was measured with a CReMS and the output from the CReMS is what is recorded in the figure. One set each of C1 and C2 test cells were treated with Cetuximab and Irinotecan and another set of control C1 and C2 cells received no drug; the physiological response of each set of cells was recorded continuously. Both the C1 and C2 test cells showed responsiveness to the drug combination as reflected in the reduced CReMS output for the test cells compared to their respective control cells. These results predict that both patients C1 and C2 will respond to the combination of cetuximab and irinotecan. The comparison of the CELx test prediction and the result recorded by third party clinical reference is shown in FIG. 3C; it shows that the CELx test accurately predicted the results recorded by the clinical reference standard, where Patients C1 and C2 were both found responsive to the cetuximab and irinotecan combination.

FIG. 4 also shows the results from two CELx Combination tests performed using the drug combination of paclitaxel and cisplatin on Patient L1 and L2 cells and four CELx tests with the drug combination of trastuzumab and lapatinib on Patient B1, B2, B3, and B4 cells. A total of sixteen different drugs that target 11 different cellular pathways were introduced to cell samples in this set of experiments. For each experiment, the change of the test cells' physiologic response compared to its control cells was calculated. Each box in FIG. 4 classifies the change in physiologic response measured in each experiment as either being greater than 50% (solid box), between 5%-50%, (vertical shaded box), less than 5% (horizontal shaded box), or not tested (open box). The series of experiments represented in this figure illustrate the CELx test's ability to measure the physiologic change that occurs in a variety of cancer cell types after they are exposed to wide range of drugs.

FIG. 7 records the correlation (either 0% or 100%) between the CELx test predictions described in FIG. 6 (test cell response to individual drugs) and results from third parties that recorded the patient's responsiveness to the drug. The solid boxes represent 100% concordance between test results on the cell sample for response or nonresponse to the therapeutic agent and the known status of the cell sample, a blank box is not tested, and a gray shaded box represents no concordance with the known cell sample status for response or non response to the therapeutic agent. In tested cases, the CELx test and the third parties generated the same result except in one case, illustrating the power of the CELx test to predict breast, lung, and colon patient response to 16 different drugs that target a wide range of cellular pathways.

FIGS. 8A, 8B, 8C and 8D record the CELx test results for different patient cancer cells and drugs versus results from third parties that recorded the patient's responsiveness to the drug. FIG. 8A records the comparison of results for all 12 cancer patient cells and 16 different drugs that were tested. FIG. 8B records the comparison of results for the eight breast cancer patient cells that were tested singly and in combination with thirteen different drugs. FIG. 8C records the comparison of results for the two different colon cancer patient cells that were tested singly and in combination with three different drugs. FIG. 8D records the comparison of results for the two different lung cancer patient cells that were tested singly and in combination with three different drugs. In each Figure, the CELx tests are shown to predict accurately whether a patient will or will not respond to a particular drug or combination of drugs except in one case.

FIG. 9 records the sensitivity and specificity of the CELx test for all the patient cells and drug tested as well as for the sub-groups of patients, drugs, pathways, and CReMS types tested. Overall and within each of the sub-groups studied, the CELx test generated high sensitivity (98%+) and specificity (99.9%+). These results illustrate the predictive power of the test across different cancer cell types, drug types, CReMS types, and pathways targeted.

DETAILED DESCRIPTION

A. Definitions

Figure 1A:
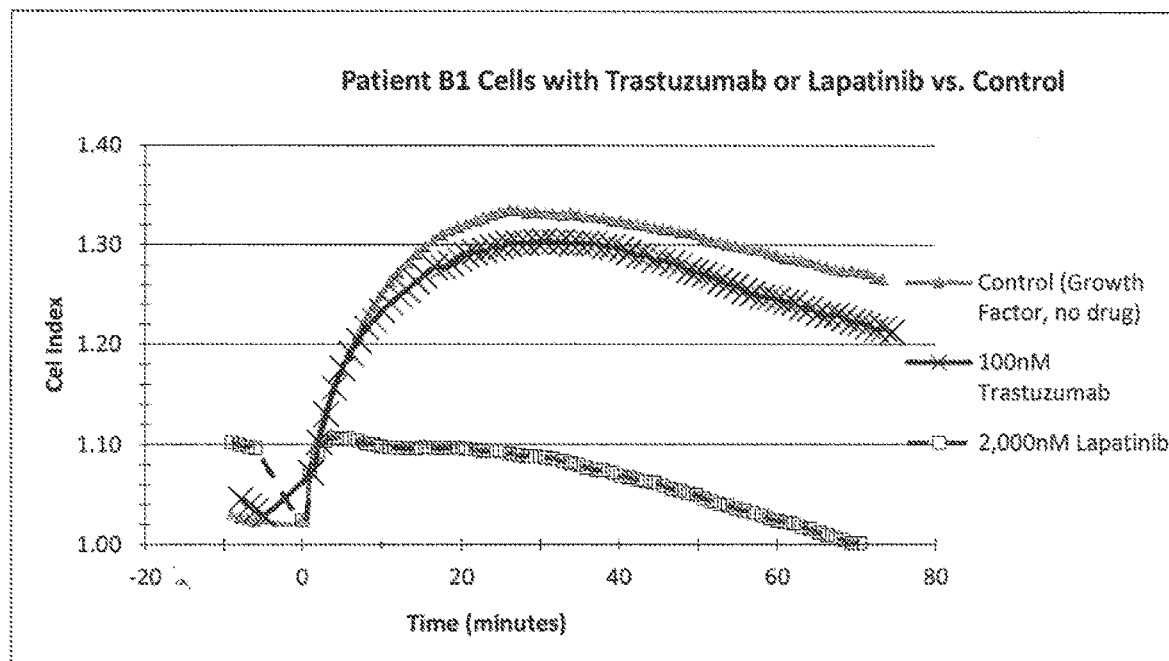

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference. The following terms, as used herein, are intended to have the following definitions.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5).

The term "activator," "activate," or "perturbant," "perturb," "perturbation" in conjunction with respect to cells refer to the specific subject or activity of physiologic manipulation of a cell using reagents, organic molecules, signaling factors, biochemicals, nucleic acids, or proteins that have an effect on cells well known to those practiced in the art. The effect refers to any modulation of cellular physiologic activity and may include but not be limited to up or down-regulation.

The term "assay" or "assaying" refers to an analysis to determine, for example, the presence, absence, quantity, extent, kinetics, dynamics, or type of a target, such as a cell's optical or bioimpedance response upon stimulation with exogenous stimuli (e.g., therapeutic agent).

The terms "attach," or "attachment," refer to, for example, a surface modifier substance, a cell, a ligand candidate compound, and like entities of the disclosure, connected to a surface, such as by physical absorption, chemical bonding, chemical attraction, and like processes, or combinations thereof. Particularly, "cell attachment," "cell adhesion," or "cell sample attachment" refer to the binding of cells together or interacting to a surface, such as by culturing, or interacting with a cell anchoring material, or the like.

The term "attachment pattern" refers to observable traits or characteristics of a cell or cell sample's connection to a surface. An attachment pattern can be quantitative, e.g., number of attachment sites. An attachment pattern can also be qualitative, e.g., preferred molecular site of attachment to an extracellular matrix.

The term "antibody" is used in the broadest sense and specifically includes monoclonal antibodies (including full length monoclonal antibodies), humanized antibodies, chimeric antibodies, multispecific antibodies (e.g., bispecific antibodies), and antibody fragments that exhibit a desired biological activity or function.

Antibodies can be chimeric, humanized, or human, for example, and can be antigen-binding fragments of these. "Antibody fragments" comprise a portion of a full-length antibody, generally the antigen binding or variable region thereof. Examples of antibody fragments include Fab, Fab', F(ab)$_2$, and Fv fragments; diabodies; linear antibodies; single-chain antibody molecules; and multispecific antibodies such as bispecific antibodies, for example formed from antibody fragments. "Functional fragments" substantially retain binding to an antigen of the full-length antibody, and retain a biological activity. Antibodies can be "armed" or "conjugated" by combining with one or more other drugs through covalent or other attachment to achieve greater potency, specificity, and efficacy than the individual drug molecules could achieve separately.

The term "monoclonal antibody" as used herein refers to an antibody obtained from a population of substantially homogeneous antibodies, i.e., the individual antibodies of the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

"Chimeric" antibodies (immunoglobulins) contain a portion of a heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., 1984, *Proc. Natl. Acad. Sci. USA* 81:6851-6855).

The term "humanized antibody", as used herein, are antibodies that contain minimal sequence derived from nonhuman immunoglobulin. For the most part, humanized antibodies are human immunoglobulins (recipient or acceptor antibody) in which variable domain hypervariable region residues of the recipient antibody are replaced by hypervariable region residues from a nonhuman species (donor antibody), such as mouse, rat, rabbit, or nonhuman primate having the desired specificity, affinity, and capacity. The hypervariable regions can be complementarity-determining regions (CDRs) defined by sequence (see, for example Kabat 1991, 1987, 1983), or hypervariable loops (HVLs) defined by structure (see for example, Chothia 1987), or both.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens, laminins, other glycoproteins, peptides, glycosaminoglycans, proteoglycans, vitronectin, IntercellularCAMs, VascularCAMs, MAdCAMs), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals. Coatings can also include cell surface receptor or cell surface cognate binding proteins or proteins with affinity for said cell surface proteins.

The term "baseline measurement" refers to a physiologic beginning point for a set of cells to be tested and is based on an evaluation of measurements over a period of time before drug is added. This may include a basal cellular metabolism measurement or CReMS reading prior to exogenous perturbation. This may alternatively include but not be limited to include the CReMS measurement of a normal healthy cell metabolic function with or without exogenous perturbation.

The term "basal morphology" refers to the form and structure of a cell or cell sample prior to the introduction of an agent or stimulus.

The term "cell adhesion" refers to the binding of a cell to another cell, to an extracellular matrix component, or to a surface (e.g., microtiter plate).

The term "Cellular Response Measurement System" or "CReMS" refers to a device that can quantitatively determine a change in a physiological or cellular response parameter in a cell, in and between cells, and between cells and the instrumentation device. In embodiments the cell is a whole label free cell. A change in a physiological or cellular response parameter is measured by determining change in an analyte such as glucose, oxygen, carbon dioxide, amine containing materials such as proteins, amino acids, or of the extracellular matrix, or of a cell signaling molecule, or of cell proliferation, cell morphology, or cytoskeletal rearrangement. An example of a CReMS is a biosensor.

The term "CReMS Signal" as used herein is defined as a measure of cellular physiologic change of cells when those cells are analyzed by a chemo-electric CReMS. The CReMS signal and changes in the CReMS signal can have various units as related to the particular chemo-electric transducer measuring the physiologic change. For example, the CReMS signal may have units of but not be limited to cell index, impedance, wavelength units, pH units, voltage, current, or become dimensionless by using ratios of the units. Any of these units may have a time component. The CReMS signal can be mathematically modified for clarity of interpretation as is frequently done by those practiced in the art of biology, biochemistry and biophysics, for example including normalization, baselining, curve subtracting, or any combination of these. The CReMS signal may be measured at a single time point, or, more preferably, over a continuous series of time points representing a complete pattern of cellular physiologic response.

The term CReM "optical signal" is defined as the wavelength value or change in wavelength value measured as light is reflected from the photonic crystal biosensing CReMS upon which the cells rest. The units are typically in picometers or nanometers though could also become dimensionless if ratios of changes are reported. The "optical signal" could be expressed in said units combined with time. The shift in reflected wavelengths of light is proportional to the mass upon the photonic crystal surface. Thus the "optical signal" is a quantitative measure of the number of cells on the CReMS. Furthermore, the "optical signal" is a measure of the cell physiological status as for example changes in cell morphology, cell adhesion, cell viability, structural rearrangements of the cell lead to differences in the amount of mass upon the sensor that are detected as wavelength shifts.

The term "Cell Index" as used herein is defined as a measurement of impedance and can be applied in one instance of the present invention by measuring at a fixed electrical frequency of, for example, 10 kHz and fixed voltage.

And calculated by the equation Cell Index$_i$=($R_{tn}$−$R_{t0}$)/F

Where:
i=1, 2, or 3 time point
F=15 ohm in one example when the instrument is operated at 10 kHz frequency
$R_{t0}$ is the background resistance measured at time point T0.
$R_{tn}$ is the resistance measured at a time point Tn following cell addition, cell physiologic change, or cell perturbation.

Cell index is a dimensionless parameter derived as a relative change in measured electrical impedance to represent cell status. When cells are not present or are not well-adhered on the electrodes, the CI is zero. Under the same physiological conditions, when more cells are attached on the electrodes, the CI values are larger. CI is therefore a quantitative measure of cell number present in a well. Additionally, change in a cell physiological status, for example cell morphology, cell adhesion, or cell viability will lead to a change in CI.

The term "biosensor" refers to a device that measures an analyte or a change in an analyte or physiologic condition of a cell. In embodiments, the biosensor typically contains three parts: a biological component or element that binds or recognizes the analyte (including non-limiting examples such as extracellular matrix, cell signaling molecule, or cell proliferation, tissue, cells, metabolites, catabolites, biomolecules, ions, oxygen, carbon dioxide, carbohydrates, proteins etc.), a detector element (operating in a physicochemical manner such as optical, piezoelectric, electrochemical, thermometric, or magnetic), and a transducer associated with both components.

The term "optical biosensor" refers to a device that measures fluorescence, absorption, transmittance, density, refractive index, and reflection of light. In embodiments, an optical biosensor can comprise an optical transducer for converting a molecular recognition or molecular stimulation event in a living cell, a pathogen, or combinations thereof into a quantifiable signal. Additionally, embodiments could include a photonic crystal device, an optical waveguide device, and a surface plasmon resonance device.

The term "impedance biosensor" refers to a device that measures complex impedance changes (delta Z, or dZ) of live patient cells where impedance (Z) is related to the ratio of voltage to current as described by Ohm's law (Z=V/I). It is sensitive to the local ionic environment at the electrode interface with the cells and detects these changes as a function of voltage and current fluctuations. Physiologic changes of the cells as a result of normal function or perturbation thereof result in quantifiable changes to the flow of current around the electrodes and influence the magnitude and characteristics of the signal measured. In embodiments, an impedance biosensor can comprise electrodes or an electrical circuit for converting a molecular recognition or molecular stimulation event in a living cell, a pathogen, or combinations thereof into a quantifiable signal. In embodiments, an ISFET biosensor can comprise an ion selective field effect electrical transducer for converting an analyte recognition or cellular stimulation event in a living cell, a pathogen, or combinations thereof into a quantifiable signal. When an analyte concentration in an ISFET biosensor changes, the current in the transistor changes, which creates a quantification signal.

The term "cell signaling" refers to the intracellular or intercellular transfer of information. Cells signaling can be achieved by direct contact between cells or by the release of a substance from one cell that is taken up by another cell. Intercellular signaling can occur via an interaction between two molecules (e.g., a ligand and a receptor). Receptor binding can trigger a cascade of intracellular signaling (e.g., initiation of biochemical changes within the cell or modification of the membrane potential).

The term "cytoskeletal organization" refers to the arrangement of the internal scaffold of a cell. A cell's cytoskeleton comprises filaments that serve to support cytoplasmic or membrane elements and/or intracellular organelles. The cytoskeleton also helps to maintain the shape of a cell.

The term "cell proliferation" refers to an increase in the number of cells as a result of cell growth and cell division.

The term "cell survival" refers to the viability of a cell characterized by the capacity to perform certain functions such as metabolism, growth, movement, reproduction, some form of responsiveness, and adaptability.

The term "efficacy" refers to the extent to which a specific intervention produces a beneficial result. In embodiments, the intervention can be a therapeutic agent, such as a small molecule or an antibody. A beneficial result includes without limitation an inhibition of symptoms, a decrease in cell growth, an in increase in cell killing, a decrease in inflammation, and an increase in immune responsiveness.

An "extracellular matrix component" is a molecule that occurs in the extracellular matrix of an animal. It can be a component of an extracellular matrix from any species and from any tissue type. Non-limiting examples of extracellular matrix components include laminins, collagens, fibronectins, other glycoproteins, peptides, glycosaminoglycans, proteoglycans, etc. Extracellular matrix components can also include growth factors.

The term "global phenotype" refers to a plurality of observable properties of a cell or cell sample as a whole. A global pheonotype may include but not be limited to cell size, cell shape, distinctive protuberances, outgrowths, spreading, attachment foci density, cytoskeletal arrangements, cell proliferation patterns, receptor phagocytosis, or attachment foci number, changes in pH, uptake or efflux of metabolites, signaling proteins and growth factors, oxygen, CO2, glucose, ATP, and ions such as magnesium, calcium, potassium.

The term "event specificity" refers to a physical observation of a specific property of a cell. Such specific properties relate to a specific cellular function, exogenous perturbation, or pathway agonsim/antagonism as part of the intended and/or expected physiological response of the cell to a particular activator or therapeutic agent. Activators and therapeutic agents may be known to be targeted to affect a certain aspect of the cell function such as cytoskeletal structure, or a cellular pathway. The physically observable event is called event specificity because the physically observable event in the cell in the presence of the activator or the therapeutic agent is a reflection of the intended and/or expected effect the activator or therapeutic agent on the cell. For example, the addition of vinblastine to most cell samples on an attachment biosensor type of CReMS produces a profound reduction in signal. Vinblastine is a cellular cytoskeletal scaffolding disrupter. The reduction in signal is a physically observable event of the cell linked specifically to loss of cell shape and attachment caused by the drug action at microtubule molecules.

The term "Impedance" as used herein is defined by a physical law relating voltage and current by the equation: Impedance (ohm)=Voltage (volts)/Current (amperes) or $Z=V/I$.

"Mammal" for purposes of treatment or therapy refers to any animal classified as a mammal, including humans, domestic and farm animals, and zoo, sports, or pet animals, such as dogs, horses, cats, cows, and the like. Preferably, the mammal is human.

The term "microcantilever device", "microcantilever array", or microcantilever apparatus" refers to a type of CREMS instrument comprising at least one cantilever, a flexible beam that may be bar-shaped, V-shaped, or have other shapes, depending on its application. One end of the microcantilever is fixed on a supporting base, another end standing freely. Microcantilevers can measure concentrations using electrical methods to detect phase difference signals that can be matched with natural resonant frequencies (examples as described in U.S. Pat. No. 6,041,642, issued Mar. 28, 2000, which is hereby incorporated by reference) Determining a concentration of a target species using a change in resonant properties of a microcantilever on which a known molecule is disposed, for example, a macromolecular biomolecule such as DNA, RNA, or protein. Deflection is measured using optical and piezoelectric methods.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R', P(O)OR', CO or CH.sub.2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Polypeptide" refers to a peptide or protein containing two or more amino acids linked by peptide bonds, and includes peptides, oligimers, proteins, and the like. Polypeptides can contain natural, modified, or synthetic amino acids. Polypeptides can also be modified naturally, such as by post-translational processing, or chemically, such as amidation, acylation, cross-linking, and the like.

The term "quartz crystal resonators/microbalance" refers to a type of CREMS device that measures mass by measuring the change in frequency of a piezoelectric quartz crystal when it is disturbed by the addition of a small mass such as a virus or any other tiny object intended to be measured. Frequency measurements are easily made to high precision, hence, it is easy to measure small masses.

As used herein, "sample" refers to anything which may contain a moiety to be isolated, manipulated, measured, quantified, detected or analyzed using apparatuses, microplates or methods in the present disclosure. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

The term "cell sample" refers to cells isolated from a particular subject, where the cells are isolated from a subject's biological fluids, excretions, or tissues. Cells isolated from tissue can include tumor cells. Cells isolated from tissue include homogenized tissue, and cellular extracts, and combinations thereof. Cell samples include isolation from, but are not limited to, blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, marrow, or hair.

The term "CELx" test refers generally to the various embodiments of the methods described herein.

The term "disease cell sample" refers to a plurality of cells from the site of disease or cells that have the characteristic of disease.

The term "healthy cell sample" refers to a cell sample wherein the cells do not have or are extracted from a tissue that does not have the disease that is being tested. For example, when a particular subject is being tested for the effects of a therapeutic agent against the subject's breast cancer, non-cancerous cells or cells from non-breast tissue are considered "healthy". The term "healthy cell sample" is not a determination or reflection upon the whole health status of the subject.

The term Analytical "Sensitivity" refers to a test or the detection limit, and is defined as the lowest quantity differentiated from Zero. (e.g. 95% confidence intervals or 2 standard deviations (SD) above the mean of the Zero control are commonly used).

The Term Clinical "Sensitivity" refers to the proportion of subjects with the target condition in whom the test is positive or how often the test is positive when the condition of interest is present. Clinical "Sensitivity" of a test is defined as an estimate of accuracy provided by the calculation: 100%×TP/(TP+FN) where TP is the number of True Positive events for an outcome being tested and FN are the number of False Negatives events, incorrectly determined events as negative.

Clinical "Specificity" refers to the proportion of subjects without the target condition in whom the test is negative or how often the test is negative when the condition of interest is absent. Clinical specificity is estimated by the calculation: 100%×TN/(FP+TN) where TN is the number of True Negative events for an outcome being tested and FP is the number of False Positives, incorrectly determined events as positive.

The term "surface plasmon resonance device" refers to an optical biosensor type of CReMS that measures binding events of biomolecules at a metal surface by detecting changes in the local refractive index.

The term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term encompasses those compounds or chemicals traditionally regarded as drugs, vaccines, and biopharmaceuticals including molecules such as proteins, peptides, hormones, nucleic acids, gene constructs and the like. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Therapeutic agents include, but are not limited to, anticancer therapeutics, antipsychotics, anti-inflammatory agents, and antibiotics.

The term "targeted pathway drug," "pathway drug," or "targeted drug," refers to any molecule or antibody with therapeutic capacity designed to bind to a specific biomolecule (e.g., protein) involved in a disease process, thereby regulating its activity.

The term "anti-proliferative drug," "anti-proliferative agent," or "apoptosis inducing drug," refers to any molecule or antibody with therapeutic capacity that functions to reduce cell division, reduce cell growth, or kill cells. In many cases, the activity of these drugs is directed towards broad classes of biomolecules (eg. DNA intercalation) involved in normal cellular processes and thus the drug may be less discriminant towards cell disease status.

A "variant" of a polypeptide refers to a polypeptide that contains an amino acid sequence that differs from a reference sequence. The reference sequence can be a full-length native polypeptide sequence or any other fragment of a full-length polypeptide sequence. In some embodiments, the reference sequence is a variable domain heavy chain or variable domain light chain consensus sequence. A polypeptide variant generally has at least about 80% amino acid sequence identity with the reference sequence.

B. Methods of Selecting or Monitoring Efficacy of a Therapeutic Agent

A disease like cancer is heterogeneous in part because cancer in one individual can be completely different from the same cancer in another individual in genetic makeup, protein expression levels, and response to therapeutic intervention. Even diseased tissues can vary considerably from one another in gene expression or gene alterations. For example, metastatic tumors may differ from primary tumors. Human genome sequencing and other genetic quantification tools have informed doctors that each patient's disease is somewhat unique to that patient. This information has spawned a whole business around personalized medicine, where each patient could potentially receive a therapeutic regimen customized for their disease.

Some drugs are being targeted for specific gene-related disease indications. This approach has not yet been broadly utilized due primarily to significant shortcomings of the current prognostic toolset. The methods as described herein provide for a method of selecting a therapeutic agent that shows efficacy against an individual's disease. In embodiments, the therapeutic agent is contacted to isolated label free live whole cells from diseased tissue in a CReMS and a change or lack thereof in a physiologic parameter of the cells is detected in the presence of the therapeutic agent. A therapeutic agent is selected to treat the subject that results in a change in a physiological parameter of the disease cell as compared to a baseline measurement.

One aspect of the disclosure includes methods of selecting one or more therapeutic agents either at the initial diagnosis or throughout treatment. In embodiments, a method for selecting one or more therapeutic agents that are approved for use to treat a disease or disorder in an individual subject comprises administering one or more therapeutic agents to at least one isolated disease cell sample from the subject in a cellular response measurement system; determining whether a change occurs in cellular response parameter of the disease cell sample in response to the therapeutic agent or agents as compared to a baseline measurement of the cellular response parameter before administration of the therapeutic agent or agents, wherein the change in cellular response parameter indicates that the agent or agents has therapeutic efficacy for the disease in the individual subject. In embodiments, the isolated disease cell sample comprises label free whole cells. In embodiments, the change of the cellular response parameter in the isolated disease cell is monitored continuously for a defined period of time. In embodiments, the method further comprises selecting the therapeutic agent or combination of therapeutic agents that results in the change of at least one cellular response or physiologic parameter and communicating the selected agent to a health care provider. In embodiments, the method further comprises administering the therapeutic agent or combination of therapeutic agents that results in the change of at least one cellular response or physiologic parameter.

In another embodiments, a method for selecting a treatment for an individual subject comprises determining therapeutic efficacy of an agent for a disease in the individual subject comprising: administering the agent to at least one isolated label free disease cell sample from the individual subject in a cellular response measurement system (CReMS), wherein the disease cell sample is selected from the group consisting of a cancer cell sample, a cell sample from a subject with an autoimmune disease, a cell sample from a tissue infected with a foreign agent and combinations thereof; continuously measuring a change in at least one physiological response parameter of the cell sample for a defined period of time in the presence and/or absence of the therapeutic agent; and determining whether a change in a physiological response parameter of the cell sample to the agent occurs as compared to a baseline measurement, wherein the change in physiological response indicates that the agent has therapeutic efficacy for the disease in the individual subject. In embodiments, the disease cells are cancer cells.

In other embodiments, a method for comparing efficacy of therapeutic agents for a particular subject comprises administering at least two different therapeutic agents to separate disease cell samples from the same subject in a device that measures at least one physiological parameter of a cell; determining the physiologic response of each cell sample to each of the therapeutic agents compared to a baseline measurement, wherein the physiologic response indicates efficacy of each therapeutic agent. In embodiments, the isolated disease cell sample comprises label free whole cells. In embodiments, the change of the cellular response parameter in the isolated disease cell is monitored continuously for a defined period of time. In embodiments, the method further comprises selecting the therapeutic agent or combination of therapeutic agents that results in better efficacy; and communicating the selection to a health care provider. In embodiments, the method further comprises administering the therapeutic agent or combination of therapeutic agents that results in the better efficacy to the subject.

Another aspect of the disclosure provides a method to determine the growth rate of tumor cells. By measuring the growth rate of tumors, a treatment can be selected depending on how fast the tumor cells can grow. If the tumor cells are a fast growing tumor, the health care worker would select a more aggressive treatment as compared to that of a treatment for a slower growing tumor. In embodiments, a method comprises providing an isolated tumor cell sample in a cellular response measurement system, monitoring the growth rate of the tumor cell sample continuously over a defined period of time, and selecting a more aggressive treatment for those tumor cells that exhibit a fast growth rate and/or communicating the selected treatment to a health care provider. In embodiments, the isolated disease cell sample comprises label free whole cells. In embodiments, the method further comprises administering the selected treatment to the subject. In embodiments, a fast growing tumor has a cell doubling rate of less than about 100 hours, preferably less than 20 hours, whereas a slower growing tumor has a cell doubling rate that is 100 hours or more, where the cell doubling rate is the time for one cell to divide into two cells.

In another aspect of the disclosure, provides a method for determining whether a particular pathway is active in a disease cell sample from an individual subject, and or whether the particular pathway is sensitive to a therapeutic agent to detect the presence of the pathway in the disease cell sample. In such methods, a profile of cellular pathways functioning in the disease cell sample of the individual can be obtained and monitored over time as treatment continues. In embodiments, a method for characterizing a disease cell sample for the presence or absence of a pathway comprises administering one or more activator agents and/or therapeutic agent to at least one isolated disease cell sample from the subject in a cellular response measurement system; determining whether a change occurs in cellular response parameter of the disease cell sample in response to the activator agent and/or therapeutic agent as compared to a baseline measurement of the cellular response parameter before administration of the activator agent and/or therapeutic agent, wherein the change in cellular response parameter indicates that the cellular pathway activated by the activator agent or inhibited by the therapeutic agent is functioning in the isolated disease cell sample from the individual subject. In embodiments, the activator agents include growth factors, protein or other ligands that bind to receptors and cell surface proteins such as heregulin that then activate cellular pathways, cells including transformed cells that have cell surface receptors that activate pathways in a disease cell sample, or small organic molecules (10,000 Daltons or less), peptides, nucleic acids (eg. interfering RNA) that intracellularly perturb cellular physiologic function in a desired manner. In embodiments, the therapeutic agents include from a non-limiting list those that inhibit growth factor receptors such as EGFR, Her2, PDGFR, TGFR, FGFR, TNFR, or VEGF receptors, topoisomerase activity, kinases, G-protein coupled receptors, receptor tyrosine kinases, microtubule polymerization, cytoskeletal organization, cell function and cell adhesion.

In embodiments, a method comprises administering one or more activator agents to an isolated disease cell sample from the subject in a cellular response measurement system; determining whether a change occurs in cellular response parameter of the disease cell sample in response to the activator agent over a defined period of time as compared to a baseline measurement of the cellular response parameter before administration of the activator agent, administering one or more therapeutic agents to the isolated disease cell sample and determining whether a change occurs in cellular response parameter of the disease cell sample in response to the therapeutic agent over a defined period of time as compared to the cellular response parameter before or after administration of the activator agent, wherein the change in cellular response parameter indicates that the cellular pathway activated by the activator agent and inhibited by the therapeutic agent is functioning in the isolated disease cell sample from the individual subject.

Additional embodiments include a method for selecting a subject for a treatment, a clinical trial, and/or evaluating the responsiveness of patients to a candidate therapeutic agent. In embodiments, the subject is selected prior to the clinical trial of that candidate therapeutic in order to select only those patients who are most likely to respond to the candidate therapeutic; this approach would increase the likelihood that the candidate therapeutic could demonstrate efficacy within the selected patient population sufficient to warrant regulatory approval, particularly with therapeutic agents that can only provide an efficacious result for a portion of the overall population that is diagnosed with that disease. Patients considered for a clinical trial of an unapproved therapeutic under this approach would have their diseased cells evaluated to determine their responsiveness to the drug. Only those that demonstrate responsiveness to the unapproved therapeutic agent would get selected for the trial. In other embodiments, a subject is selected for a treatment when a sample of the subject's cells is identified as a responder by a method comprising administering one or more therapeutic agents to at least one isolated disease cell sample from the subject in a cellular response measurement system; determining whether a change occurs in cellular response parameter of the disease cell sample in response to the therapeutic agent or agents as compared to a baseline measurement of the cellular response parameter before administration of the therapeutic agent or agents, wherein the change in cellular response parameter indicates that the agent or agents has therapeutic efficacy for the disease in the individual subject. In embodiments, a method further comprises selecting the subject whose cells exhibit a change in a cellular response parameter in response to the therapeutic agent or agents for treatment or for a clinical trial.

A further aspect includes a method to identify biomarkers of disease sample from a subject that demonstrates responsiveness or non responsiveness to a therapeutic agent. In embodiments, a method involves contacting an isolated disease cell sample from a subject with a therapeutic agent in a cellular response measurement system; determining whether a change occurs in cellular response parameter of the disease cell sample in response to the therapeutic agent or agents as compared to a baseline measurement of the cellular response parameter before administration of the therapeutic agent or agents, wherein the change in cellular response parameter indicates that the agent or agents has therapeutic efficacy for the disease in the individual subject (responder) and lack of a change indicates that the therapeutic agent does not have efficacy for that subject's disease (nonresponder). In embodiments, the method further comprises further characterizing cells from a subject that are responsive to the therapeutic agent for other biomarkers and/or further characterizing cells from a subject that are not responsive to the therapeutic agent for other biomarkers. In embodiments, other biomarkers comprise gene mutations, single nucleotide polymorphisms, gene expression levels, proteins, protein mutations, splice variants, cell surface markers, overexpression of a protein or nucleic acid, amplification of a nucleic acid, cell morphology, and combinations thereof.

In yet other embodiments, a method for determining an optimal therapeutic regime or combination of drugs for a particular subject comprises administering a plurality of therapeutic agent combinations to separate disease cell samples from the same subject in in a device that measures at least one physiological parameter of a cell, wherein each therapeutic combination is administered to a separate disease cell sample from the same subject; and determining the physiologic response of each cell sample to each therapeutic combination compared to a baseline measurement, wherein the physiologic response indicates the most efficacious therapeutic combination of potential therapeutic combinations. In embodiments, the method further comprises selecting the therapeutic agent or combination of therapeutic agents that results in the change of at least one cellular response or physiologic parameter. In embodiments, the method further comprises administering the therapeutic agent or combination of therapeutic agents that results in the change of at least one cellular response or physiologic parameter to the subject.

In another aspect, a method comprises treating a patient for a disease by selecting a therapeutic agent for treating the disease comprising administering one or more therapeutic agents to at least one isolated disease cell sample from the subject in a cellular response measurement system; determining whether a change occurs in cellular response parameter of the disease cell sample in response to the therapeutic agent or agents as compared to a baseline measurement of the cellular response parameter before administration of the therapeutic agent or agents, selecting the therapeutic agent that causes a change in cellular response parameter; administering the therapeutic agent that results in the change of at least one cellular response or physiologic parameter to the subject. Therapeutic agents include those that are targeted to a specific biological pathway, those that inhibit cell proliferation, those that enhance cell killing, those that inhibit inflammation, those that kill microorganisms and/or those that enhance an immune response. In embodiments, where the therapeutic agent is targeted to a specific biological pathway, it may interact with a cell surface receptor and inhibit the action of the ligand for the receptor. For example, some breast cancer cells are positive for an epidermal growth factor receptor (EGFR) and respond to epidermal growth factor (EGF). The efficacy of a therapeutic agent that inhibits the interaction of EGF for an individual subject's cells can be determined in the presence and absence of the ligand.

In other embodiments, the therapeutic agent inhibits cell proliferation and/or cell killing. In those cases, a rate of change in a cellular response or physiological parameter can be measured on a sample and is indicative of the therapeutic agent's efficacy for causing cell death or inhibiting cell proliferation. In embodiments, the rate of change of a cellular response is determined in the presence and/or absence of the therapeutic agent and a known agent that enhances proliferation and/or inhibits cell killing.

In other aspects of the disclosure, kits are provided. In embodiments, a kit comprises: a container for a disease cell sample from an individual subject containing a transport medium; a container for a control cell sample containing a transport medium; a biosensor; and a non transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof; classifying the output as no response, weakly responsive, and responsive; and generating a report with the classification.

Cell Samples

Embodiments of the invention include systems, kits, and methods to determine the effectiveness of a therapeutic, monitor the effectiveness, or identify a dose of a therapeutic when administered to a subject's diseased cells.

Traditionally, disease has been classified by the tissue or organ that the disease affects. Due to better knowledge of the underlying mechanisms (e.g., genetic, autoimmune response, etc.), we now understand that diseases which affect the same tissue/organ, produce the same symptoms, etc., may have different etiologies and may have heterogeneous gene expression profiles. In addition, it has been shown in many diseases that there are responders and non-responders to therapeutic agents. In embodiments, any disease type, for which responders and non-responders are identified, can be employed in the methods herein in order to predict or prognosticate whether a particular therapeutic drug combination of drugs will be effective for a particular individual, e.g. a determination whether the individual is a responder or a non-responder.

One example of a disease type that is known to be heterogeneous in nature and to have responders and many non-responders is cancer. Cancer is typically classified according to tissue type. However, a more accurate description of the heterogeneity of cancer is reflected in the different mutations of the different cancers. An even more accurate description of the heterogeneity of cancer is the actual functional, physiological result of the mutation in a particular patient's cells. For instance, prostate cancer has different types and different mutations that cause cancer of this organ. Outcomes and treatments can be different based on whether the mutation causing the cancer is a gain of function (e.g., proto-oncogene causing increase protein production) or loss of function mutation (e.g., tumor suppressor) and in which gene. Due to the heterogeneity of a particular cancer, it would be expected that there would a heterogeneous response to a particular therapeutic agent. Embodiments of this invention allow the testing of a particular subject's cancer cells to a therapeutic agent or a panel of therapeutic agents to determine the efficacy of a specific therapeutic agent or the most effective therapeutic agent for a particular subject's cancer to select a treatment for the subject.

Embodiments of the invention include disease cell samples of cancer cells from individual subjects. Such cancer cells can be derived from, but not limited to, Acute Lymphoblastic Leukemia (ALL), Acute Myeloid Leukemia (AML), Adrenocortical Carcinoma, Anal Cancer, Appendix Cancer, Astrocytomas, basal cell carcinoma, Extrahepatic Bile Duct Cancer, Bladder Cancer, Bone Cancer, Osteosarcoma, Malignant Fibrous Histiocytoma, Brain Stem Glioma, Central Nervous System Atypical Teratoid/Rhabdoid Tumor, Central Nervous System Embryonal Tumors, Central Nervous System Germ Cell Tumors, Craniopharyngioma, Ependymoblastoma, Ependymoma, Medulloblastoma, Medulloepithelioma, breast cancer, Pineal Parenchymal Tumors of Intermediate Differentiation, Supratentorial Primitive Neuroectodermal Tumors, Pineoblastoma, Bronchial Tumors, Carcinoid Tumor, Cervical Cancer, Chronic Lymphocytic Leukemia (CLL), Chronic Myelogenous Leukemia (CML), Chronic Myeloproliferative Disorders, Colon Cancer, Colorectal Cancer, Cutaneous T-Cell Lymphoma, Ductal Carcinoma In Situ (DCIS), Endometrial Cancer, Esophageal Cancer, Esthesioneuroblastoma, Ewing Sarcoma, Extragonadal Germ Cell Tumor, Intraocular Melanoma, Retinoblastoma, fibrous histiocytoma, Gallbladder Cancer, Gastric Cancer, Gastrointestinal Carcinoid Tumor, Gastrointestinal Stromal Tumors (GIST), Gestational Trophoblastic Tumor, Glioma, Hairy Cell Leukemia, Heart Cancer, Hepatocellular Cancer, Langerhans Cell Histiocytosis, Hodgkin Lymphoma, Hypopharyngeal Cancer, islet cell tumors, Kaposi sarcoma, renal cell cancer, Laryngeal Cancer, Lip Cancer, Liver Cancer, Lobular Carcinoma In Situ (LCIS), Lung Cancer, Merkel cell carcinoma, Melanoma, mesothelioma, mouth cancer, multiple myeloma, Nasal Cavity and Paranasal Sinus Cancer, Nasopharyngeal Cancer, Neuroblastoma, Non-Hodgkin Lymphoma, Non-Small Cell Lung Cancer, Oral Cavity Cancer, Oropharyngeal Cancer, Ovarian Cancer, Pancreatic Cancer, Papillomatosis, Paraganglioma, Parathyroid Cancer, Penile Cancer, Pharyngeal Cancer, Pheochromocytoma, Pineal Parenchymal, Pituitary Tumor, Pleuropulmonary Blastoma, Prostate Cancer, rectal cancer, rhabdomyosarcoma, salivary gland cancer, squamous cell carcinoma, small intestinal cancer, testicular cancer, throat cancer, thyroid cancer, ureter cancer, urethral cancer, uterine cancer, vaginal cancer, vulvar cancer, and Wilm's tumor.

Autoimmune diseases are characterized by increased inflammation due to immune system activation against self antigens. Current therapies target immune system cells such as B cells and inflammatory molecules such as anti TNFα. Therapies can be broadly characterized as immune modulating or immunosuppressant. Drugs may be targeted to particular molecules such as TNF alpha, Integrins, sphingosine receptors, and interleukins. Other drugs act as anti-inflammatory agents such as corticosteroids. In yet other cases, drugs are immunosuppressants such as mercaptopurines and cyclophosphamide. With respect to autoimmune conditions, peripheral blood cells may be examined for the response to a certain therapeutic. In other embodiments, tissue samples of the site of inflammation, for example, synovial tissue in rheumatoid arthritis or colon tissue for ulcerative colitis.

For example, some patients with rheumatoid arthritis are known to be non-responders to anti-TNFα antibodies. In an embodiment, peripheral blood cells can be obtained from a patient suspected as having RA and a decrease in cell signaling ability of the patient's TNF Receptor and associated MAPK pathway can be used to determine whether the patient is likely to be a responder or non-responder to an immunomodulating or immunosuppressant compound. Likewise other therapeutics such as those targeting to IL-6, Interferon alpha, Interferon gamma, and the like may be tested in the same way. In other embodiments, it is known that patients that have multiple sclerosis are nonresponders to interferon beta. Cell samples from subjects can be tested against a panel of drugs to see which if any of the drugs are effective for a particular subject by inducing a change in a cellular physiological parameter. Examples of advantageous outcomes would be a reduction in cellular inflammation parameters, as determined by the American College of Rheumatology (ACR) criteria or an increase in cell adhesion for strengthening the blood-brain barrier function.

In other embodiments, patients may have a disease caused by infection of cells by a microorganism, a foreign body, or a foreign agent. Blood cells or tissue samples infected with a microorganism may be evaluated for responsiveness to various antibiotics, antivirals, or other therapeutic candidates. For example, there are a number of different therapeutic agents for hepatitis C infection that reduce viral function, infected tissue samples can be contacted with one or more therapeutic agents and a change in a cellular physiological parameter is detected. Therapeutic agents are selected that provide a change in a cellular physiological parameter of the infected tissue, and/or a therapeutic agent that provides a change in a cellular physiological parameter at the lowest dose. Outcomes such as increase in cell survival or increase in cell growth would be considered advantageous. In other embodiments where the therapeutic is designed to effect the human cell directly such as by blocking viral entry via a specific receptor type or perturbation of a cellular pathway, the patient cell could be tested for receptor binding or pathway perturbation by said therapeutic as described in other embodiments herein.

In embodiments, the cell samples can be obtained before therapy is initiated, during therapy, after therapy, during remission, and upon relapse. The methods as described herein are useful to predict therapeutic efficacy prior to treatment, during treatment, when a patient develops resistance, and upon relapse. The methods of the disclosure are also useful as to predict responders or non-responders to a therapeutic agent or combination of agents.

In embodiments, the cells are not contacted or treated with any kind of fixative, or embedded in paraffin or other material, or any detectable label. In embodiments, it is preferred that the cells remain whole, viable and/or label free. In some embodiments, a cell sample is provided for both the diseased tissue and healthy tissue. In some embodiments, the cell sample is provided in both viable and fixed form. A cell sample provided in fixed form can serve as a control for comparison to the viable cells that are analyzed in accord with the methods as described herein particularly for improved identification and correlation of additional biomarkers.

In embodiments of the invention, cells from an individual subject are used to determine therapeutic effectiveness. Cells can be collected and isolated by well-known methods (i.e., swab, biopsy, etc.). Both diseased and non-diseased cells can be used. Non-diseased cells can be used as a negative control, a baseline measure, a comparison for measures over time, etc. In embodiments, a control sample of tissue cells from the same subject may also be obtained. A control sample may be taken from another healthy tissue in the subject or from healthy tissue from the same organ as the diseased tissue sample. Diseased cells are cells extracted from a tissue with active disease. In an embodiment, diseased cells can be tumor cells, such as breast cancer cells. Cancerous cells do not necessarily have to be extracted from a tumor. For instance, leukemia cells can be collected from the blood of a patient with leukemia. Cells can be collected from different tissue sites such as the sites of metastasis, circulating tumor cells, primary tumor sites, and recurrent tumor sites, and cellular responsiveness compared to one another. In another embodiment, diseased cells can be extracted from a site of autoimmune disease, such as rheumatoid arthritis.

In embodiments, the number of cells in each tissue sample is preferably at least about 5000 cells. In embodiments, the cell number in the tissue sample may range from about 5000 to 1 million cells or greater. Cell samples include isolation from, but are not limited to, blood, blood serum, blood plasma, urine, semen, seminal fluid, seminal plasma, prostatic fluid, pre-ejaculatory fluid (Cowper's fluid), excreta, tears, saliva, sweat, biopsy, ascites, cerebrospinal fluid, lymph, marrow, or hair.

In an embodiment, the extraction of cells from a subject is at the same location as the CReMS (e.g., laboratory, hospital). As such, the cells can be suspended or preserved in a well-known transfer medium to bridge the time from subject to biosensor. In another embodiment, the extraction of cells from a subject is at a different location from the CReMS. Once obtained the cell samples are maintained in a medium that retains the cell viability. Depending on the length of time for transportation to the site of analysis, different media may employed. In embodiments, when transportation of the tissue sample may require up to 10 hours, the media has an osmolality of less than 400 mosm/L and comprises Na+, K+, Mg+, Cl—, Ca+2, glucose, glutamine, histidine, mannitol, and tryptophan, penicillin, streptomycin, contains essential amino acids and may additionally contain non-essential amino acids, vitamins, other organic compounds, trace minerals and inorganic salts, serum, cell extracts, or growth factors, insulin, transferrin, sodium selenite, hydrocortisone, ethanolamine, phosphophorylethanoloamine, tridothyronine, sodium pyruvate, L-glutamine, to support the proliferation and plating efficiency of human primary cells. Examples of such a media include Celsior media, Roswell Park Memorial Institute medium (RPMI), Hanks Buffered Saline, and McCoy's 5A, Eagle's Essential Minimal Media (EMEM), Dulbecco's modified Eagle's medium (DMEM), Leibovitz L-15, or modifications thereof for the practice of primary cell care. In embodiments, the media and containers are endotoxin free, nonpyrogenic and DNase- and RNase-free.

Cellular Response Measurement System ("CReMS")

Systems and methods of the invention utilize a cellular response measurement system (CReMS). CReMS refers to a device that can quantitatively determine a change in a physiological parameter in a cell, in and between cells, and between cells and the instrumentation device. A change in a physiological parameter is measured by determining change in an analyte (including non-limiting examples such as extracellular matrix, cell signaling molecule, or cell proliferation, tissue, cells, metabolites, catabolites, biomolecules, ions, oxygen, carbon dioxide, carbohydrates, proteins etc.). In embodiments, the biosensor is measuring a change in the physiological parameter in isolated whole label free viable cells. In embodiments, a biosensor is selected that can measure an expected change due to the type of therapeutic and/or activator agent.

An example of a CReMS is a biosensor. Examples of biosensors are electrochemical biosensors, electrical biosensors, optical biosensors, mass sensitive biosensors, thermal biosensors, and ISFET biosensors. Electrochemical biosensors measure potentiometric, amperometric and/or voltametric properties. Electrical biosensors measure surface conductivity, impedance, resistance or electrolyte conductivity. Optical biosensors measure fluorescence, absorption, transmittance, density, refractive index, and reflection. Mass sensitive biosensors measure resonance frequency of piezocrystals. Thermal biosensors measure heat of reaction and adsorption. ISFET biosensors measure ions, elements, and simple molecules like oxygen, carbon dioxide, glucose, and other metabolites of interest in the life sciences. In embodiments, the biosensor is selected from the group consisting of an impedance device, a photonic crystal device, an optical waveguide device, a surface plasmon resonance device, quartz crystal resonators/microbalances, and a microcantilever device. In embodiments, an optical biosensor can comprise an optical transducer for converting a molecular recognition or molecular stimulation event in a living cell, a pathogen, or combinations thereof. In a specific embodiment, the device is an impedance device.

In an example of a biosensor used to measure protein or other in vitro biomolecular interactions, the capture of a specific protein mass is translated into meaningful biochemical and biophysical values. Applying a simple calculation with the captured mass involving the molecular weight of the specific protein captured, the number of moles are evaluated, leading to equilibrium binding constants and other interaction descriptive values known to those experienced in the art. In an example of a biosensor used for cell assays, specific adhesion molecules on the cell surface modulate their attachment and morphology close to the surface of the sensor and other nearby cells upon application of external chemical or other stimulus via specific cellular pathways.

The biosensor can detect these modulations that can be selected in such a way as to be unique to the stimulus and pathway within the cell employed to respond to stimuli. When designed properly, the biosensor result for said cell assay can be exquisitely quantitative in molecular and functional terms. Said biosensor result can be a temporal pattern of response for further uniqueness. Biomolecular activators or perturbants known to turn on and turn off specific pathways within the cell can be used as controls for determining the specificity of the CReMS biosensor signal. Methods for curve deconvolution of the temporal response of the biosensor result (e.g. non-linear Euclidean comparison with control responses) can be applied to further more finely detail specific cellular responses. Use of titrating external stimuli in a cellular biosensor assay can also provide further biochemical and biophysical parameter description.

One example of a label-free sensor is a high frequency quartz resonator or quartz crystal microbalance (QCM) or resonating cantilever. The resonator includes a quartz crystal with a patterned metal electrode upon its surface. The quartz material has well-characterized resonance properties when a voltage is applied. By applying an alternating voltage to the electrodes at a particular frequency, the crystal will oscillate at a characteristic frequency. The oscillation frequency is modulated in quantitative ways when mass is captured on the sensor surface; additional mass results in lower resonator frequency. Therefore, by measuring small changes in the resonant frequency of the quartz oscillator, very small changes in deposited mass can be measured without attaching a label to the biomolecule or cell under study.

Ion Selective Field Effect Transistor (ISFET) devices are miniaturized, nanoscale, devices that are capable of measuring selected ions, elements, and simple molecules like oxygen, carbon dioxide, glucose, and other metabolites of interest in the life sciences. They have been extensively described at the electromechanical operational level as well as at the bioapplication level. To date they have not been described for the use with a specific patient's cells to discern response or resistance or temporal patterns thereof to proposed therapeutic intervention in disease processes.

Optical biosensors are designed to produce a measurable change in some characteristic of light that is coupled to the sensor surface. The advantage of this approach is that a direct physical connection between the excitation source (the source of illumination of the sensor), the detection transducer (a device that gathers reflected or transmitted light), and the transducer surface itself is not required. In other words, there is no need for electrical connections to an optical biosensor, simplifying methods for interfacing the sensor with fluid required for stabilizing and studying most biological systems. Rather than detecting mass directly, all optical biosensors rely on the dielectric permittivity of detected substances to produce a measurable signal. The changes in dielectric permittivity are related to the difference in ratio of the speed of light in free space to that in the medium. This change essentially represents the refractive index of the medium. The refractive index is formally defined as the square root of the dielectric constant of a medium (see Maxwell's equation for more explicit treatment of this relationship). An optical biosensor relies on the fact that all biological material, such as proteins, cells, and DNA, have a dielectric constant that is higher than that of free space. Therefore, these materials all possess the intrinsic ability to slow down the speed of light that passes through them. The optical biosensors are designed to translate changes in the propagation speed of light through a medium that contains biological material into a quantifiable signal that is proportional to the amount of biological material that is captured on the sensor surface.

Different types of optical biosensors include but are not limited to ellipsometers, surface plasmon resonant (SPR) devices, imaging SPR devices, grating coupled imaging SPR devices, holographic biosensors, interference biosensors, Reflectometric Interference Spectroscopy (RIF S), Colorimetric Interference Biosensors, Difference Interferometers, Hartman Interferometers, Dual Polarization Interferometers (DPI), Waveguide sensor chips, Integrated Input Grating Coupler devices, Chirped Waveguide Grating devices, Photonic crystal devices, Guided Mode Resonant Filter devices based upon Wood's Anomalies, Trianglular Silver Particle Arrays. And further include devices that measure a variety of wavelengths of the electromagnetic spectrum including but not limited to visible, ultraviolet, near infrared, and infrared. The modes of operation include but are not limited to scattering, inelastic scattering, reflection, absorbance, Raman, transmittance, transverse electric wave, and transverse magnetic wave.

The surface plasmon resonance device is an optical biosensor that measures binding events of biomolecules at a metal surface by detecting changes in the local refractive index. In general, a high-throughput SPR instrument consists of an auto-sampling robot, a high resolution CCD (charge-coupled device) camera, and gold or silver-coated glass slide chips each with more than 4 array cells embedded in a plastic support platform. SPR technology exploits surface plasmons (special electromagnetic waves) that can be excited at certain metal interfaces, most notably silver and gold. When incident light is coupled with the metal interface at angles greater than the critical angle, the reflected light exhibits a sharp attenuation (SPR minimum) in reflectivity owing to the resonant transfer of energy from the incident light to a surface plasmon. Binding of biomolecules at the surface changes the local refractive index and results in a shift of the SPR minimum. By monitoring changes in the SPR signal, it is possible to measure binding activities at the surface in real time.

Since SPR measurements are based on refractive index changes, detection of an analyte is label free and direct. The analyte does not require any special characteristics or labels (radioactive or fluorescent) and can be detected directly, without the need for multistep detection protocols. Measurements can be performed in real time, allowing collection of kinetic data and thermodynamic data. Lastly, SPR is capable of detecting a multitude of analytes over a wide range of molecular weights and binding affinities. Thus, SPR technology is quite useful as a cellular response measurement system.

A CReMS for the measurement of complex impedance changes (delta Z, or dZ) of live patient cells is described in this embodiment where impedance (Z) is related to the ratio of voltage to current as described by Ohm's law (Z=V/I). For example a constant voltage is applied to electrodes to which patient cells are attached, producing a current that at differential frequencies flows around, between cells and through cells. This CReMS is sensitive to the local ionic environment at the electrode interface with the cells and detects these changes as a function of voltage and current fluctuations. Physiologic changes of the cells as a result of normal function or perturbation thereof result in quantifiable changes to the flow of current around the electrodes and influence the magnitude and characteristics of the signal measured in such a CReMS.

In embodiments, the biosensor detects a change a global phenotype with event specificity. A global phenotype comprises one or more cellular response parameters selected from the group consisting of pH, cell adhesion, cell attachment pattern, cell proliferation, cell signaling, cell survival, cell density, cell size, cell shape, cell polarity, $O_2$, $CO_2$, glucose, and combinations thereof. With respect to event specificity, a cellular parameter is selected that reflects a change in a cell sample that is an expected change for that type of therapeutic and/or activator agent. For example, if a therapeutic agent is known to target a cytoskeletal element, a cell contacted with such an agent would be expected to show a change in cell adhesion in the presence of the agent.

In some embodiments, the change in attachment pattern is a change in cell adhesion. In some cases, the change in cell adhesion is indicated by a change in a refractive index or a change in impedance. In yet other embodiments, the change in attachment pattern is a change in basal morphology, a change in cell density, or a change in cell size or cell shape. In a specific embodiment, the change in basal morphology is a change in cell polarity. In embodiments, a decrease in cell signaling indicates a change in cytoskeletal organization.

In embodiments, the methods of the disclosure provide for analysis of cell samples that are label free and that can be measured in real time. In embodiments, the cell sample analyzed is a label free, viable, and not subject to any treatments to fix the cells. In embodiments, therapeutic and/or activator agents used in the methods and kits of the disclosure are also label free. To date label free methods have not been applied to determining therapeutic efficacy in effective ways.

Label free assays can reduce the time and cost of screening campaigns by reducing the time and misleading complications of label assays. Assays that can identify and quantify gene expression, gene mutation, and protein function are performed in formats that enable large-scale parallelism. Tens-of-thousands to millions of protein-protein or DNA-DNA interactions may be performed simultaneously more economically with label-free assays.

In contrast to the large variety of labeled methods, there are relatively few methods that allow detection of molecular interaction and even fewer still for cellular function without labels. Label-free detection removes experimental uncertainty created by the effect of the label on molecular folding od therapeutic and activator agents, blocking of active sites on cells, or the inability to find an appropriate label that functions equivalently for all molecules in an experiment that can be placed effectively within a cell. Label-free detection methods greatly simplify the time and effort required for assay development, while removing experimental artifacts from quenching, shelf life, and background interference.

Although labels are a mainstay of biochemical and cell-based assays, there are disadvantages to their use. Labels comprise the majority of all assay methods and have to overcome several problems, especially in the context of the study of complex activities in human cells. Use of radioactive labels create large quantities of contaminated materials and must be used in specialized facilities with regulatory methods to prevent harm (at the cellular level) to those that use them. The excitation/emission efficiency of fluorophores is degraded by time and exposure to light, reducing the ability of the label to be accurate and precise, and requiring that assays be read once only in an end point manner so that temporal information cannot be obtained. All label-based assays require a significant amount of time to develop a process for attaching the label in a homogenous and uniform manner, determining that the label will be linearly quantitative, and will not interfere or affect the interaction or process being measured. The uniform application of labels in complex mixtures is complicated by the presence of all the molecules that are needed for the process to proceed naturally. Addition of the label only allows for visualization of that molecule function indirectly, not the entire system function directly (i.e. some extended assumptions may be necessary). Cellular activities are even more difficult to measure accurately with labels. Besides figuring out how the label will get onto the right molecule, the right way, in the right location with respect to the cell, it is presently impossible to be certain that the label is not disturbing the normal cellular processes, thereby making the extrapolation to in vivo conditions tenuous.

Label-free detection generally involves the use of a transducer that is capable of directly measuring some physical property of a biological compound or bioentity such as a DNA molecule, peptide, protein, or cell. All biochemical molecules and cells have finite physical values for volume, mass, viscoelasticity, dielectric permittivity, heat capacity and conductivity that can be used to indicate their presence or absence, increase or decrease, and modification using a type of sensor. Additionally living systems utilize molecules to provide energy and carry out their life processes, such as $O_2$/$CO_2$ consumption/generation, glucose production/consumption, ATP production/consumption that cause measurable changes such as pH in their environ over finite periods of time. The sensor functions as a transducer that can convert one of these physical properties into a quantifiable signal such as a current or voltage that can be measured.

In some cases, in order to use a transducer as a biosensor, the surface of the transducer must have the ability to selectively capture specific material such as a protein or specific cell type, while not allowing undesired material to attach. Selective detection capability is provided by building of a specific coating layer of chemical molecules on the surface of the transducer. The material that is attached to the sensor surface is referred to as the sensor coating while the detected material is called the analyte. Thus, in some cases, a biosensor is the combination of a transducer that can generate a measurable signal from material that attaches to the transducer, and a specific recognition surface coating containing a receptor ligand that can bind a targeted analyte from a test sample.

In embodiments, a coating is selected for a biosensor that is associated with a particular cellular component or pathway. For example, in those cases, where the cellular physiological parameter is change in cell adhesion, a coating is selected that provides for adhesion of the cells in the cell sample to the biosensor surface. In embodiments, the coating that enhances adhesion of the cells to the biosensor includes extracellular matrix, fibronectin, integrins and the like. In other embodiments, a coating is selected that binds to a particular cell type based on a cell surface marker. In embodiments, such cell surface markers include, CD20, CD30, EGFR, EGFR-TK, PI3K, MEK1, MEK2, HER2 receptor, Her3 receptor, Her4 receptor, VEGFR, and other cell surface cancer biomarkers.

In embodiments, the biosensor is coated with a biomolecular coating. CReMS surfaces contacting cells may contain a biomolecular coating prior to addition of cells, during addition of cells, or after addition of cells. The coating material may be synthetic, natural, animal derived, mammalian, or created by cells placed on the sensor. For example, a biomolecular coating can comprise an extracellular matrix component known to engage integrins, adherins, cadherins and other cellular adhesion molecules and cell surface proteins (e.g., fibronectin, laminin, vitronectin, collagens, IntercellularCAMs, VascularCAMs, MAdCAMs), or a derivative thereof, or can comprise a biochemical such as polylysine or polyornithine, which are polymeric molecules based on the naturally occurring biochemicals lysine and ornithine, polymeric molecules based on naturally occurring biochemicals such as amino acids can use isomers or enantiomers of the naturally-occurring biochemical, antibodies, fragments or peptide derivatives of antibodies, complement determining region (CDR), designed to attach specific cell surface proteins to the biosensor.

A biosensor comprises an area to seed cells. For example, a biosensor can comprise a microtiter plate containing wells to seed cells. One or more cell samples can be seeded on a biosensor by physical adsorption to a surface in a distinct location. A biosensor can comprise 1, 10, 24, 48, 96, 384, or more distinct locations. A cell sample can comprise about 100 to about 100,000 individual cells or any cell number in between. An optimal cell sample depends on the size and nature of a distinct location on a biosensor. A cell sample can comprise about 5000 cells or less; about 10,000 cells or less; about 15,000 cells or less; about 20,000 cells or less; about 25,000 cells or less; or about 50,000 cells or less. A cell sample can comprise about 1000 to about 2500 cells; about 1000 to about 5000 cells; 5000 to about 10,000 cells; about 5000 to about 15,000 cells; about 5000 to about 25,000 cells; about 1000 to about 10,000 cells; about 1000 to about 50,000 cells; and about 5000 to about 50,000 cells.

In embodiments, a change in a cellular response or physiological parameter is measured over a defined period of time. In embodiments, the defined period of time is the amount of time that it takes for the control cells to reach a steady state in which a change in the output of the physiological parameter varies by 20% or less. In embodiments, the change is observed in cells in 1 hour or less. In other embodiments, the change is observed in cells for at least 1 min. to about 60 min. and every minute in between. In other embodiments, the change in cell response is measured from about 10 minutes to about one week or 200 hours. In embodiments, when a therapeutic agent is targeted to a cellular pathway, the cellular response is measured from about 10 minutes to about 5 hours, about 10 minutes to about 4 hours, about 10 minutes to about 3 hours, about 10 minutes to about 2 hours, about 10 minutes to about 1 hour, or about 10 minutes to about 30 minutes or any time point in between. In embodiments, when a therapeutic agent affects cell proliferation or cell killing or cellular resistance, the cellular response is measured from about 1 hour to about 200 hours. In yet other embodiments, a combination of responses (otherwise described as a full temporal pattern) between 1 minute and 200 hours is used to determine therapeutic effect of a compound on cells and the cells ability to develop resistance. This timeframe encompasses the important process of short-term pathway signaling, dynamic reprogramming and longer term cellular responses important in assessing a probable response and maintenance thereof in a patient.

Once cells of a particular subject have been seeded on a biosensor, baseline measurements can be determined. Baseline measurements can be taken on the same cell sample, or a control cell sample. A control sample can comprise healthy cells or diseased cells from the same patient and/or same tissue. A control sample can comprise disease cells known to respond to the agent. In other embodiments, a control sample comprises disease cells known not to respond to the agent. A control sample may include application of an activator agent to healthy or diseased cells of a particular patient, designed to elicit a standardized response relating to cell health, cell metabolism, or cell pathway activity.

The control would be determined for each disease and or drug type. One practice would be a comparison against a healthy cell control from the same patient. For example, with cell killing drugs, the method will show benefit of killing disease cells over healthy cells to achieve a significant therapeutic index. Other ideal embodiments would include the use of pathway tools to determine pathway function and control by the drug. In an example of targeted therapeutics, tools are activator agents, bioreagents or small molecules used as controls to perturb a pathway and determine a targeted drug's ability to disrupt the perturbation. For yet other embodiments, the physiologic effect of a drug on cell would be measured without exogenous perturbation by an activator agent noting for example the temporal pattern or rate of oxygen consumption, the rate or temporal pattern of acidification, ion flux, or metabolite turnover.

A continuous time course of the biosensor signal is the preferred embodiment. There are distinctive patterns on the time vs. biosensor signal plot that are indicative of a patient cell response to drug treatment. Evaluation of these patterns is useful to identify the presence of an efficacious event. A time course or constantly changing measurement of live and fully functional cells is more beneficial than the current practice used in typical whole cell assays that only represent a point in time. The methods described herein measure dynamic systems as they would occur in a patient and represent the most accurate means of determining patient response. In the case of pathway responses, recording of a complete time course or temporal pattern is superior in ability to support more complex analysis and obviates selecting the optimum time point for a single measurement.

Comparison against controls could occur at a temporal maxima, minima, or as differences between maximal signal-minimal signal, or by comparing integrated areas under a curve (AUC) for a time course plot or other non-linear comparisons of the test well against positive or negative control wells. Additional analyses supported only by measuring with a biosensor are time to reach maxima/minima, and other derivatives of the temporal time course. In the case of longer term responses, the time of comparison may be of a specific time point after a few days or a week of treatment or multiple applications of drug. The longer time course may also compare changes in slope or compare second derivatives of the time versus biosensor signal plot at the beginning, middle or end of a week of drug treatment. Significant changes compared to control may include absolute drop in biosensor signal related to curtailment of cellular metabolism. Alternatively, the drop may be followed by an increase that could indicate development of resistance to the drug during the assay. Additionally, non-linear Euclidean analyses could be used to produce a measure of total differences between controls and patient samples over a complete time-course. This too would be significant with respect to predicting the outcome for a patient.

In embodiments, the output of a biosensor over a defined period of time is represented as a cell index. The cell index is the change in impedance from a test starting point. Cell Index is defined as a measurement of impedance and can be applied in one instance of the present invention by measuring at a fixed electrical frequency of, for example, 10 kHz and fixed voltage.

And calculated by the equation Cell Index$_i = (R_{tn} - R_{t0})/F$

Where:
i=1, 2, or 3 time point
F=15 ohm in one example when the instrument is operated at 10 kHz frequency
$R_{t0}$ is the background resistance measured at time point T0.
$R_{tn}$ is the resistance measured at a time point Tn following cell addition, cell physiologic change, or cell perturbation.

Cell index is a dimensionless parameter derived as a relative change in measured electrical impedance to represent cell status. When cells are not present or are not well-adhered on the electrodes, the CI is zero. Under the same physiological conditions, when more cells are attached on the electrodes, the CI values are larger. CI is therefore a quantitative measure of cell number present in a well. Additionally, change in a cell physiological status, for example cell morphology, cell adhesion, or cell viability will lead to a changes in CI.

The cell index is a quantitative measure of the presence, density, attachment or changes thereof based upon a starting point or baseline impedance measurement. The baseline starting point impedance is a physical observable characteristic and an indication of the health, viability, and physiologic status of a cell prior to any treatment with drug or other perturbant. The baseline starting point can be used as a qualitative control for the CELx test. Addition of drug or perturbant causes the impedance to change in temporal patterns reflective of the specificity of the cellular physiologic change experienced by the cell. Changes in a cell physiological status, for example cell morphology, cell number, cell density, cell adhesion, or cell viability will lead to a changes in the cell index.

A change in a cellular response or physiological parameter is determined by comparison to a baseline measurement. The change in cellular parameter or physiological response depends on the type of CReMS. For example, if the change in cellular response is determined optically, physically observable changes could be measured for example as a function of optical density at spectral wavelengths for chemical absorbance or transmittance, changes in a surface plasmon measurement device, or changes detected by photonic crystal devices. If the change in cellular parameter or physiological response is determined electrically, physically observable changes could be measured for example using milli or micro impedance changes of cells adhered to electrodes. Changes in pH, glucose, carbon dioxide, or ions, could be measured electronically using ion selective field effect transistors (ISFET).

In other embodiments, a rate of change is determined by a method measuring a CReMS response for a period of time required to determine a difference in cellular physiologic response to a therapeutic. The rate of change is described by various interpretation of the time course data and can be expressed as a rate or further derivative function of the rate including acceleration of the rate.

In embodiments, one or more cutoff values for determining a change in cellular response is determined by a method comprising: determining a standard deviation, a signal to noise ratio, a standard error, analysis of variance, or other statistical test values known by those practiced in the art for determining appropriate confidence intervals for statistical significance of a set of samples from known responding cell samples and from a set of samples from known nonresponding patiecompunts; and determining the difference between the two and setting the cutoff value between the confidence intervals for both groups. Preferred embodiments include 80-90% confidence intervals, more preferred embodiments include >90% confidence intervals and most preferred embodiments include >95% or >99% confidence intervals. In embodiments, a cutoff value is validated by determining the status of blinded known samples as responders or nonresponders using a cutoff value and unblinding the sample and determining the accuracy of predicting the status of the sample. In the case of a single cutoff value, values that fall below the cutoff value or are closer to the values for the known responders indicate the patient sample is exhibiting responsiveness to the therapeutic agent and if the values are at or above the cutoff value or are closer to the values for the known non responders value, the cell sample is identified as a non responder to the therapeutic agent.

In some embodiments an output of the biosensor at a defined period of time is classified as no response, weakly responsive or responsive. An output at a defined period of time is selected in order to classify the output into the categories. In embodiments, the defined period of time is the end point of the time period for which the cells have been continuously monitored in the biosensor. In embodiments, the time period is at least 60 minutes, 60 hours, or 120 hours. In embodiments, an output classified as no response, is indicated by an output value that differs from the output value of the baseline prior to administration of a therapeutic agent or a control cell not treated with the therapeutic agent no more than at least 20% or less, 15% or less, 10% or less, or 5% or less. In embodiments, an output classified as weakly responsive is indicated by an output value that differs from the output value of the baseline prior to administration of a therapeutic agent or a control cell not treated with the therapeutic agent of at least 50% or less and greater than 5%. In embodiments, an output classified as responsive is indicated by an output value that differs from the baseline prior to administration of a therapeutic agent or a control cell not treated with the therapeutic agent of at least greater than 50%. In embodiments, the control sample is a sample of the disease cells from the same subject and not treated with the therapeutic agent.

Therapeutic and Activator Agents

Often a when a patient is diagnosed with a particular disease or condition, there is a range of treatment options. In some cases, treatments may be very expensive or the side effects associated with the treatment may be severe so it would be useful to know whether the patient is likely to be a responder or a non-responder to a treatment. In addition, if a patient becomes resistant, it would be useful to know which other treatments might be efficacious now that the patient's diseased cells have become resistant.

In embodiments, any therapeutic agent or agents that are used in the treatment of a condition for which some patients respond and others do not respond can be analyzed in the methods described herein. For example, for cancer, a number of targeted immunotherapies are available including a number of different chimeric and humanized antibodies. For autoimmune conditions, molecules such as those targeted to inflammatory cytokines or their receptors may be analyzed. Examples of agents targeted to inflammatory cytokines are anti-TNF a agents, agents targeting interferon alpha, interleukins, and the like. Immunosuppressive agents such as corticosteroids, tacrolimus (FK-506 or TACR) (inhibits T-cell metabolism and proliferation), sirolimus (SIRO/81768), myocophenolic acids, mycophenolate mofetil (MMF), calcineurin inhibitors (CI), cyclosporin (CsA), and rapamycin (mTOR inhibitor).

In embodiments, the methods as disclosed herein involve testing of one or more therapeutic agents for the ability to cause a change in a physiological parameter of the diseased cells from the individual subject. In embodiments, the therapeutic agents are also label free. In some embodiments, two or more therapeutic agents may be tested separately or in combination on separate samples of the diseased cells from the same patient. A therapeutic agent is selected that causes the greatest change in the cellular response or physiological characteristic at a lower dose than other therapeutic agents. Combinations of compounds may be determined that offer the greatest therapeutic effect. In embodiments, the determination may be as compared to healthy cells of the patient to determine therapeutic index and other individual safety and tolerance effects.

In some embodiments, when a therapeutic agent is a targeted therapeutic agent that affects a cellular pathway, the change in cellular responsiveness is measured in the absence or presence of an activator agent or perturbant of the pathway. A therapeutic agent is selected that inhibits the cellular responsiveness to the perturbant of the pathway as compared to baseline measurement and optionally, as compared to other therapeutic agents.

In other embodiments, when a therapeutic agent is a targeted therapeutic agent that binds to a cell surface receptor, the change in cellular responsiveness is measured in the absence or presence of an activator agent or perturbant that binds to the receptor. In embodiments, the therapeutic agent is administered to the cell sample before or after the activator or perturbant. In embodiments, the activator agent or perturbant is label free. A therapeutic agent is selected that inhibits the cellular responsiveness to the activator agent or perturbant as compared to baseline measurement and optionally, as compared to other therapeutic agents, regardless of the density of the cell surface receptors. In some embodiments, a therapeutic agent is selected that inhibits the action of the activator agent or perturbant independent of the density of cell receptors.

The change in the physiological parameter can be an increase or a decrease in the parameter as compared to baseline or healthy cell control. The changes could represent full agonism, superagonism, irreversible agonism, selective agonism, co-agonism, inverse agonism, or partial limiting agonism, reversible and irreversible antagonism, competitive antagonism, non-competitive antagonism, un-competitive antagonism. The changes can occur sooner, later or not at all as compared to an appropriate control. The changes could be selected to occur for a longer or shorter period of time. Changes could be selected that are reversible or irreversible.

For example, a therapeutic agent that results in a decrease in cell signaling would be selected for treatment of an autoimmune condition. Peripheral blood cells that respond to an agent that inhibits the action of a cytokine show a decrease in cell signaling. In another example, for disease cells responsive to an anticancer agent, such as a humanized antibody targeted to a receptor like Her2, the disease cells would show a significant reduction in EGF family pathway signaling. In other cases, for disease cells responsive to an anti-angiogenic agent, the disease cells would show a reduction in VEGF pathway signaling or reduction in proliferative ability. The CReMS response or physically observable characteristic measured for each type of agent is dependent upon the intended phsyiological response the drug was designed to illicit and can be as specific or general as needed. The key is the use of the CReMS for physiological measurement of a live cell for a period of time to test the response the drug was intended to alter.

A particular therapeutic agent or agents can be administered to the diseased cells, and optionally, healthy cells to determine the effectiveness of the particular therapeutic or therapeutics. Diseased cells and/or healthy cells can also be untreated so as to compare the effect of the therapeutic or therapeutics on treated and untreated diseased and/or healthy cells. A single therapeutic can be administered to determine how a subject will respond to the therapeutic treatment. In another embodiment, a panel of different therapeutics can be administered to cells of a particular subject.

In embodiments, a cutoff value for efficacy of a therapeutic agent to inhibit activation of a cellular pathway is determined in one embodiment by adding the drug and measuring the physiologic response. In another embodiment, the pathway is stimulated with and without drug pre-treatment. Changes to the physiologic baseline signal or reductions of the stimulation signal by the drug at the 85% confidence interval or ideally greater than the 90% confidence interval or more ideally greater than the 95% or 99% confidence interval are deemed efficacious. In embodiments, a cutoff value for efficacy of a therapeutic agent that inhibits cell proliferation or enhances cell killing is determined by recording the physiologic response over time. Reductions to the physiologic baseline signal or deviation from the temporal pattern as compared to non-treated or healthy cells or a combination thereof by the drug at the 85% confidence interval or ideally greater than the 90% confidence interval or more ideally greater than the 95% or 99% confidence interval are deemed efficacious.

The sensitivity and specificity of the therapeutic agent for treating the disease of an individual subject is determined by comparing the cellular physiologic pathway response as measured by the CReMS to determine that the drug is working as it was designed on a specific target and determining that a cutoff value for efficacy has been attained.

Therapeutic agents can include without limitations agents that are targeted to a particular cellular pathway and/or agents that inhibit cell proliferation or cause cell killing. Examples of pathways that therapeutic agents target include MAPK-PK, RAS/RAF, RHO, FAK1, MEK/MAPK, MAK, MKK, AKT, EGF receptor, Her2 receptor, Her 3 receptor, Her 4 receptor, PIK3/PTEN, VEGF receptor pathway inhibitors, cell adhesion, TGFbeta/SMAD, WNT, Hedgehog/GLI, HIF1 alpha, JAK/STAT, Notch, control of Gl/S transition, DNA damage control, apoptosis.

In embodiments, therapeutic agents comprise a number of small molecule and antibody drugs such as trastuzumab, pertuzumab, lapatinib, docetaxel, tamoxifen, cisplatin, abraxane, paclitaxel injection, brentuximab vedoton, everolimus, pemetrexed, exemestane, ofatumumab, bevacizumab, alemtuzumab, irinotecan, bicalutamide, oxaliplatin, cetuximab, visomedegib, toremifene citrate, fulvestrant, gemcitabine, imatinib, ixabepilone, topeotecan, axitinib, romidepsin, cabrazitaxel, sorafenib, infliximab, lenalidomide, rituximab, dasatinib, sunitinib, erlotinib, nilotinib, paclitaxel, temozolomide, trioxide, panitumumab, bortezomib, azacitidine, pazopanib, crizotinib, capecitabine, ipilimumab, vemurafenib, goserelin acetate, abiraterone, a BH3 mimetic, navitoclax, anastrozole, letrozole, an aromatase inhibitor, cyclophosphamide, doxorubicin, methotrexate, fluorouracil, ixabepilone, carboplatin, aflibercept, temsirolimus, irbritumomab, abiraterone, custirsen, neratinib and combinations thereof. The targets of these therapeutic agents are known.

In embodiments, a method for determining therapeutic efficacy of an agent for a disease in an individual subject comprising: administering the agent to at least one isolated disease cell sample from the individual subject in a cellular response measurement system (CReMS); and determining whether a change in a cellular response parameter of the cell sample to the agent occurs as compared to a baseline measurement, wherein the change in cellular response indicates that the agent has therapeutic efficacy for the disease in the individual subject. In embodiments, a method further comprises administering to at least one isolated disease cell sample from the individual subject in a cellular response measurement system an activator agent or perturbant that perturbs the cellular response pathway before or after administering the therapeutic agent.

In some embodiments, the therapeutic agent is targeted to a cell surface receptor and/or a cellular pathway. In that case, the sample is contacted with a therapeutic agent before the sample is activated with an activator agent or perturbant of the pathway. In embodiments, the activator agent or perturbant comprises a specific growth factor, vascular endothelial growth factors, phosphatidyl inositol, epidermal growth factors, hepatocyte growth factors, m-CSF, RANK ligand, Tumor Necrosis Factors (TNF-α), neuregulin, estrogen, progesterone, folate, adenosine triphosphate, and FAS Ligand, Platelet derived growth factors (PDGF), or other agents of cellular pathway or signaling stimulation such as the subject's plasma or serum, Na+, K+, Mg+, Cl—, Ca+2, glucose, glutamine, histidine, mannitol, and tryptophan, antibiotics (rapamycin), essential and non-essential amino acids, vitamins, other organic compounds, trace minerals and inorganic salts, serum, cell extracts, fractionated cell extracts or fractionated serum, extracellular signaling factors, intracellular signaling factors, insulin, transferrin, sodium selenite, hydrocortisone, ethanolamine, phosphophorylethanoloamine, tridothyronine, sodium pyruvate, L-glutamine. In embodiments, therapeutic agents are those that affect diseased cells by inhibiting cell proliferation, enhancing cell killing, and rendering the cell unresponsive or less responsive to signals that lead to a diseased state. Examples of such therapeutic agents include cyclophosphamide, 5-FU, capaecitabine, and other pyrimidine drugs, others SN-38 metabolite analogs (Ex. irinotecan), taxols, and platinum containing drugs (Ex. cisplatin).

In some embodiments, the response of a sample to one or more of these agents can also be measured in the presence or absence of a growth factor that stimulates cell proliferation or of an anti-apoptotic agent. Growth factors that stimulate cell proliferation include growth hormone, epidermal growth factor, vascular endothelial growth factor, platelet derived growth factor, hepatocyte growth factor, transforming growth factor, fibroblast growth factor, nerve growth factors, and others known to those practiced in the art. Anti-apoptotic agents include compounds that regulate anti-apoptotic proteins or pathways (Ex. taxols on Bcl-2 protein activity and Gefitinib for control of the anti-apoptotic Ras signalling cascade).

For example, for a particular subject diagnosed with breast cancer and determined to be Her2 positive, cells isolated from that subject can be tested for responsiveness to particular anti-cancer therapeutics, especially anti-Her2 therapeutics. For instance, cells from the Her2+ subject can be tested for responsiveness to trastuzumab or lapatinib in the presence or absence of epidermal growth factor (EGF) and/or homologous structured peptides, neuregulin, or heregulin. In an embodiment, cells from the subject can be seeded on a biosensor. In embodiments, cells are label free whole cells. Such cells can be both cells from the breast cancer tumor and healthy breast tissue. Trastuzumab or lapatinib can be administered to a sample of diseased cells and, optionally, a sample of healthy cells. In some embodiments, the cell samples treated with trastuzumab are then contacted with Her receptor activator such as neuregulin. A sample of both diseased and healthy cells can remain untreated. A cellular response is determined using a cellular response measurement system (CReMS). In embodiments, the cellular response is determined after 1 hour or less. The effectiveness of trastuzumab treating the cells of the particular subject can then be determined in the presence or absence of perturbation of the pathway.

In embodiments, an agent is selected that inhibits the cellular response of the individual subject's cell sample to an activator of the cellular pathway, activator of cell proliferation, or inhibitor of apoptosis. When a number of different therapeutic agents that activate the same or different pathways are evaluated in a method of the disclosure, an agent is preferably selected that can inhibit the activator or inhibitor response at a lower concentration than the others.

In similar embodiments, therapeutic agents are those that affect diseased cells by agonizing or partially agonizing cellular activity where reduced activity has led to the diseased state.

The test can measure the effectiveness of a drug in a range of concentrations from below 1 nM to greater than 100 uM generally with less than 20% standard deviation and optimally with less than 5% standard deviation. The compound test range will correspond to dosing levels as defined on a drug packaging label known as the maximum tolerated dose. Unlike most tests that cannot ascertain the number of live cells in the actual set of cells in the test, this test is only working with the live cells as determined in a quality control and baseline physiologic determination step at the beginning of the test. The result of this feature reduces the variance of the test result. The test can be conducted using a temperature, oxygen, humidity, and carbon dioxide range generally acceptable for cell viability commonly known to those practiced in the art. In some cases, a preferred temperature range is between 25° C.–40° C. In other cases the temperature may be optimized further to ±0.5° C. within this range for specific perturbations and maintained using standard temperature controlled incubator cabinets.

In another embodiment, samples of the diseased cells form an individual can be tested for responsiveness to a panel of anticancer therapeutics. For cancer, a number of small molecule and antibody drugs are available. Examples of such therapeutic agents include trastuzumab, pertuzumab, lapatinib, docetaxel, tamoxifen, cisplatin, abraxane, paclitaxel injection, brentuximab vedoton, everolimus, pemetrexed, exemestane, ofatumumab, bevacizumab, alemtuzumab, irinotecan, bicalutamide, oxaliplatin, cetuximab, visomedegib, toremifene citrate, fulvestrant, gemcitabine, imatinib, topeotecan, axitinib, romidepsin, cabrazitaxel, sorafenib, infliximab, lenalidomide, rituximab, dasatinib, sunitinib, erlotinib, nilotinib, paclitaxel, temozolomide, trioxide, panitumumab, bortezomib, azacitidine, pazopanib, crizotinib, capecitabine, ipilimumab, vemurafenib, goserelin acetate, abiraterone, a BH3 mimetic, navitoclax, anastrozole, letrozole, an aromatase inhibitor, cyclophosphamide, doxorubicin, methotrexate, fluorouracil, and combinations thereof.

For instance, samples of cells collected from a Her2+ subject can tested against a panel of anti-breast cancer therapeutics, including anti-Her2 therapeutics. In an embodiment, each sample of cells from the subject can be administered one of the anti-breast cancer therapeutics. A panel of anti-breast cancer therapeutics can include, but are not limited to, trastuzumab, pertuzumab, lapatinib, docetaxel, tamoxifen, cisplatin, a BH3 mimetic, an aromatase inhibitor, cyclophosphamide, doxorubicin, methotrexate, fluorouracil, NeuVax™ (E75 peptide administered with adjuvant sargramostim (rGM-CSF)), and combinations thereof. The aromatase inhibitor can be at least one of aromatase inhibitor is anastrozole, letrozole, or exemestane. The BH3 mimetic can be navitoclax.

In an embodiment, an anti-breast cancer therapeutic can be a Her/Neu receptor family activity modulators (e.g., pertuzumab), cellular growth factor receptor modulators (e.g., modulators of vascular endothelial growth factor (VEGF) receptors), mitogen activated protein kinase (MAPK) pathway modulators, (PI3K) pathway modulators, a BH3 mimetic, an aromatase inhibitor, or combinations thereof.

Methods of the invention include administering candidate therapeutics to a subject's cells to determine safety and to determine therapeutic effectiveness. Additionally, administration of a candidate therapeutic to a subject's diseased cells may be used as a method of selecting the proper patient population for a phase II or III clinical trial. Methods of the invention include testing diseased cells against known therapeutic combinations. Additionally, methods of the invention include testing known and candidate therapeutics.

Methods of the invention also including administering combinations of therapeutic agents to determine if a particular combination of agents produces a more effective result (i.e., amelioration or cure of disease symptoms). A combination of therapeutic agents is two or more therapeutic agents administered to the same cell sample. In an embodiment of the invention, the combination of therapeutic agents is administered to a cell sample concurrently. In an embodiment, at least one therapeutic agent is administered to the cell sample at a time different than the administration of the other at least one therapeutic agent of the combination.

After administration of therapeutic agents to a cell sample, real time data can be collected on multiple aspects of the cell sample. For instance, pH and temperature can be measured. Additionally, other factors, such as "cell death factors", can be determined. A cell death factor as determined by a CReMS can be a change in a physicochemical property as measured by the CReMS. For instance, cancer cells will attach to a surface and provide a baseline reading for a refractive index. Administration of a therapeutic agent that promotes cancer cell death would cause a change in the refractive index since the cancer cells in a sample would round up and detach from a surface. This could be measured by an optical biosensor utilizing surface plasmon resonance in a continuous real-time manner.

An embodiment includes a method for determining therapeutic efficacy of an agent for a particular subject comprising administering the agent to a disease cell sample from the subject in a CReMS and determining the physiologic response of the cell sample to the agent compared to a baseline measurement, wherein the physiologic response indicates therapeutic efficacy of the agent. The agent administered to a disease cell sample can be a single agent or two or more agents. When the agent is two or more agents, the two or more agents can be administered concurrently or at different times. For instance, one agent can be administered to a cell sample and a second agent can be administered a later time (e.g., 10 minutes later). A method can also include administering a placebo to a diseased cell sample. A method can also include administering the agent(s) to be tested on a healthy cell sample.

In embodiments, the methods as described herein provide for a method to determine an optimal dose range for a particular therapeutic. Determination of a dose range allows for proper design of clinical trials and/or allows the physician to balance efficacy with detrimental side effects. In embodiments, a method comprises administering a range of doses of a therapeutic agent to separate samples of diseased cells from the same patient, and determining the dose range that results in a change in a physiological parameter of the cells as described herein as compared to baseline and/or healthy control cells.

Once any of the methods described herein are used to determine whether an individual subject's disease cells respond to one or more therapeutic agents, the results are communicated to a health care worker to allow for selection of a therapeutic agent for treatment of the subject. In embodiments, the methods further comprise administering the selected therapeutic agent to the subject.

Kits

In another aspect of the disclosure kits are provided. In embodiments a kit comprises a container for a disease cell sample from an individual subject containing a transport medium; a container for a control cell sample from the individual subject containing a transport medium; a biosensor; a non transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof; classifying the output as above or below a cutoff value indicating status as a responder or nonresponder and/or classifying the sample as having no response, weakly responsive, and responsive; and generating a report with the classification.

Types and amount of a disease cell samples are described herein. In embodiments, the disease cell sample is a whole cell label free viable cell sample having at least 5,000 cells. In embodiments, a control cell sample is selected from the group consisting of a disease cell sample from the same subject, a healthy cell sample from the same subject, a cell sample known to respond to the therapeutic agent, a cell sample known not to respond to the therapeutic agent, and combinations thereof.

The containers and the transport medium are designed to maintain cell viability and to minimize cell activation. In embodiments, the media and containers are endotoxin free, nonpyrogenic and DNase- and RNase-free. Once obtained the cell samples are maintained in a transport medium that retains the cell viability. Depending on the length of time for transportation to the site of analysis, different media may be employed. In embodiments, when transportation of the tissue sample may require up to 10 hours, the media has an osmolality of less than 400 mosm/L and comprises Na+, K+, Mg+, Cl—, Ca+2, glucose, glutamine, histidine, mannitol, and tryptophan, penicillin, streptomycin, contains essential amino acids and may additionally contain non-essential amino acids, vitamins, other organic compounds, trace minerals and inorganic salts, serum, cell extracts, or growth factors, insulin, transferrin, sodium selenite, hydrocortisone, ethanolamine, phosphophorylethanoloamine, tridothyronine, sodium pyruvate, L-glutamine, to support the proliferation and plating efficiency of human primary cells. Examples of such a media include Celsior media, Roswell Park Memorial Institute medium (RPMI), Hanks Buffered Saline, and McCoy's 5A, Eagle's Essential Minimal Media (EMEM), Dulbecco's modified Eagle's medium (DMEM), Leibovitz L-15, or modifications thereof for the practice of primary cell care.

Biosensors are described herein. In embodiments a biosensor is selected from the group consisting of a biosensor that detects a cellular parameter selected from the group consisting of, cell adhesion, cell attachment, cell morphology, cell phenotype, cell proliferation, cell signaling, cell density, cell polarity, pH, $O_2$, $CO_2$, glucose, and combinations thereof. In embodiments, the device is an impedance or an optical device. Biosensors may be optionally coated as described herein. In embodiments, a biosensor is selected that measures a change in a physiological parameter associated with the type of therapeutic and/or activator agent as described herein.

In embodiments a kit comprises a non-transitory computer readable medium having computer executable instructions for converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof classifying the output as a responder or nonresponder and/or no response, weakly responsive, and responsive; and generating a report with the classification.

In embodiments, the disclosure provides a computing device or computer readable medium with instructions to implement the methods of the disclosure. The computer readable medium includes non-transitory CD, DVD, flash drive, external hard drive, and mobile device.

The kits and methods described herein can employ the use of a processor/computer system. For example, a general purpose computer system comprising a processor coupled to program memory storing computer program code to implement the method, to working memory, and to interfaces such as a conventional computer screen, keyboard, mouse, and printer, as well as other interfaces, such as a network interface, and software interfaces including a database interface find use one embodiment described herein.

The computer system accepts user input from a data input device, such as a keyboard, input data file, or network interface, or another system, such as the system interpreting, for example, the data generated by the biosensor over a defined period of time, and provides an output to an output device such as a printer, display, network interface, or data storage device. Input device, for example a network interface, receives an input comprising a change in a cellular physiological parameter as described herein and/or quantification of these changes. The output device provides an output such as a display, including one or more numbers and/or a graph depicting the detection and/or quantification of the change in a cellular parameter.

Computer system is coupled to a data store which stores data generated by the methods described herein. This data is stored for each measurement and/or each subject; optionally a plurality of sets of each of these data types is stored corresponding to each subject. One or more computers/processors may be used, for example, as a separate machine, for example, coupled to computer system over a network, or may comprise a separate or integrated program running on computer system. Whichever method is employed these systems receive data and provide data regarding detection/diagnosis in return.

In some embodiments, the computing device can include a single computing device, such as a server computer. In other embodiments, the computing device can include multiple computing devices configured to communicate with one another over a network (not shown). The computing device can store multiple databases within memory. The databases stored on the computing device can be organized by clinic, practicing clinician, programmer identification code, or any other desired category.

Data from the biosensor can be sent to the remote computing system or another data storage device. The communication process initializes and begins at a start module and proceeds to a connect operation. The connect operation communicatively couples the stored information of the health care provider to the remote computing system, for example, via a cabled connection, a wireless local area network (WLAN or Wi-Fi) connection, a cellular network, a wireless personal area network (WPAN) connection, e.g., BLUETOOTH®, or any desired communication link.

A transfer operation transmits data from the biosensor to the computing device. In an embodiment, the transfer operation encrypts the data before transmitting the data between the devices. The communication process can complete and end at a stop module. Once the biosensor data is transferred to a remote computing device, the data is converted to an output, such as a cell index measurement over time. In embodiments, a defined endpoint is selected and is used to classify the cell sample as no response, weakly responsive or responsive as described herein. In embodiments, the status of the analysis of the sample as a responder or non responder is communicated back to the health care provider using a similar process over cabled connection, a wireless local area network (WLAN or Wi-Fi) connection, a cellular network, a wireless personal area network (WPAN) connection, e.g., BLUETOOTH®, or any desired communication link.

In embodiments, the computer readable storage medium having computer-executable instructions that, when executed by a computing device, cause the computing device to perform steps comprising: converting data from the biosensor into an output, wherein the output shows a change in a cellular physiological response parameter over a defined period of time, wherein the cellular physiological response parameter is selected from the group consisting of pH, cell adhesion, cell attachment pattern, cell proliferation, cell signaling, cell survival, cell density, cell size, cell shape, cell polarity, $O_2$, $CO_2$, glucose, and combinations thereof in the presence and/or absence of a therapeutic agent; classifying the output as no response, and responsive at a defined endpoint by comparing the output from biosensor from the cell sample in the presence of the therapeutic agent to the output from biosensor from the cell sample in the absence of the therapeutic agent; and generating a report with the classification. In embodiments, the computer executable instructions comprise instructions for communicating the classification to a health care provider.

In embodiments, the computer readable storage medium may include instructions for identifying which pathways are operative in the disease cell sample of the subject. The instructions that when executed by a computing device comprise determining whether there is a difference between the output of the biosensor data from a disease cell sample from a subject treated with a first activating or perturbing agent to the output of the biosensor data from a second disease cell sample from the same subject not treated with the first activating or perturbing agent to one another to determine whether the pathway responsive to the first activator or perturbant agent is active in the disease cell sample; identifying the presence of the difference in output as an indication of activity of the pathway, and communicating the activity of the pathway to a health care provider. Activator or perturbant agents and their pathways are described herein.

EXAMPLES

Discussion of Experimental Design

The methods utilize a CReMS to measure the physiologic change of a cell or cell pathway after protein binding within a cell or cell pathway has occurred. It is commonly understood that a drug cannot work unless it is bound, and that nearly all disease genes fall into core signaling pathways. In light of this and the fact biochemical principles of protein binding are universal across cell types, the methods described herein are thus broadly applicable to all cells and cell pathways where protein and other biomolecule binding can occur.

The current state-of-the-art genetic tests cannot indicate directly whether a drug or the pathway is bound, and hence they cannot reliably predict drug response. By identifying the physiologic change that occurs within a cell after a drug is introduced, the CELx test can reliably predict the response of the subject's cells to the drug.

At least three types of CELx tests are envisioned using the methods described herein.
1) A Pathway Shutdown test that determines the efficacy of targeted pathway drugs. In this test, the physiologic change of the test cells caused by the binding of a targeted pathway drug to its cellular target is measured and compared to a baseline measurement.
2) An Anti-Proliferation test that determines the efficacy of anti-proliferation drugs. In this test, the physiologic change of the test cells caused by the inhibition of their proliferative capacity is measured and compared to a baseline measurement.
3) A Combination Test that determines the efficacy of two or more drugs utilized in combination. In this test, the physiologic change of the test cells caused by the drugs is measured and compared to a baseline measurement. A Combination Test can include two or more targeted pathway drugs, two or more anti-proliferation drugs, or one or more of each type of drug.

To demonstrate the embodiments of these tests, 65 experiments on cells from 11 different patients with three different types of cancer were performed. Sixteen different drugs affecting 11 different cell pathways were tested and two different CReMS types were utilized. A list of the tests whose results are reported in the examples of this application is provided in Table 1 below:

TABLE 1

List of Tests Performed

| Example | Drug | Target | Pathway | Patient Cells |
|---|---|---|---|---|
| Ex. 1 | Lapatinib | Her2 receptor | MAPK, RHO, AKT, FAK1, RAS/RAF, PIK3/PTEN, cellular adhesion | B1, B4 |
| Ex. 1 | Trastuzumab | Her2 receptor | MAPK, RHO, AKT, FAK1, RAS/RAF, PIK3/PTEN, Cellular adhesion | B1, B4 |
| Ex. 2 | Paclitaxel | TUBB1, BCL2 | Apoptotic pathways, cellular adhesion | B1, B2 |
| Ex. 3 | Cetuximab and Irionotecan | EGFR Topoisomerase I | MAPK, RHO, AKT, FAK1, RAS/RAF, PIK3/PTEN, Apoptotic pathways, cellular adhesion | C1, C3 |
| Ex. 4 | Capecitabine | Thymidylate synthase | Apoptotic pathways, cellular adhesion | B2 |
| Ex. 4 | Cetuximab | EGFR | MAPK, RHO, AKT, FAK1, RAS/RAF, PIK3/PTEN, cellular adhesion | B3, B5, C1, C2, C1, C2 |
| Ex. 4 | Cisplatin | DNA | Apoptotic pathways, cellular adhesion | L1, L2 |
| Ex. 4 | Docetaxel | TUBB1, BCL2 | Apoptotic pathways, cellular adhesion | B1, B2, B3, B4 |

TABLE 1-continued

List of Tests Performed

| Example | Drug | Target | Pathway | Patient Cells |
|---|---|---|---|---|
| Ex. 4 | Erlotinib | EGFR | MAPK, RHO, AKT, FAK1, RAS/RAF, PIK3/PTEN, cellular adhesions | L1, L2 |
| Ex. 4 | Fluourouracil | Thymidylate synthase | Apoptotic pathways, cellular adhesion | B1, B3 |
| Ex. 4 | Gefitinib | EGFR-TK | MAPK, RHO, AKT, FAK1, RAS/RAF, PIK3/PTEN, cellular adhesion | B1, B2, B3 |
| Ex. 4 | GSK1059615 | PI3K | PI3K/PTEN, cellular adhesion | B1, B2, B3, B4, B5, B7 |
| Ex. 4 | GSK1120212 | MEK1 and MEK 2 | MEK, cellular adhesion | B1, B2, B3, B5, B7, B8 |
| Ex. 4 | Irinotecan | Topoisomerase I | Apoptotic pathways, cellular adhesion | C1, C2 |
| Ex. 4 | Lapatinib | Her2 receptor | MAPK, RHO, AKT, FAK1, RAS/RAF, PIK3/PTEN, cellular adhesion | B2, B3, B5, B6, B7 |
| Ex. 4 | Oxiliplatin | GG, AG, GNG | Apoptotic pathways, cellular adhesion | C1, C2 |
| Ex. 4 | Paclitaxel | TUBB1, BCL3 | Apoptotic pathways, cellular adhesion | B3, B4 |
| Ex. 4 | Paclitaxel and Cisplatin | TUBB1, BCL2, DNA | Apoptotic pathways, cellular adhesion | L1, L2 |
| Ex. 4 | Pazopanib | VEGF receptor | PI3K/PTEN, RAS/RAF, MAK, MKK, cellular adhesion | B1, B2, B3, B5, B7, B8 |
| Ex. 4 | Trastuzumab and Lapatinib | Her2 receptor | MAPK, RHO, AKT, FAK1, RAS/RAF, PIK3/PTEN, cellular adhesion | B1, B2, B3, B4 |
| Ex. 4 | Topotecan | Topoisomerase I | Apoptotic pathways, cellular adhesion | B3 |
| Ex. 4 | Trastuzumab | Her2 receptor | MAPK, RHO, AKT, FAK1, RAS/RAF, PIK3/PTEN, cellular adhesion | B2, B3 |
| Ex. 5 | Cetuximab (optical, impedance) | EGFR | MAPK, RHO, AKT, FAK1, RAS/RAF, PIK3/PTEN, cellular adhesion | B1, B2, B3, B4 |

Rationale for Experimental Design

Tissue:

Tissues from three of the cancers with the highest occurrence rates were chosen.

Breast Cancer.

Breast cancer cells were utilized for 64% of tests since the breast cancer. model is representative of many other cancers in terms of progression, varieties of cellular morphologies, variable metabolic rates, and survival and has aberrant molecules and pathways common to cancers found in many other tissues.

Colon and Lung Cancer.

Colon and lung cancer cells were utilized to demonstrate applicability of the systems and methods of the disclosure in other significant cancer types.

Cells:

Cells from eight patients with common clinical presentations of epithelial cell types for breast cancer were selected for testing. Cells from the patients were obtained using cell sample collection techniques used regularly by those practiced in the art of tissue collection.

Patient B1:

Cells are derived of a TNM stage IIA, grade 3 primary invasive ductal carcinoma of the breast in a 61-year-old woman. The cells have a doubling time of approximately 31 hours, appear as enlarged with occasional amorphous-shaped epithelial cell morphology, and have a very high expression level of ERB B1 and ERB B2 receptors. The Estrogen Receptor (ER), Progesterone Receptor (PR) and Oncogene TP53 status are all three negative.

Patient B2:

Cells are derived of pleural effusion of adenocarcinoma of the breast of a 51-year old Caucasian woman. The cells have a doubling time of approximately 28 hours, appear with invasive, eel-like morphology and have high expression levels of ERB B1 and slightly elevated above normal ERB B2 receptor level, are Estrogen Receptor (ER) negative, Progesterone Receptor (PR) negative and have a high Oncogene TP53 status.

Patient B3:

Cells are derived of pleural effusion of adenocarcinoma of the breast in a 43-year-old white woman; approximately 20 hours doubling time, cobblestone epithelial morphology, very high expression levels of ERB B1 and ERB B2 receptors, and Estrogen Receptor (ER) negative, Progesterone Receptor (PR) negative, and Oncogene TP53 positive status.

Patient B4:

Cells are derived of ascites fluid of invasive ductal carcinoma of the breast in a 47-year-old black woman; has a doubling time of 110 hours, a round, grape-like cluster morphology, has very high expression levels of ERB B1 and ERB B2 receptors, and Estrogen Receptor (ER) positive, Progesterone Receptor (PR) negative, and Oncogene TP53 wild type-low status.

Patient B5:

Cells are derived of primary breast invasive ductal carcinoma in a 60-year-old white woman; 28 hours doubling time, mixture of amorphous spreading and invasive morphology, very high expression levels of ERB B1 and ERB B2 receptors, and Estrogen Receptor (ER) positive, Progesterone Receptor (PR) positive, and Oncogene TP53 positive status.

Patient B6:

Cells are derived of primary breast metaplastic carcinoma TNM stage IV grade 3 in a 70-year-old black woman; approximately 30 hours doubling time, roughened spreading morphology, very high expression levels of ERB B1 and ERB B2 receptors, and Estrogen Receptor (ER) negative, Progesterone Receptor (PR) negative, and Oncogene TP53 mutated low status.

Patient B7:

Cells are derived of pleural effusion of invasive ductal carcinoma of the breast in a 69-year-old white woman; 30 hours doubling time, small mosaic epithelial morphology, low expression levels of ERB B1 and ERB B2 receptors, and Estrogen Receptor (ER) positive, Progesterone Receptor (PR) positive, and Oncogene TP53 wild type status.

Patient B8:

Cells are derived of pleural effusion of adenocarcinoma of the breast in a 48-year-old white woman; 24 hours doubling time, very small grape-like cluster morphology, low expression level of ERB B1 receptors, high expression level of ERB B2 receptors, and Estrogen Receptor (ER) negative, Progesterone Receptor (PR) negative, and Oncogene TP53 wild-type low status.

Cells from two patients with common clinical presentations of epithelial cell types for colon cancer were selected for testing:

Patient C1:

Cells are derived of a male colorectal carcinoma. The cells have a spheroid volume doubling time of 14 hours, high levels of ERB B1, mutant K-Ras, mutant PIK3CA and oncogeneTP53 positive status.

Patient C2:

Cells are derived of a primary colon adenocarcinoma, grade 2, in a 44 year-old Caucasian female. The cells have a spheroid volume doubling time of 46 hours, high levels of ERB B1, mutant BRAF, and oncogene TP53 negative status.

Cells from two patients with common clinical presentations of epithelial cell types for non-small cell lung cancer were selected for testing:

Patient L1:

Cells are derived of pleural effusion of non-small cell lung carcinoma of a 25-year-old male; 48 hours doubling time, epithelial morphology, elevated expression levels of ERB B1 and ERB B2 receptors, PIK3CA positive, and KRAS, BRAF both negative status.

Patient L2:

Cells are derived of a bronchioloalveolar adenocarcinoma of a 52-year-old white male; approximately 30 hours doubling time, epithelial morphology, normal expression levels of ERB B1 and ERB B2 receptors, and BRAF, HRAS, PIK3CA, and KRAS all negative status.

Cell Pathway Targets:

The drugs chosen for these experiments affect eleven cellular pathways which are representative of most cellular regulatory pathways in how they are extensively interconnected, regulated through binding, involve enzymatic activities such as phosphorylation and de-phosphorylation, and control critical cellular functions.

MAPK. (EGFR, EGFR-TK, HER1, HER 2).

Mitogen-activated protein (MAP) kinases are found in all cell types and are essential serine/threonine-specific protein kinases that respond to extracellular stimuli (mitogens, osmotic stress, heat shock and pro-inflammatory cytokines) and regulate various cellular activities, such as gene expression, mitosis, differentiation, proliferation, and cell survival/apoptosis. Their tight regulation is important to maintaining cellular viability. The epidermal growth factor receptor (EGFR; ErbB-1; HER1 in humans) is the cell-surface receptor for members of the epidermal growth factor family (EGF-family) of extracellular protein ligands. Mutations that lead to EGFR overexpression (known as up-regulation) or over-activity have been associated with a number of cancers, including lung cancer, anal cancers and glioblastoma multiforme. Mutations, amplifications or mis-regulations of EGFR or family members are implicated in about 30% of all epithelial cancers, and it is the target of an expanding class of anticancer therapies.

PI3K/PTEN (Her2, 3, 4, VEGF).

The phosphatidylinositol 3-kinase (PI3K) pathway found in nearly all cell types is critical for cell survival and cell growth, and can be activated by growth factors binding to cell surface receptors. It is an intricate signaling cascade that is among the most frequently activated pathways in cancer. It is targeted by genomic aberrations including mutation, amplification and rearrangement more frequently than any other pathway in human cancer. VEGF Receptor is expressed across a wide range of human tumors and cell lines. Expression of VEGF has been shown to lead to the development and maintenance of a vascular network that promotes tumor growth and metastasis. VEGF is expressed in a majority of non-small cell lung cancer (NSCLC), colorectal, and other tumors. VEGF is expressed at higher levels as lung cancer progresses. Moreover, a large and growing body of evidence indicates that VEGF gene expression is associated closely with poor prognosis.

Cell Adhesion.

Cell adhesion pathways intersect nearly all major physiological functions. The pathways involve the binding of a cell to a surface, extracellular matrix or another cell using cell adhesion molecules such as selectins, integrins, and cadherins. Correct cellular adhesion is essential in maintaining multicellular structure. Cellular adhesion can link the cytoplasm of cells and can be involved in signal transduction. All adhesion is mediated by the cell surface, either directly involving integral components of the plasma membrane, or indirectly through material excreted and deposited on the outside of the cell.

MEK.

MEK is a key protein kinase in the RAS/RAF/MEK/ERK pathway, which signals for cancer cell proliferation and survival. MEK is frequently activated in cancer, in particular in tumors that have mutations in the RAS and RAF oncogenes. MEK also regulates the biosynthesis of the inflammatory cytokines TNF, IL-6 and IL-1, which can act as growth and survival factors in cancer. The MEK pathway acts as a central axis in the proliferation of different tumors including melanoma, non-small cell lung, head/neck and pancreatic cancers. And MEK inhibition, either alone or in combination with other agents, is an important therapeutic strategy in treating cancer.

RHO.

Rho proteins are involved in a wide variety of cellular functions such as cell polarity, vesicular trafficking, the cell cycle and transcriptomal dynamics. Rho activation can have a number of different effects in cancerous cells. In the initiation of the tumor, modification of Rho activity can suppress apoptosis and therefore contribute to artificial cell longevity. After natural apoptosis is suppressed, abnormal tumor growth can be observed through the loss of polarity in which Rho proteins play an integral role. Next, the growing mass can invade across its normal boundaries through the alteration of adhesion proteins potentially caused by Rho proteins.

AKT.

AKT is serine/threonine kinase and functions intracellularly as a cardinal nodal point for a constellation of converging upstream signaling pathways, which involve stimulation of receptor tyrosine kinases such as IGF-1R, HER2/Neu, VEGF-R, PDGF-R, and an assembly of membrane-localized complexes of receptor-PI-3K and activation of Akt through the second messenger PIP. Because AKT and its upstream regulators are deregulated in a wide range of solid tumors and hematologic malignancies, and in view of the aforementioned biologic sequelae of this pathway, the AKT pathway is considered a key determinant of biologic aggressiveness of these tumors, and a major potential target for novel anti-cancer therapies.

FAK1.

The biological importance of Focal adhesion kinase 1 (FAK1)-mediated signal transduction is underscored by the fact that this tyrosine kinase plays a fundamental role in embryonic development, in control of cell migration, cell cycle progression, and in apoptosis. It plays a central role in the survival of anchorage-dependent cells and is essential for integrin-linked cell migration—the processes that play important roles in the development of malignancies. FAK is upregulated in a wide variety of human epithelial cancers, with expression being closely correlated to invasive potential. Recently, FAK expression has been implicated in either the progression of tumor cells to malignancy or the pathogenesis of cancer. FAK1 plays a major role in regulating Breast cancer anti-estrogen resistance.

RAS/RAF.

The RAS pathway is one of the most frequently deregulated pathways in cancer. RAS signals through multiple effector pathways, including the RAF/mitogen-activated protein kinase (MAPK)/extracellular signal-regulated kinase (ERK) kinase (MEK)/ERK MAPK and phosphatidylinositol 3-kinase (PI3K)-AKT signaling cascades. The oncogenic potential of these effector pathways is illustrated by the frequent occurrence of activating mutations in BRAF and PIK3CA as well as loss-of-function mutations in the tumor suppressor PTEN, a negative regulator of PI3K. Owing to this important role of Ras in tumorigenesis, the Ras-signalling pathway has attracted considerable attention as a target for anticancer therapy.

MAK Pathway.

Metastasis-associated kinase (MAK) is a novel regulator of the transcription factors required for cell growth. Inhibition of this pathway leads to cell cycle arrest activity.

MKK.

Mitogen-activated protein kinase kinases (MKK) signaling pathways have been to both the transcriptional and the post-translational regulation of vital cellular processes including cell differentiation, proliferation, motility and survival. Since MKK signaling pathways play essential roles in modulating the release of, and the response to VEGF, it is believed that MKK plays an important role in promoting tumor vascularization.

Apoptotic Pathways.

Activation of apoptosis pathways is a key mechanism by which cytotoxic drugs kill tumor cells. Apoptosis occurs through two main pathways. The first, referred to as the extrinsic or cytoplasmic pathway, is triggered through the Fas death receptor, a member of the tumor necrosis factor (TNF) receptor superfamily. The second pathway is the intrinsic or mitochondrial pathway that when stimulated leads to the release of cytochrome-c from the mitochondria and activation of the death signal. Both pathways converge to a final common pathway involving the activation of a cascade of proteases called caspases that cleave regulatory and structural molecules, culminating in the death of the cell. Defects in apoptosis signaling contribute to resistance of tumors.

Therapeutic Agent:

The therapeutic agents chosen include ones representative of small molecule drugs and those derived from antibodies. The therapeutic agents tested include some with mechanisms of action designed to shut down a specific pathway functional within a cell and others designed to cause cell apoptosis.

Cetuximab.

Cetuximab (Erbitux) is a chimeric (mouse/human) monoclonal antibody, an epidermal growth factor receptor (EGFR) inhibitor, given by intravenous infusion for treatment of metastatic colorectal cancer and head and neck cancer. When growth factors bind to their receptors on the surface of the cell, the receptors give a signal that causes cells to divide. Some cancers are caused by mutated receptors that give a signal to divide even without growth factor. That causes the cells to divide uncontrollably. Cetuximab binds to receptors like that and turns off that signal.

Erlotinib.

Erlotinib hydrochloride (Tarceva) is a drug used to treat non-small cell lung cancer, pancreatic cancer and several other types of cancer. It is a reversible tyrosine kinase inhibitor, which acts on the epidermal growth factor receptor (EGFR). Erlotinib specifically targets the epidermal growth factor receptor (EGFR) tyrosine kinase, which is highly expressed and occasionally mutated in various forms of cancer. It binds in a reversible fashion to the adenosine triphosphate (ATP) binding site of the receptor.

Lapatinib.

Lapatinib (Tykerb/Tyverb) is an orally active drug for breast cancer and other solid tumours. It is a dual tyrosine kinase inhibitor which interrupts the HER2 growth receptor pathway. It is used in combination therapy for HER2-positive breast cancer. Lapatinib inhibits the tyrosine kinase activity associated with two oncogenes, EGFR (epidermal growth factor receptor) and HER2/neu (Human EGFR type 2). Over expression of HER2/neu can be responsible for certain types of high-risk breast cancers in women.

Trastuzumab.

Trastuzumab (Herceptin) is a monoclonal antibody that interferes with the HER2/neu receptor. Its main use is to treat certain breast cancers. When it binds to defective HER2 proteins, the HER2 protein no longer causes cells in the breast to reproduce uncontrollably.

Docetaxel.

Docetaxel (Taxotere) is a clinically well-established anti-mitotic chemotherapy medication (that is, it interferes with cell division). It is used mainly for the treatment of breast, ovarian, prostate, and non-small cell lung cancer. Docetaxel is of the chemotherapy drug class; taxane, and is a semi-synthetic analogue of paclitaxel (Taxol).

GSK1059615.

A phosphoinositide 3-kinase inhibitor (PI3K inhibitor) is a potential medical drug that functions by inhibiting a phosphoinositide 3-kinase enzyme which is part of the PI3K/AKT/mTOR pathway, which plays a key role in cancer. Inhibiting this pathway often suppresses tumor growth.

GSK1120212.

GSK1120212 is a potent and selective allosteric inhibitor of the MEK1 and MEK2 (MEK1/2) enzymes with promising antitumor activity.

Pazopanib.

Pazopanib (Votrient) is a potent and selective multi-targeted receptor tyrosine kinase inhibitor of VEGFR-1, VEGFR-2, VEGFR-3, PDGFR-α/β, and c-kit that blocks tumor growth and inhibits angiogenesis.

Paclitaxel.

Paclitaxel is a mitotic inhibitor used to treat patients with lung, ovarian, breast, head and neck cancer, and advanced forms of Kaposi's sarcoma. Paclitaxel stabilizes microtubules and as a result, interferes with the normal breakdown of microtubules during cell division. Together with docetaxel, it forms the drug category of the taxanes.

Fluorouracil.

Fluorouracil (5-FU or f5U) (Adrucil, Carac, Efudix, Efudex and Fluoroplex) is a drug that is a pyrimidine analog which is used in the treatment of cancer. It is a suicide inhibitor and works through irreversible inhibition of thymidylate synthase. It belongs to the family of drugs called antimetabolites.

Capecitabine.

Capecitabine (Xeloda) is an orally-administered chemotherapeutic agent used in the treatment of metastatic breast and colorectal cancers. Capecitabine is a prodrug, that is enzymatically converted to 5-fluorouracil in the tumor, where it inhibits DNA synthesis and slows growth of tumor tissue.

Topotecan.

Topotecan (Hycamtin) is a chemotherapeutic agent that is a topoisomerase inhibitor. It is used to treat ovarian cancer and lung cancer, as well as other cancer types. Topoisomerase-I is a nuclear enzyme that prevents DNA replication, and ultimately leads to cell death. This process leads to breaks in the DNA strand resulting in apoptosis.

Irinotecan.

Irinotecan (Camptosar) is a drug used for the treatment of colon cancer. Irinotecan is activated by hydrolysis to SN-38, an inhibitor of topoisomerase I. The inhibition of topoisomerase I by the active metabolite SN-38 eventually leads to inhibition of both DNA replication and transcription.

Oxaliplatin.

Oxaliplatin is a coordination complex that is used in cancer chemotherapy. These platinum-based drugs are usually classified as alkylating agents. Oxaliplatin is an alkylating agent which functions by forming both inter- and intra-strand cross links in DNA. Cross links in DNA prevent DNA replication and transcription, resulting in cell death.

Cisplatin.

Cisplatin (Platin) is used to treat various types of cancers, including sarcomas, some carcinomas (e.g. small cell lung cancer, and ovarian cancer), lymphomas, and germ cell tumors. It was the first member of a class of platinum-containing anti-cancer drugs, which now also includes carboplatin and oxaliplatin. These platinum complexes react in vivo, binding to and causing crosslinking of DNA, which ultimately triggers apoptosis.

CReMS Types

Two types of CReMS, an optical biosensor and an impedance biosensor, were utilized to measure the physiologic response of cells during the tests and to demonstrate how the amount of physiologic change that occurs can be measured on different types of CReMS.

Prediction Criteria

The amount of physiologic change caused during a CELx test by inhibition of a targeted pathway or an apoptotic pathway was recorded into one of three categories:

1) Non-responder: <5% reduction of the cell index by the highest physiologically relevant concentration of the two drugs as compared to the untreated control cells. This result would indicate that the patient will not respond to the tested drug combination;
2) Responder (weak): Between 5-50% reduction of the cell index by the drugs at any level of concentration. This would indicate that the patient will respond to the combination of test drugs to some degree.
3) Responder (strong): >50% reduction of the cell index by the drugs at any level of concentration. This would indicate that the patient will respond to the test drug.

Cell index using an impedance or optical biosensor is calculated using a baseline starting point of impedance measurement or refractive index measurement. The baseline starting point impedance or refractive index is a physical observable and an indication of the health, viability, and physiologic status of a cell prior to any treatment with drug or other perturbant. Addition of drug or perturbant causes the baseline reading of impedance or refractive index to change in temporal patterns reflective of the specificity of the cellular physiologic change experienced by the cell.

Example 1

Pathway Shutdown Tests Showing Differentiated Response of Two Patients to Two Drugs A CELx Pathway Shutdown test was performed using cells from two HER2 overexpressing breast cancer patients (Patient B1 and B4), two drugs (Lapatinib and Trastuzumab) that are indicated for HER2 positive breast cancers, and human epidermal growth factor (EGF). The physiologic change of the B1 and B4 cells during the test was measured with an impedance biosensor CReMS and the output from the CReMS is recorded in FIGS. 1A and 1B. The comparison of the CELx test results and the third party clinical reference is recorded in FIG. 1C. This example illustrates how the CELx test is able to predict the responsiveness that a patient will have to different targeted pathway drugs by using a CReMS to measure the physiological change in a patient's cells continuously over a period of several hours. This example also illustrates how the presence of a genetic biomarker, in this case an overexpressing HER2 gene, is not a sufficient condition to predict efficacy of the drug.

Materials and Methods

CReM and Microplate:

A 4"×6", 96-well impedance microplate was placed into a Roche Applied Science (Indianapolis, Ind.) xCELLigence SP impedance biosensor designed to maintain constant voltage while measuring simultaneously the impedance of every well. The change in impedance for a particular well is proportional to the number of cells and type of attachment the cells have with the impedance microplate. Changes in impedance indicate a response to perturbation of these small cell populations.

Cells:

Cells from Patient B1 and B4 were utilized. The cells were received at −80° C., thawed and cultured according to standard human epithelial cell handling procedure, typically in T75 culture flasks containing buffered media with serum at 37° C., 5% CO2. Prior to addition to the impedance microplate, the cells were removed from their growth container with versene, counted, and re-suspended in media without serum or other growth factors.

Buffers and Reagents:

Standard media, serum, antibiotics (e.g. penicillin, streptomycin), and other buffers were purchased and used as delivered from ATCC (Manassas, Va., USA) or Life Technologies (Grand Island, N.Y.). Additional growth factor (mature human EGF ca6KDa) was purchased from R&D Systems (Minneapolis, Minn.) and prepared in buffered cell media without growth factors or serum. The therapeutic agent Lapatinib, a small molecule drug, was purchased from Selleck Chemicals (TX, USA); trastuzumab, an antibody drug, was obtained from a clinical dispensary.

Procedure:

Between 6,000-12,000 cells in each well were seeded onto the impedance microplate containing 120 uL standard media with serum. The solution was replaced with media containing no serum to synchronize the cells with respect to physiologic state and pathway stimulation. Twenty microliters of drugs were added to the no-serum media two hours in advance of pathway stimulation. Pathway stimulation was initiated using EC80 doses of receptor ligand (typically 6 nM in 20 uL). The CReMS recording of physiologic change was maintained continuously for several hours from buffer exchange through complete cellular response to the pathway stimulation. The pathway test was performed at 37° C., 5% CO2 and at a relative humidity 75%.

The CReMS recorded data on a continuous basis throughout the test, where the data represented the effects of the two therapeutic agents on the B1 and B4 cells.

Figure 1B:
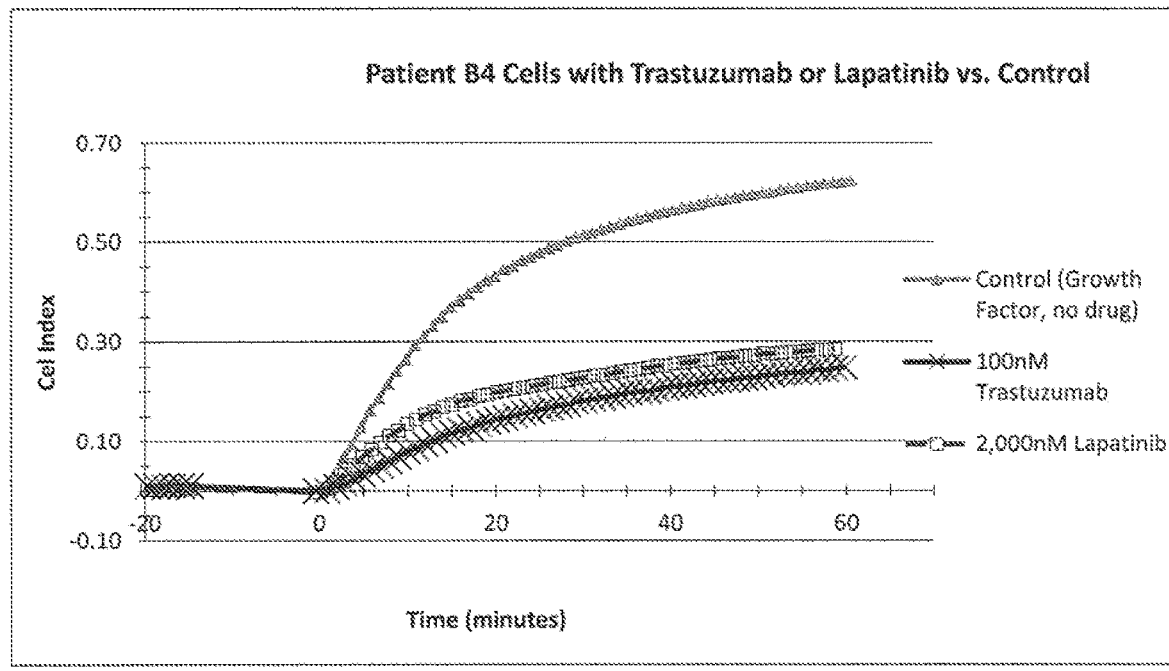

Results:

FIGS. 1A and 1B present the data collected during the CELx test on the B1 and B4 cells respectively with the antibody drug trastuzumab and the small molecule drug lapatinib. The data collected by the impedance CReMS is represented in each figure with time in minutes on the X-axis and the cell index on the Y-axis. The cell index represents the physiologic change of the B1 and B4 cells during the test.

Results indicate that stimulation of the full pathway with a ligand receptor and no drug added generated the highest cell index. After the drug trastuzumab was added to the stimulated B1 cells, the cell index of the test cells changed less than 5%, indicating the B1 test cells were unaffected by the addition of the trastuzumab. Conversely, after the drug lapatinib was added to the B1 cells, the cell index for the test cells decreased by over 50%, indicating that the activity within the targeted pathway is diminished significantly. After the drugs, lapatinib and trastuzumab were each added to separate samples of B4 cells, the cell index of each test cell sample decreased by over 50%. This indicated that the activity within the targeted pathway of each test cell sample was diminished significantly.

Based on these results, the CELx Pathway Shutdown test shown in FIG. 1A predicts that Patient B1 will not respond to trastuzumab but will respond to Lapatinib. The results shown in FIG. 1B also predict that Patient B4 would respond to both trastuzumab and lapatinib. The comparison of the CELx test prediction and the result recorded by third party clinical reference is shown in FIG. 1C; it shows that the CELx test accurately predicted the results recorded by the clinical reference standard, where Patient B1 was found unresponsive to trastuzumab and responsive to lapatinib and Patient B4 was found responsive to both.

Discussion:

In the present example of this invention, the CELx test accurately predicted the efficacy of two drugs, trastuzumab and lapatinib, using cells Patients B1 and B4. The B1 and B4 cells responded to stimulation of the HER2 pathway with a receptor ligand, indicating that the patient could respond to a drug able to shut down activity within that pathway. In this example, the B1 cells demonstrate a differentiated response to the two drugs, despite the drugs having similar mechanisms of action. Patient B1 was found to be responsive to lapatinib and non-responsive to trastuzumab.

This example illustrates how the CELx test can be applied to different types of therapeutic agents, including ones that work at the cell surface, as in the case of trastuzumab, an antibody drug, or ones that work in the cytoplasm, as in the case of the kinase inhibitor drug, lapatinib. It also illustrates how the systems and methods of the disclosure are effective to detect changes in response to drugs that target the MAPK, RHO, AKT, FAK1, RAS/RAF, PIK3 and cell adhesion pathways. This example also illustrates the principle that knowledge of the presence of a relevant genetic biomarker, in this case an overexpressing HER2 gene, is not a sufficient condition to predict whether the drug will function according to its intended mechanism of action. In this example, the drug trastuzumab does not always shut down the HER2 growth factor signaling pathway in every Her2 positive cancer cell type, as it is intended to. Despite similar genetic profiles, Patients B1 and B4 respond differently to trastuzumab as confirmed by the CELx test. Conversely, an embodiment of the method of the invention accurately predicts that another drug, Lapatinib, working at the HER2 site, is able to shut down the pathway as designed for both patients. The results of this example correlate with the response reported by a third party, confirming the ability to use the measurement of physiological change in a patient's diseased cells to predict whether a therapeutic will provide the intended efficacy. With the present invention, a physician selects a treatment for a breast cancer patient based on the actual responsiveness of the tumor cells to the drugs.

Example 2

Anti-Proliferative Tests Showing Differentiated Response of Two Patients to One Drug A CELx Anti-Proliferative test was performed using cells from two breast cancer patients (Patients B1 and B2) and the drug Paclitaxel. The physiologic change of the Bland B2 cells during the test was measured with an impedance biosensor CReMS and the output from the CReMS is recorded in FIGS. 2A and 2B. The comparison of the CELx test results and the third party clinical reference is recorded in FIG. 2C. This example demonstrates the ability of the CELx test to predicting the efficacy of a therapeutic agent by measuring the physiologic change over the course of several days in a patient's cancer cells after an anti-proliferative drug is introduced. This example also demonstrates the role of a baseline, in this case, untreated patient cells, in measuring the results. In addition, the results recorded for patient B2 demonstrate the importance of monitoring the cells' physiological response on a continuous basis over several days because of changes that can occur over time in a cell's responsiveness to a drug.

Materials and Methods

CReMS, Microplate, Reagents, and Buffers:

The CReMS, microplate, reagents, and buffers used in Example 1 are the same as those employed in Example 2, except for the therapeutic agent tested. In Example 2, the therapeutic agent, paclitaxel, was tested. Paclitaxel was purchased from Selleck Chemicals (TX, USA).

Cells:

Breast Cancer cells from Patients B1 and B2 were utilized and handled in the same manner as described in Example 1.

Procedure:

Between 6,000-12,000 cells in each well were seeded onto the impedance microplate containing 120 uL settling media with serum. Forty microliters of the drug paclitaxel were added to one set each of the B1 and B2 cells; another control set of B1 and B2 cells received no drug. The CReMS recording of physiologic change was maintained continuously from when the cells were first seeded on the microplate through complete cellular response, which was between 48-72 hours. The test was performed at 37° C., 5% $CO_2$ and at 75% relative humidity.

Figure 2A:
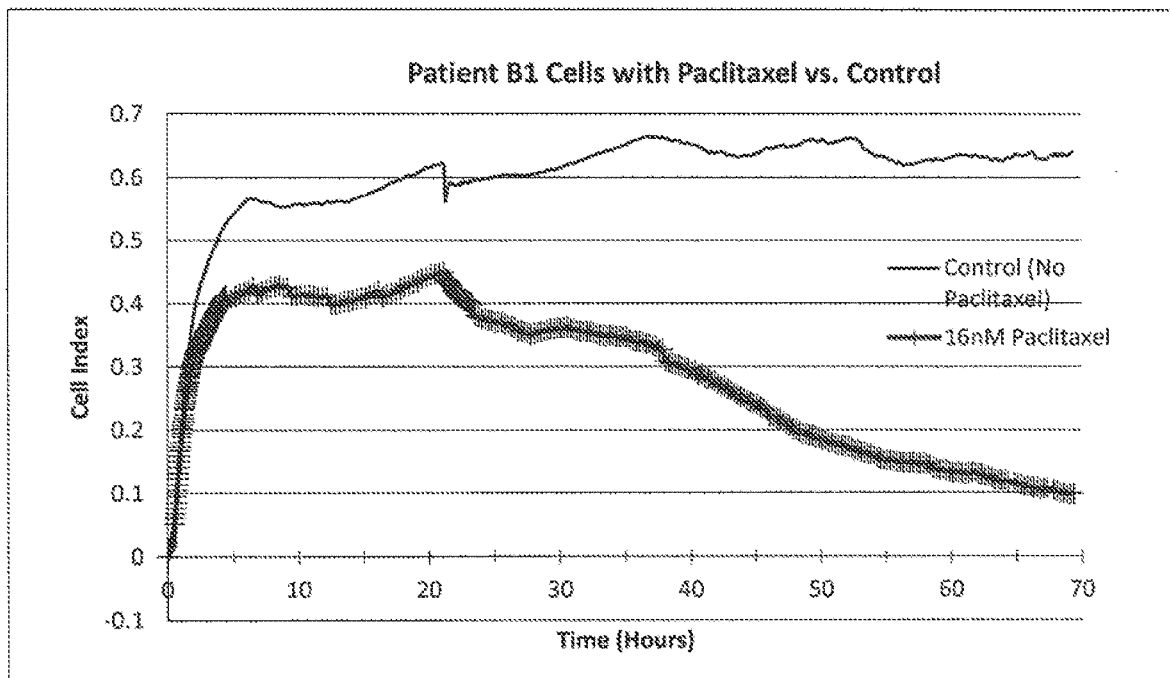
Figure 2B:
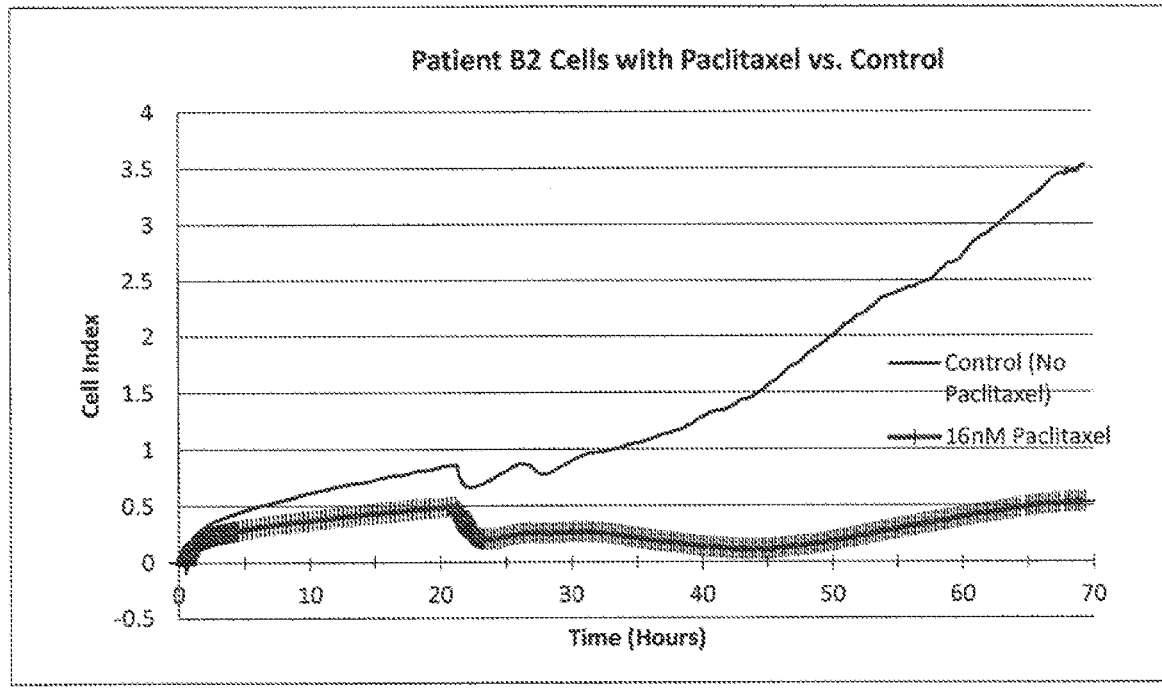

Results:

FIGS. 2A and 2B present the data collected during the CELx test on the B1 and B2 cells with the drug Paclitaxel. The data collected by the impedance CReMS is represented in the figure with time in hours on the X-axis and the cell index on the Y-axis. The cell index represents the physiologic change of the B1 and B2 cells during the test. An increase in the cell index is generally an indication of increase in cell proliferation. Whereas a decrease in long term cell index is generally indicative of loss of cell viability or live cell number decrease. The B2 test cells showed initial responsiveness to Paclitaxel, as reflected in the significant decrease in CReM output compared to the B2 control cells, but after roughly 24 hours, the CReM output reverses, indicating that the test cells begin proliferating and are no longer responsive to the drug. The B1 test cells show immediate and continuous responsiveness to Paclitaxel, as reflected in the decrease in CReM output compared to the B1 control cells throughout the test period. The CELx test results presented in FIGS. 2A and 2B predict that both patients B1 and B2 will respond to paclitaxel. The comparison of the CELx test prediction and the result recorded by third party clinical reference is shown in FIG. 2C; it shows that the CELx test accurately predicted the results recorded by the clinical reference standard, where Patients B1 and B2 were both found responsive to paclitaxel.

Discussion:

In the present example, the CELx test accurately predicted the efficacy of an anti-proliferative drug, paclitaxel, with two breast cancer patients, B1 and B2. Additionally, the CELx test result for Patient B2 indicated that resistance to paclitaxel develops in the short-term, illustrating the importance of monitoring the cells' physiological response on a continuous basis over an extended period of time. This result is important because one of the major issues with drug therapy is the rapid development of resistance to a drug. Time is lost when a patient is prescribed an ineffective therapy. Besides increasing the risk of chemotoxicity and incurring the common side effects of chemotherapy, in many cases, treatment with one drug eliminates the possibility of treatment with another drug that may have been more effective.

Example 3

Combination Tests Showing Response of Two Patients to Two Drugs Taken Together

A CELx Combination test was performed using cells from two colon cancer patients (Patients C1 and C2), EGF, and a combination of two drugs indicated for colon cancer, Cetuximab and Irinotecan. The physiologic change of the C1 and C2 cells during the test was measured with an impedance biosensor CReMS and the output from the CReMS is recorded in FIGS. 3A and 3B. The comparison of the CELx test result and the third party clinical reference is recorded in FIG. 3C. This example demonstrates how the CELx test is able to predict the responsiveness that individual patients will have to a combination of two or more drugs in a way that cannot be done using genetic testing or expression profiling. The test also illustrates how the CELx test operates with colon cancer cells, in addition to breast cancer cells.

Materials and Methods

CReMS, Microplate, Reagents, and Buffers:

The CReMS, microplate, reagents, and buffers used in Examples 1 and 2 are the same as those employed in Example 3, except for the therapeutic agent used. In Example 3, two therapeutic agents, cetuximab and irinotecan, were tested. Irinotecan was purchased from Selleck Chemicals (TX, USA) and cetuximab was obtained from a clinical dispensary.

Cells:

Colon cancer cells from Patients C1 and C2 were utilized and handled in the same manner as described in Example 1.

Procedure:

Between 6,000-12,000 cells in each well were seeded into the impedance microplate containing 120 uL settling media with serum. The solution was replaced with media containing no serum to synchronize the cells with respect to physiologic state. Twenty microliters each of irinotecan and cetuximab was added to one set each of the C1 and C2 cells; another control set of C1 and C2 cells received no drugs. The CReMS recording of physiologic change was maintained continuously from when the cells were first seeded on the microplate through complete cellular response, which was between 48-72 hours. The test was performed at 37° C., 5% $CO_2$ and at 75% relative humidity.

Figure 3A:
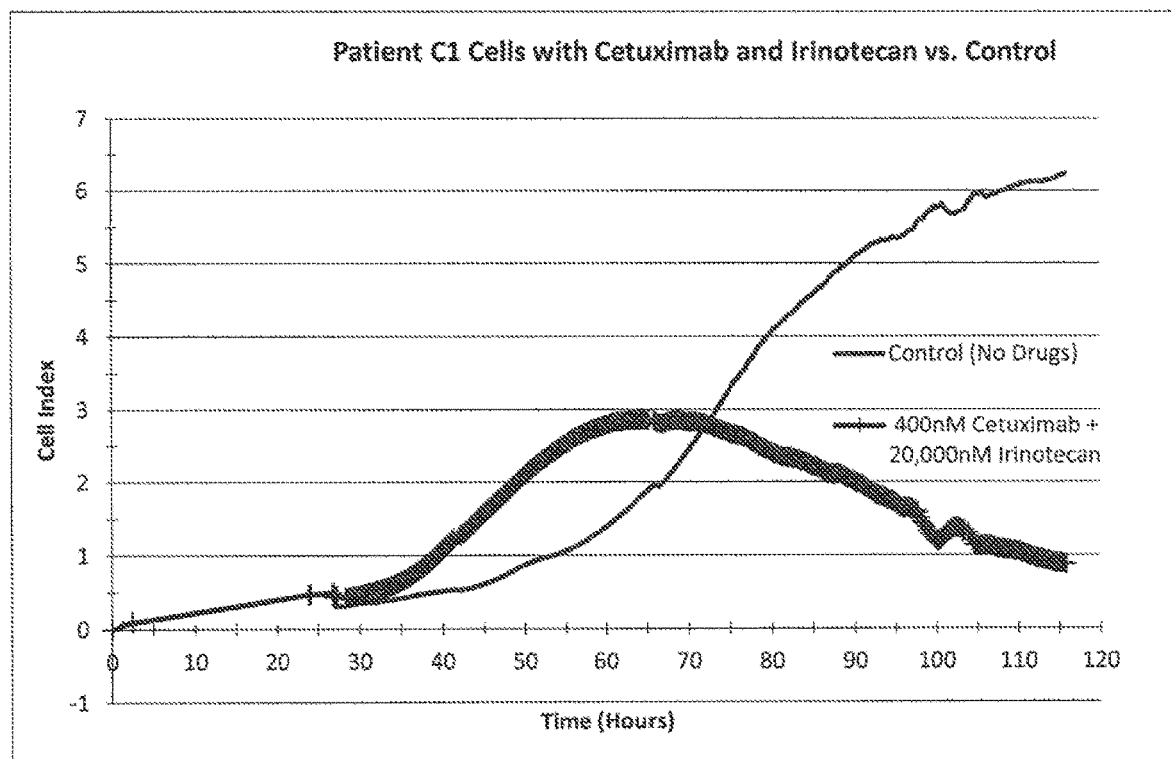
Figure 3B:
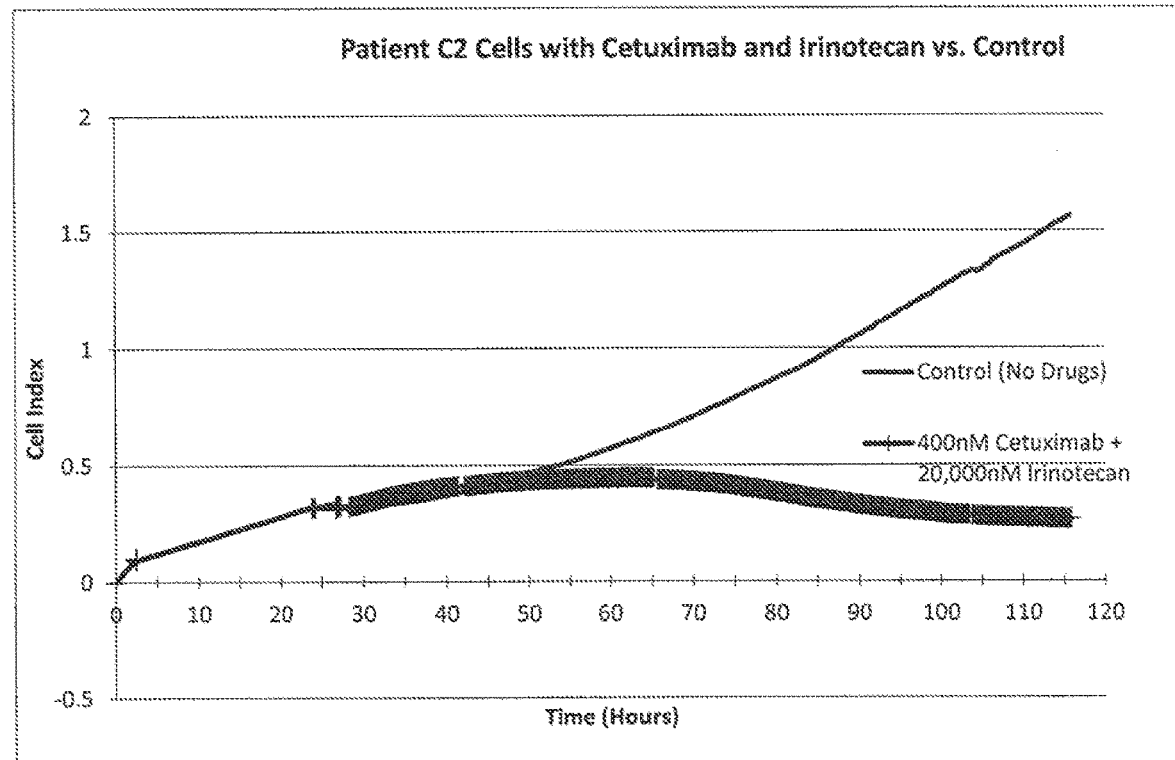

Results:

FIGS. 3A and 3B present the data collected during the CELx test on the C1 and C2 cells and the combination of the antibody drug cetuximab and the small molecule drug irinotecan. The data collected by the impedance CReMS is represented in the figures with time in hours on the X-axis and the cell index on the Y-axis. The cell index represents the physiologic change of the C1 and C2 cells during the test. Results show that the untreated control C1 and C2 cells generated the highest cell index. Results after the two drugs are added to the C1 and C2 test cells show a reduction of the cell index for each cell sample of greater than 50%. These results predict that both patients C1 and C2 will respond to the combination of cetuximab and irinotecan. The comparison of the CELx test prediction and the result recorded by third party clinical reference is shown in FIG. 3C; it shows that the CELx test accurately predicted the results recorded by the clinical reference standard, where Patients C1 and C2 were both found responsive to the cetuximab and irinotecan combination.

Discussion:

In the present example, the CELx test accurately predicted the efficacy of two drugs, cetuximab and irinotecan, with two colon cancer patients, C1 and C2. However, even though the overall results for Patient C1 with the two drugs showed a greater than 50% reduction in the cell index, the CELx test result indicated that one of the drugs, cetuximab, did not cause a physiologic change in Patient C1's cells. This would suggest that the entire therapeutic benefit of the drug combination in Patient C1 was likely due to the irinotecan. If a physician knew that only one drug within a combination therapy was effective, in this case irinotecan, they would then only prescribe the efficacious drug. The CELx test result indicated that Patient 2 was responsive to each individual drug, suggesting the combination of drugs would be more efficacious than a use of only a single drug.

The results illustrate how the CELx test is able to predict the responsiveness of individual patients to a combination of two or more therapeutic agents. The test illustrates how the CELx test operates with colon cancer cells. It further illustrates the physiological responsiveness of cancer cells to different types of drugs, in this case, the antibody drug cetuximab, that works by binding to the cell surface, and an apoptotic pathway inhibitor, in this case irinotecan, which works by binding to the cell nucleus. And it also illustrates the physiological responsiveness of cancer cells to drugs that target the MAPK, RHO, AKT, FAK1, RAS/RAF, PIK3, and cell adhesion pathways and an apoptotic pathway. The result would allow a physician to select a more efficacious treatment for a colon cancer patient.

Example 4

Additional CELx Tests Using Different Drugs

Fifty-one CELx Pathway Shutdown and Anti-Proliferative single drug tests were performed using some of the cell and drug combinations possible from a selection of 11 different patient cells (breast cancer cells from Patients B1, B2, B3, B4, B5, B6, B7), colon cancer cells from Patients C1 and C2, and lung cancer cells from Patients L1 and L2) and 15 different drugs (capecitabine, cetuximab, docetaxel, fluorouracil, gefitinib, GSK1059615, GSK1120212, lapatinib, paclitaxel, pazopanib, trastuzumab, topotecan, cisplatin, erlotinib, and oxiliplatin). Six CELx Combination tests were performed, two with the drug combination of paclitaxel and cisplatin and Patient L1 and L2 cells, and four with the drug combination of trastuzumab and lapatinib and Patient B1, B2, B3, and B4 cells. The physiologic change of the cells and drugs tested was measured with an impedance biosensor CReMS and the summary output from the CReMS is recorded in FIG. 4. The correlation between these CELx test results and the third party clinical reference is recorded in FIG. 7.

Figure 4:
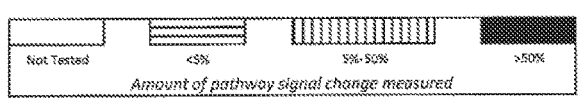
FIG. 4 shows the summary results of 57 CELx tests performed using some of the cell and drug combinations possible from a selection of 11 different patient cells (breast cancer cells from Patients B1, B2, B3, B4, B5, B6, B7, colon cancer cells from Patients C1 and C2, and lung cancer cells from Patients L1 and L2) and 15 different drugs (capecitabine, cetuximab, docetaxel, fluorouracil, gefitinib, GSK1059615, GSK1120212, lapatinib, paclitaxel, pazopanib, trastuzumab, topotecan, cisplatin, erlotinib, and oxiliplatin).
Figure 7:
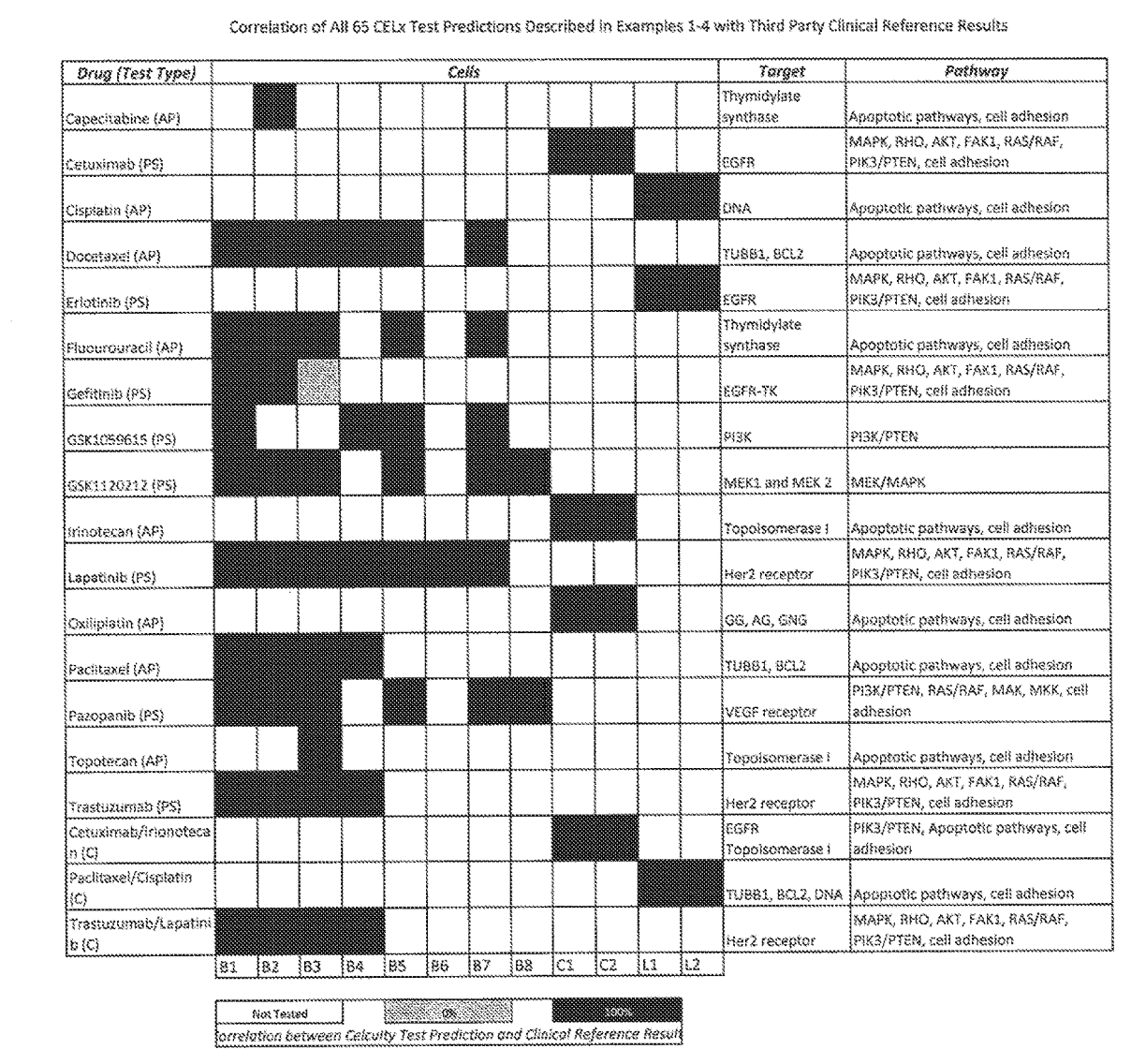

Materials and Methods
CReMS, Microplate, Reagents, and Buffers:
Each of the 57 tests listed in FIG. 4 relied upon the same CReMS, microplate, reagents, and buffers as those described in the Examples 1-3.
Cells:
Cells from Patients B1, B2, B3, B4, B5, B6, B7, C1, C2, L1, and L2 were utilized and handled in the same manner as described in Example 1.
Procedures:
In those experiments involving targeted pathway drugs (cetuximab, gefitinib, GSK1059615, GSK1120212, lapatinib, pazopanib, trastuzumab, and erlotinib) the procedures described in Example 1 were utilized. In those experiments involving anti-proliferative drugs (capecitabine, docetaxel, fluorouracil, paclitaxel, topotecan, cisplatin, and oxiliplatin), the procedures described in Example 2 were utilized. In those experiments involving a combination of drugs, the procedures described in Example 3 were utilized. The list of patient cells and the drug tested with the cells is characterized in FIG. 4.
Results:
The summary results of the 57 CELx tests performed on the various combinations of cells and drugs listed is shown in FIG. 4. For each experiment, the change of the test cells' physiologic response compared to its control cells was calculated. Each box in FIG. 4 classifies the change in physiologic response measured in each experiment as either being greater than 50%, between 5%-50%, or less than 5%. The series of tests represented in FIG. 4 illustrate the CELx test's ability to measure the physiologic change that occurs in a variety of common cancer cell types after they are exposed to wide range of drugs that target a wide range of cellular pathways. The comparison of the CELx test prediction and the result recorded by third party clinical reference is shown in FIG. 7; it shows the CELx test result correlated with the third party clinical reference reported for the patient and drug combination.

Discussion:
In the 57 tests described in this example, the invention described herein demonstrated efficacy with:
Colon, breast, and lung cancer cells;
Targeted pathway drugs that inhibit the MAPK, RHO, AKT, FAK1, RAS/RAF, PI3K, MAK, MKK, MEK and cell adhesion pathways through targets that include EGFR, EGFR-TK, PI3K, MEK1, MEK2, HER2 receptor, and VEGFR; and
Anti-proliferative drugs that target apoptotic pathways through targets that include Topoisomerase I, TUBB1, BCL2, DNA, purine crosslinking (GG, AG, GNG), and thymidylate synthase.
Each of the CELx test results except one correlated with the results for this Patient cell and drug combination.

Example 5

Concordance Tests Between the Results Produced from Different CReMS

A CELx Pathway Shutdown test was performed using cells from four breast cancer patients (Patient B1, B2, B3, B4) with overexpressing epidermal growth factor (EGF) receptors, one drug cetuximab, and human epidermal growth factor (EGF). The physiologic change of the four patients' cells during the test was measured with an impedance biosensor CReMS and an optical biosensor CReMs to demonstrate the correlation of the results produced from the two different CReMS. The output from the CReMS is recorded in FIG. 5. This example illustrates how the CELx test is able to use two different CReMS to obtain the same measurement of physiological change in a patient's cells.

Materials and Methods
CReMS and Microplate:
Two different CReMS were used in this example. In one series of tests, a 4"×6", 96-well impedance microplate was placed into a Roche Applied Science (Indianapolis, Ind.) xCELLigence SP impedance biosensor designed to maintain constant voltage while measuring simultaneously the impedance of every well. The change in impedance for a particular well is proportional to the number of cells and type of attachment the cells have with the impedance microplate. Changes in impedance indicate a response to perturbation of these small cell populations. In the other series of tests, a 4"×6", 384-well optical microplate was placed into a PerkinElmer Instruments (Waltham, Mass.) EnSpire Multimode optical biosensor designed to scan 850 nanometer near infrared reflected light in each well. The change in reflected wavelength for a particular well is proportional to the number of cells and type of attachment the cells have with the optical microplate. Changes in reflected wavelength indicate a response to the perturbation of the small cell populations in the well.

Reagents and Buffers:
The reagents and buffers used in Example 1 are the same as those employed in Example 5, except for the therapeutic agent employed. In Example 5, the therapeutic agent cetuximab was tested. Cetuximab was acquired from a medical dispensary.

Cells:

Breast cancer cells from Patients B1, B2, B3 and B4 were utilized in both set of tests and handled in the same manner as described in Example 1.

Procedure:

In the set of tests performed with the impedance biosensor CReMS, between 6,000-12,000 cells in each well were seeded onto the impedance microplates containing 120 uL settling media with serum. Forty microliters of the drug cetuximab was added to the no-serum media containing one set each of the B1, B2, B3, and B4 patient cells two hours in advance of pathway stimulation; another control set of B1, B2, B3 and B4 cells received no drug. Pathway stimulation was initiated using EC80 doses of receptor ligand (6 nM in 20 uL). The impedance CReMS recording of physiologic change was maintained continuously from when the cells were first seeded on the microplates through complete cellular response, which ranged between 20-48 hours. The test was performed at 37° C., 5% CO2 and at 75% relative humidity.

In the set of tests performed with the optical biosensor CReMS, between 6,000-12,000 cells in each well were seeded onto the optical microplates containing 60 uL settling media with serum. Twenty microliters of the drug cetuximab was added to the no-serum media containing one set each of the B1, B2, B3, and B4 patient cells two hours in advance of pathway stimulation; another control set of B1, B2, B3 and B4 cells received no drug. Pathway stimulation was initiated using EC80 doses of receptor ligand (6 nM in 20 uL). The optical CReMS recording of physiologic change was maintained continuously from when the cells were first seeded on the microplates through complete cellular response, which ranged between 20-48 hours. The tests was performed at 25° C.–30° C., <5% CO2 and at 30% relative humidity.

Figure 5:
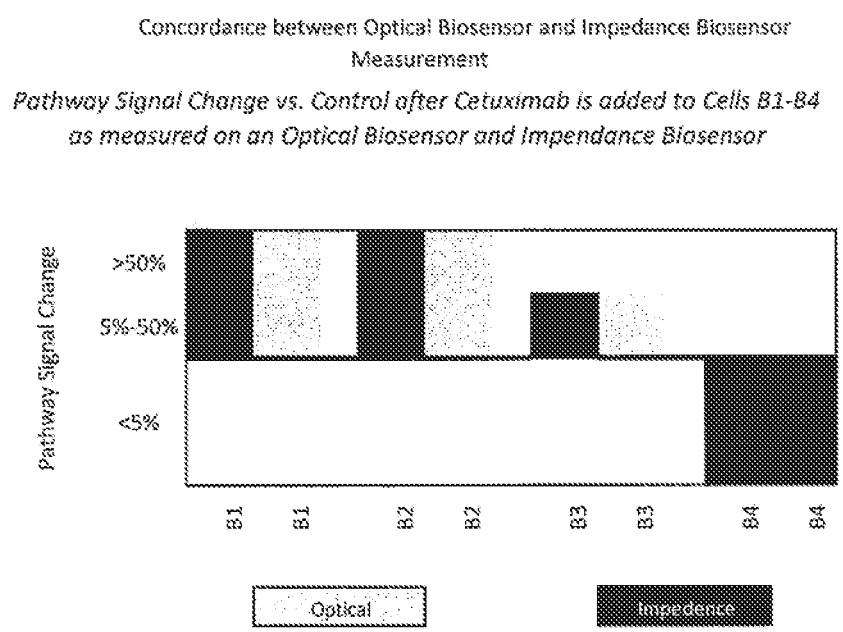
FIG. 5 shows the summary results of eight CELx tests performed separately on cells from four breast cancer patients (B1, B2, B3, and B4) with the drug Cetuximab and EGF. One set of tests on cells B1, B2, B3, and B4 was performed using an "Optical" biosensor CReMS and another set of tests on the same cells was performed using an "Impedance" biosensor CReMS. The results are presented in a summary fashion showing the range of percentage change in output recorded by the CReMS. For each patient cell tested, the amount of physiologic change recorded by each CReMS was identical. These results illustrate that the CELx test method can utilize different types of CReMS' that measure different physiologic changes in cells.

Results:

FIG. 5 shows the summary results of the eight CELx tests performed separately on cells from four breast cancer patients (B1, B2, B3, and B4) with the drug cetuximab and EGF. One set of tests on cells B1, B2, B3, and B4 was performed using an optical biosensor CReMS and another set of tests on the same cells was performed using an impedance biosensor CReMS. The results are presented in a summary fashion showing the range of percentage change in output recorded by the CReMS. For each patient cell tested, the amount of physiologic change recorded by each CReMS was identical. These results illustrate that the CELx test method can utilize different types of CReMSs that measure different physiologic changes in cells.

Discussion:

In the present example, a CELx Test was performed on two different CReMS that have different transducer interfaces to measure cellular physiologic change. Despite the significant differences in the devices employed for acquiring the physiological response to treatment, the optical biosensor CReMS and the impedance biosensor CReMS provided identical results for each of the patient samples. This result is important for the extension of the present invention to many CReMS types and illustration of the universality of the present invention of using an individual patient's cellular physiologic change to predict therapeutic response to drugs.

Summary of Examples

Summary of CELx Test Results and Clinical Predictions

Figure 6:
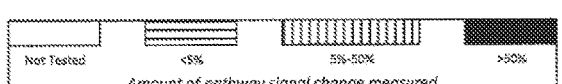
FIG. 6 provides the summary results of the 65 tests described in Examples 1-4. A total of 16 different drugs that target 11 different cellular pathways were introduced in this set of experiments to cell samples from 11 patients with three different types of cancer. For each experiment, the change of the test cells' physiologic response compared to its baseline, or control cells, was calculated. Each box in FIG. 6 classifies the change in physiologic response measured in each experiment as either being greater than 50%, between 5%-50%, or less than 5%. The CELx test predicts a positive patient response to the therapy when the change in physiologic response is between 5%-50% or greater than 50% and it predicts no patient response to the therapy when the change in physiologic response is less than 5%. The responses are shown as follows: greater than 50% (solid box), between 5%-50%, (vertical shaded box), less than 5% (horizontal shaded box), or not tested (open box). The series of experiments represented in this figure illustrate the CELx test's ability to measure the physiologic change that occurs in a variety of cancer cell types after they are exposed to wide range of drugs that affect a wide range of cellular pathways.

The summary results of all 65 total CELx tests described in Examples 1-4 is presented in FIG. 6. The correlation (either 0% or 100%) between the CELx test results described in FIG. 6 and results from third party clinical references that recorded the patient's responsiveness to a single drug or drug combination is shown in FIG. 7. In all 65 tests except one, the CELx test prediction and the third party measurement generated the same result, illustrating the power of the CELx test to predict breast, lung, and colon patient response to 16 different drugs that target a wide range of cellular pathways.

The CELx test predictions for the various patient cancer cells tested in Examples 1-4 versus the third party record is provided in FIGS. 8A, 8B, 8C and 8D. A CELx test result that accurately predicts that a patient would respond to a drug or drug combination is denoted as a True Positive (TP) result. An accurate prediction that a patient would not respond to a drug or drug combination is denoted as a True Negative (TN) result. An inaccurate prediction that a patient would respond to a drug or drug combination is denoted as a False positive (FP) and an inaccurate prediction that a patient would not respond to a drug is denoted as a False Negative (FN).

FIG. 8A records the comparison of results for all tests performed in Examples 1-4 with the 12 cancer patient cells that were tested singly or in combination with 16 different drugs versus the third party record. FIG. 8B records the comparison of results for the eight breast cancer patient cells that were tested singly and in combination with thirteen different drugs versus the third party record. FIG. 8C records the comparison of results for the two different colon cancer patient cells that were tested singly and in combination with three different drugs. FIG. 8D records the comparison of results for the two different lung cancer patient cells that were tested singly and in combination with three different drugs. In each Figure, the CELx tests are shown to predict accurately whether a patient will or will not respond to a particular drug or combination of drugs except in one case In FIG. 8B, it can be seen that one patient breast cancer cell sample that was expected to be a responder to gelfitinib did not show a response in the CReMS testing.

The sensitivity and specificity of the CELx test for the patient cells and drug tested in Examples 1-4 as well as for the sub-groups of patients, drugs, pathways, and CReMS types tested is provided in FIG. 9. Overall and within each of the sub-groups studied, the CELx test generated high sensitivity (98%+) and specificity (99.9%+). These results illustrate the predictive power of the test across the different cancer cell types, drug types, CReMS types, and pathways targeted in the tests described in Examples 1-4.

What is claimed is:

1. A method of treating a human subject diagnosed with cancer, the method comprising:

administering to the subject a human epidermal growth factor receptor family (HER) targeted therapeutic that is therapeutically active in a pathway in which signaling has been measured in the subject's cancer cells by a method comprising:

culturing a sample comprising viable cancer cells obtained from the subject;

contacting the sample with the first agent that is a HER targeted therapeutic and with a second agent that is known to selectively affect the same HER signaling pathway the first agent is intended to address, so as to upregulate or downregulate the HER signaling pathway as measured by an effect on cell adhesion or attachment, to produce a sample contacted with both the first agent and the second agent;

continuously measuring cell adhesion or attachment of viable primary or metastatic cancer cells in the sample contacted with both the first agent and the second agent, relative to a sample of viable primary or metastatic cancer cells obtained from the subject which sample is contacted with the first agent or the second agent alone;

determining by mathematical analysis of the continuous measurements an output value, expressed as a percentage, that characterizes whether a change in cell adhesion or attachment has occurred in the sample contacted with both the first agent and the second agent, as compared to the sample contacted with the first agent or the second agent alone; and administering to the subject a HER targeted therapeutic that affects the same HER signaling pathway as the first agent wherein the output value that characterizes the change in cell adhesion or attachment is equal to or greater than 50%, indicating the HER signaling pathway is active in the subject's cancer cells.

2. The method of claim 1, wherein the HER targeted therapeutic is selected from a list consisting of neratinib, gefitinib, erlotinib, cetuximab, panitumumab, trastuzumab, lapatinib, and pertuzumab.

3. The method of claim 2, wherein the HER targeted therapeutic is trastuzumab.

4. The method of claim 2, wherein the HER targeted therapeutic is lapatinib.

5. The method of claim 2, wherein the HER targeted therapeutic is pertuzumab.

6. The method of claim 2, wherein the HER targeted therapeutic is cetuximab.

7. The method of claim 1, wherein the second agent is neuregulin.

8. The method of claim 1, wherein the second agent is heregulin.

9. The method of claim 1, wherein the second agent is an epidermal growth factor.

10. The method of claim 1, wherein cell adhesion or attachment is measured using an impedance biosensor or an optical biosensor.

11. The method of claim 1, wherein the change in cell adhesion or attachment is assessed using Euclidean analysis.

12. The method of claim 1, wherein the cancer is breast cancer.

13. The method of claim 1, wherein the sample is cultured in a media free of serum.

14. The method of claim 13, wherein the media free of serum further comprises at least one growth factor.

15. The method of claim 13, wherein the media free of serum further comprises at least one anti-apoptotic agent.

16. The method of claim 1, wherein the sample consists essentially of viable primary or metastatic cancer cells obtained from the subject and wherein the sample is cultured in a media free of serum.

17. The method of claim 16, wherein the media free of serum further comprises at least one growth factor.

18. The method of claim 16, wherein the media free of serum further comprises at least one anti-apoptotic agent.

19. The method of claim 1, wherein the HER targeted therapeutic that is administered to the subject is the first agent.

20. The method of claim 1, wherein the HER targeted therapeutic that is administered to the subject is different from the first agent but targets the same HER signaling pathway as the first agent.

* * * * *